US00RE40377E

(19) United States
(12) Reissued Patent
Williamson, IV et al.

(10) Patent Number: US RE40,377 E
(45) Date of Reissued Patent: Jun. 10, 2008

(54) MEANS AND METHOD OF REPLACING A HEART VALVE IN A MINIMALLY INVASIVE MANNER

(75) Inventors: Warren P. Williamson, IV, Loveland, OH (US); Paul A. Spence, Louisville, KY (US); George T. Christakis, Toronto (CA); Mark Ortiz, Milford, OH (US)

(73) Assignee: Cardiovascular Technologies LLC, Loveland, OH (US)

(21) Appl. No.: 10/863,862

(22) Filed: Jun. 7, 2004

(Under 37 CFR 1.47)

Related U.S. Patent Documents

Reissue of:
(64) Patent No.: 6,402,780
Issued: Jun. 11, 2002
Appl. No.: 09/306,448
Filed: May 6, 1999

U.S. Applications:
(63) Continuation-in-part of application No. 08/964,026, filed on Nov. 4, 1997, now abandoned, which is a continuation-in-part of application No. 08/802,948, filed on Feb. 21, 1997, now Pat. No. 6,042,607, which is a continuation-in-part of application No. 08/606,343, filed on Feb. 23, 1996, now Pat. No. 5,716,370.

(51) Int. Cl.
*A61F 2/24* (2006.01)

(52) U.S. Cl. ..... 623/2.11; 623/2.41; 623/23.68; 606/153; 606/151

(58) Field of Classification Search ..... 606/149, 606/150, 151, 153, 142, 143; 623/2.11, 2.41, 623/23.68
See application file for complete search history.

(56) References Cited

U.S. PATENT DOCUMENTS 3,143,742 A 8/1964 Cromie
3,370,305 A 2/1968 Goot et al.

(Continued)

FOREIGN PATENT DOCUMENTS

| | | |
|---|---|---|
| DE | 19711288 A1 | 10/1998 |
| WO | 9739688 | 10/1997 |
| WO | 9858591 | 12/1998 |

OTHER PUBLICATIONS

Examiner Natalie R. Pous, US PTO Office Action for co–pending Application No. 10/681,700, dated Mar. 20, 2007.
Examiner Amy T. Lang, US PTO Office Action for co–pending Application No. 11/004,445, dated Feb. 1, 2007.

*Primary Examiner*—Paul B. Prebilic
(74) *Attorney, Agent, or Firm*—William A. English; Vista IP Law Group LLP

(57) ABSTRACT

A heart valve can be replaced using minimally invasive methods which include a sutureless sewing cuff that and a fastener delivery tool that holds the cuff against the patient's tissue while delivering fasteners to attach the cuff to the tissue from the inside out. The tool stores a plurality of fasteners and is self-contained whereby a fastener is delivered and placed all from inside a vessel. The fasteners are self-forming whereby they do not need an anvil to be formed. Anchor elements are operated from outside the patient's body to cinch a prosthesis to an anchoring cuff of the valve body. The cuff is releasably mounted on the tool and the tool holds the cuff against tissue and drives the fastener through the cuff and the tissue before folding over the legs of the fastener whereby secure securement between the cuff and the tissue is assured. Fasteners are placed and formed whereby fasteners are located continuously throughout the entire circumference of the cuff. A minimally invasive surgical method is disclosed, and a method and tool are disclosed for repairing abdominal aortic aneurysms in a minimally invasive manner. Fasteners that are permanently deformed during the process of attaching the cuff are disclosed as are fasteners that are not permanently deformed during the attaching process.

72 Claims, 44 Drawing Sheets

U.S. PATENT DOCUMENTS 3,574,865 A 4/1971 Hamaker
3,587,115 A * 6/1971 Shiley ..... 623/2.38
3,657,744 A * 4/1972 Ersek ..... 128/898
3,839,741 A 10/1974 Haller
3,959,827 A 6/1976 Kaster
3,974,854 A 8/1976 Kurpanek
3,997,923 A 12/1976 Possis
4,388,735 A 6/1983 Ionescu et al.
4,485,816 A 12/1984 Krumme
4,666,442 A 5/1987 Arru et al.
4,680,031 A 7/1987 Alonso
4,687,483 A 8/1987 Fisher et al.
4,725,274 A 2/1988 Lane
4,816,029 A 3/1989 Penny, III et al.
4,892,541 A 1/1990 Alonso
5,032,128 A 7/1991 Alonso
5,037,434 A 8/1991 Lane
5,071,431 A 12/1991 Sauter et al.
5,242,457 A 9/1993 Akopov et al.
5,304,204 A 4/1994 Bregen
5,406,857 A 4/1995 Eberhardt
5,449,384 A 9/1995 Johnson
5,531,784 A 7/1996 Love et al.
5,549,666 A 8/1996 Hata et al.
5,618,311 A 4/1997 Gryskiewicz
5,716,370 A 2/1998 Williamson et al.
5,725,554 A 3/1998 Simon
5,814,100 A 9/1998 Carpentier et al.
5,830,239 A 11/1998 Toomes
5,843,179 A 12/1998 Vanney et al.
5,860,992 A 1/1999 Daniel et al.
5,861,028 A 1/1999 Angell
5,876,436 A 3/1999 Vanney et al.
5,891,160 A 4/1999 Williamson et al.
5,904,696 A * 5/1999 Rosenman ..... 606/151
5,910,170 A 6/1999 Reimink et al.
5,961,549 A 10/1999 Nguyen et al.
5,961,550 A 10/1999 Carpentier et al.
5,976,183 A 11/1999 Ritz
5,984,959 A 11/1999 Robertson et al.
6,001,110 A 12/1999 Adams
6,007,577 A 12/1999 Vanney et al.
6,030,392 A * 2/2000 Dakov ..... 606/139
6,036,702 A * 3/2000 Bachinski et al. ..... 606/153
6,042,607 A * 3/2000 Williamson et al. ..... 623/2.11
6,059,827 A 5/2000 Fenton, Jr.
6,074,418 A * 6/2000 Buchanan et al. ..... 623/2.11
6,096,074 A 8/2000 Pedros
6,102,944 A 8/2000 Huynh et al.
6,106,550 A 8/2000 Magovern et al.
6,143,025 A 11/2000 Stobie et al.
6,149,660 A 11/2000 Laufer et al.
6,168,614 B1 1/2001 Anderson et al.
6,176,877 B1 * 1/2001 Buchanan et al. ..... 623/2.39
6,197,054 B1 3/2001 Hamblin, Jr. et al.
6,214,043 B1 4/2001 Krueger et al.
6,391,053 B1 5/2002 Brendzel et al.
6,425,916 B1 7/2002 Garrison et al.
2004/0093024 A1 5/2004 Lousararian et al.

* cited by examiner

FIG. 3.
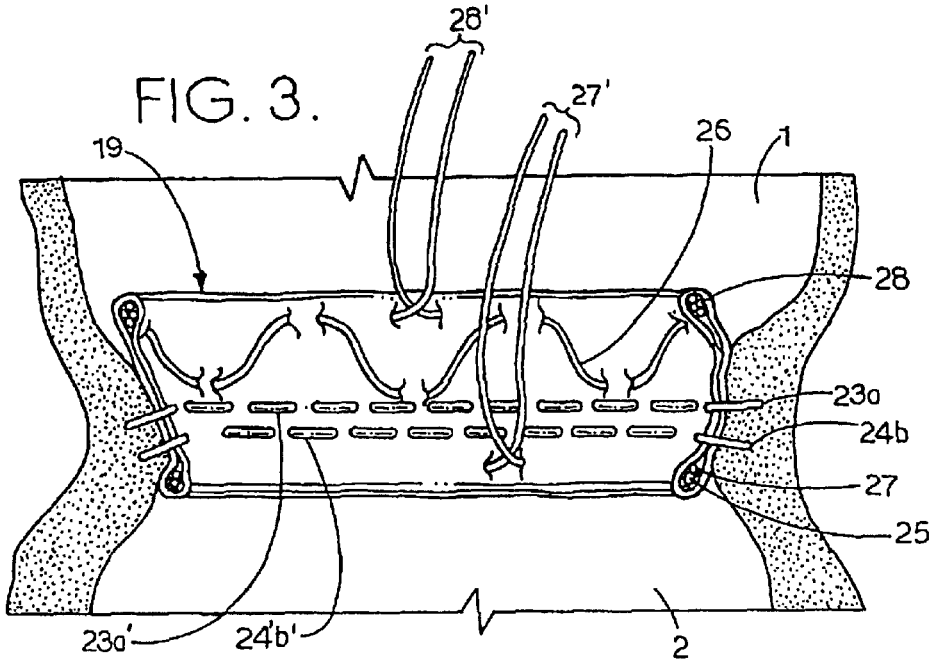
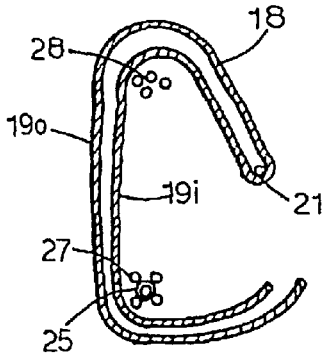
FIG. 6.
FIG. 7.
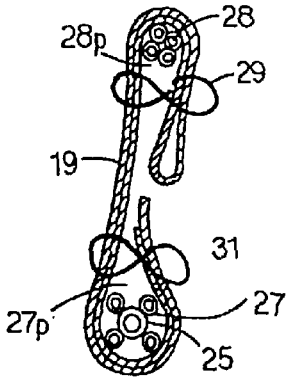
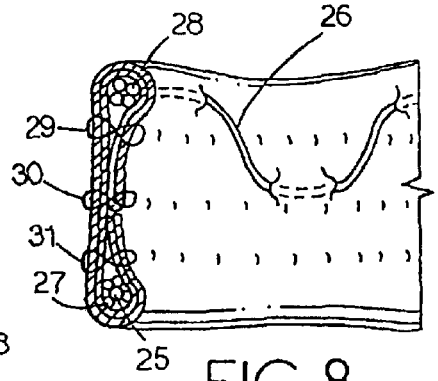
FIG. 8.

FIG. 4.
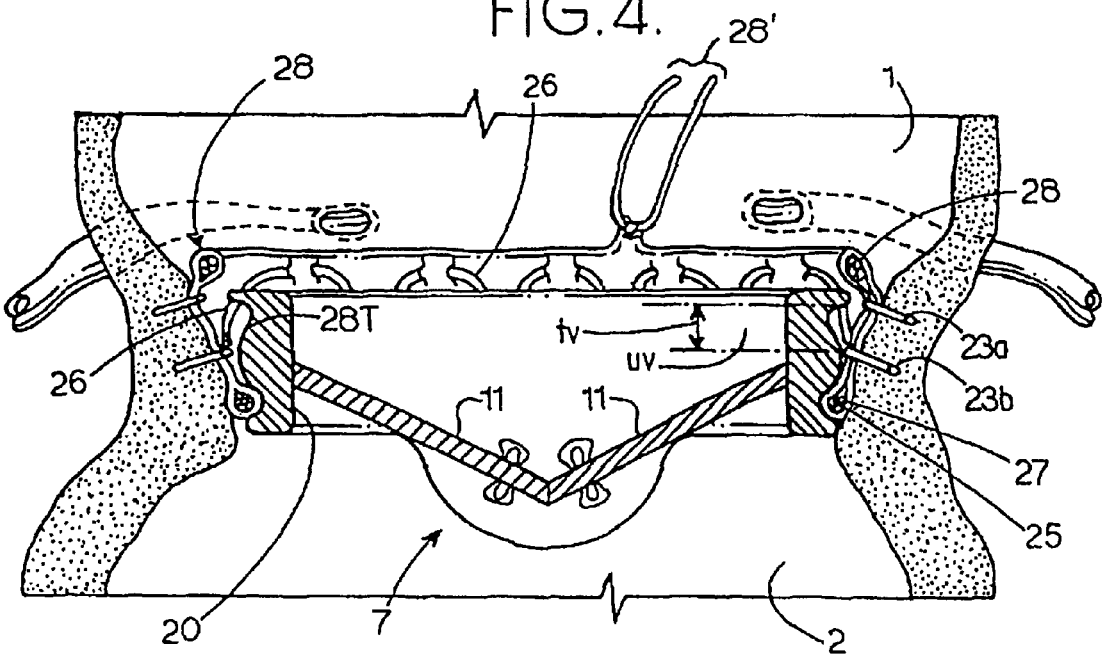
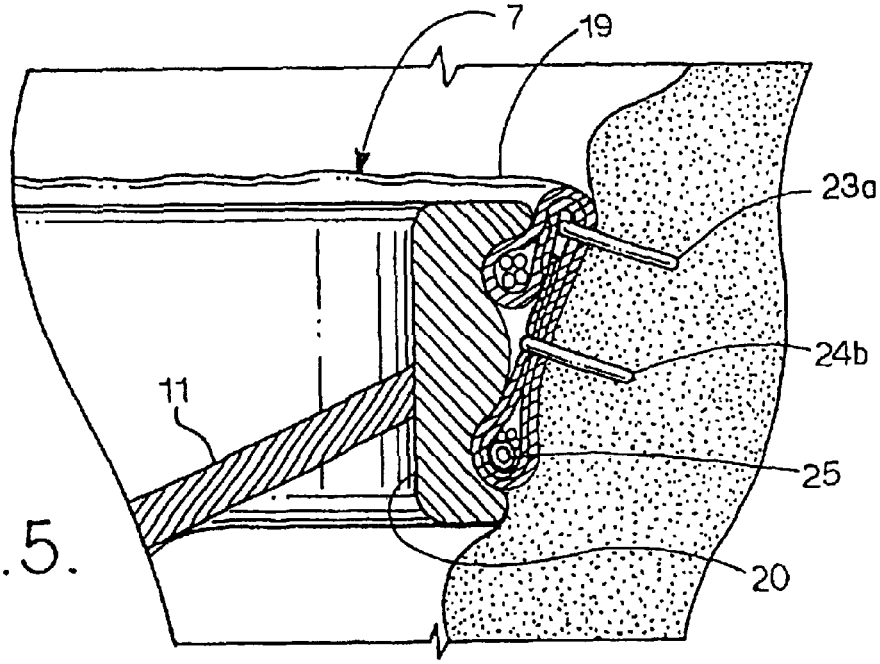
FIG. 5.

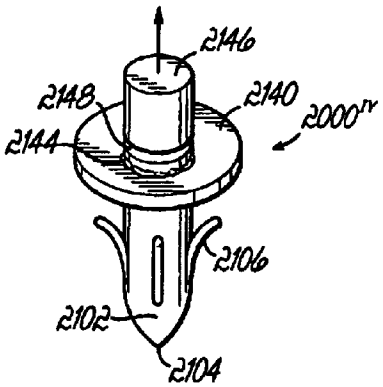
FIG. 64
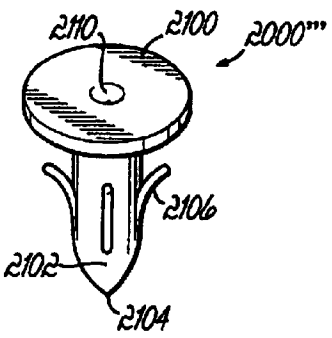
FIG. 65
FIG. 66
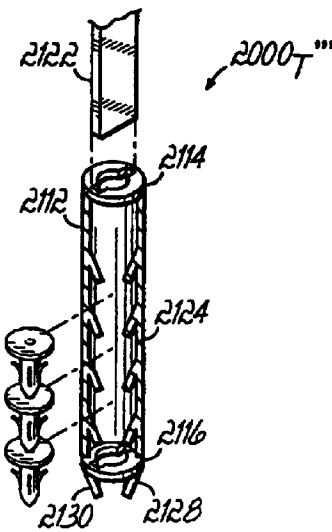
FIG. 67
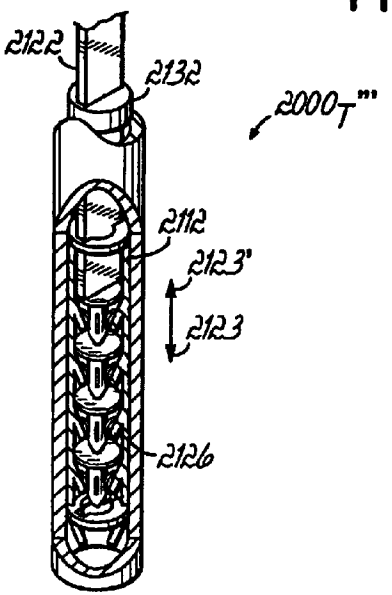
FIG. 68

MEANS AND METHOD OF REPLACING A HEART VALVE IN A MINIMALLY INVASIVE MANNER

Matter enclosed in heavy brackets [ ] appears in the original patent but forms no part of this reissue specification; matter printed in italics indicates the additions made by reissue.

CROSS REFERENCE TO RELATED APPLICATIONS

The application is a continuation-in-part (CIP) of U.S. Ser. No. 08/964,026 filed on Nov. 4, 1997 and now abandoned, which is a CIP of U.S. Ser. No. 08/802,948 filed on Feb. 21, 1997 and now U.S. Pat. No. 6,042,607, which is a CIP of U.S. Ser. No. 08/606,343 filed on Feb. 23, 1996, now U.S. Pat. No. 5,716,370.

TECHNICAL FIELD OF THE INVENTION

The present invention relates to the general art of prosthetic devices, and to the particular field of prosthetic heart valves and surgical tools, fasteners and techniques associated therewith.

BACKGROUND OF THE INVENTION

It is well known that heart diseases may result in disorders of the cardiac valves. For example, diseases such as rheumatic fever can cause the shrinking or pulling apart of the valve orifice, while other diseases may result in endocarditis, an inflammation of the endocardium or lining membrane of the heart. The resulting defects in the valves hinder the normal functioning of the atrioventricular orifices and operation of the heart. More specifically, defects such as the narrowing of the valve stenosis and/or the defective closing of the valve, referred to as valvular insufficiency, result in an accumulation of blood in a heart cavity or regurgitation of blood past the valve. If uncorrected, prolonged valvular stenosis or insufficiency may cause damage to the heart muscle, which may eventually necessitate total valve replacement.

These defects may be associated with any of the cardiac valves. For example, if the mitral valve stenosis connecting the left auricle with the left ventricle narrows, blood will accumulate in the left auricle. Similarly, in the case of mitral insufficiency, the mitral valve does not close perfectly, and blood in the left ventricle is regurgitated past the closed mitral valve into the left auricle when the ventricle closes.

In many cases, complete valve replacement is required. Mechanical artificial heart valves for humans are frequently fabricated from titanium, prolitic carbon or tissue, including tissue from cows, pigs or humans. Such valves have been used because of their nonthrombogenic properties. Human blood does not coagulate on contact with such valves. Moreover, they are lightweight, hard and quite strong. Therefore, such valves have become widely accepted and used by many surgeons. Any new prosthetic valve or surgical technique associated therewith should account for this. One popular prosthetic valve includes such a hard body and a knit fabric sewing or structure cuff fixedly attached thereto as by drawstrings made of plastics-type material. The sewing cuff is sutured in place on the patient's tissue, and that tissue grows into the fabric providing a secure seal for the prosthetic valve. As will be discussed below, even though this is a widely accepted valve, there are problems and drawbacks.

A standard implantable mechanical heart valve usually has an annular valve housing or body to provide a passageway for blood. Occulders are mounted in the annular body and open or close the blood flow passageway. Usually there are one or two occulders, but occasionally triple occluder configurations have been proposed. On the outside of the valve body there is usually an external, circumferential surface configured as a groove. The purpose of this groove is to facilitate attachment of the above-discussed suture ring to the valve body.

As above mentioned, replacement of heart valves has become a widely accepted procedure. Currently, as many as eighty thousand heart valve prostheses are implanted in the United States alone. This procedure is very expensive. It requires the talents of a highly skilled surgeon, perfusionist and anesthesiologist as well as the supporting staff and equipment required to keep the patient on a heart/lung bypass machine during the operation. While this procedure currently works very well, operating time is still extensive and the longer the patient is on bypass equipment, the greater the risk to the patient. Furthermore, hand suturing is tedious and time consuming further lengthening the time the patient is on cardiopulmonary bypass and hypothermia. This may increase the chances of tissue damage to the patient.

Therefore, there is a need for a heart valve replacement procedure that reduces the surgical time required for the operation.

Still further, many currently used surgical techniques are invasive and often require breaking of bones. This increases the time and difficulty of the recovery. Therefore, there is a need to develop a prosthetic heart valve and a procedure for implanting same that reduces the invasiveness of this surgery.

As above mentioned, hand suturing of prosthetic heart valves in place is widely accepted. However, this requires the opening of the patient's chest wall to gain access to the aortic valve through a transverse incision in the ascending aorta. The distance from the incision down to the valve is usually two to two and one halve centimeters with an aortic lumen diameter of between seventeen and thirty millimeters. This creates a very long and narrow tube into which the surgeon must place sutures. While this is a tedious procedure in an "open chest" case, it is very challenging to accomplish through any small incision between the ribs or through a thoracic inlet, as would be required in any minimally invasive procedure. Therefore there is a need for a device and method that can secure the valve remotely from outside the chest wall.

A further problem associated with suturing some prostheses is that the valve is bulky and reduces the inside diameter of the valve body. A reduced inside diameter of the valve reduces the flow area of the valve resulting in increased transvalvular pressure gradients resulting in increased work for the heart muscle. A reduced flow area for such a valve may adversely influence blood flow characteristics associated with the valve, thereby adversely influencing the performance of the valve. This is very counter-productive to the clinical needs of the prosthesis. It is very hard to develop a mechanical valve that has the same flow characteristics of a living tissue valve. This is especially so of many existing multi-part prostheses. Even the so-called sutureless valves that have been disclosed in the art may have this problem. Heart valve designs have been directed toward minimizing the back pressure or restriction of forward flow by maximizing the cross-sectional area of the valve within a given outer diameter base. Housing attachment means within the valve base narrows the inside diameter of the valve body thereby creating adverse flow characteristics. Therefore, there is a need for a prosthetic valve which has the flow area thereof maximized. Reduced flow area may also result in rapid blood acceleration with a concomitant risk of red cell hemolysis and activation of sensitive enzyme systems such as the clotting system.

Yet a further problem with some prosthetic heart valves and the implanting procedures associated therewith, is that there are unwanted projections remaining on the implanted valve. This is especially so for valves that are sutured in place. Blood clots tend to form around foreign objects in the body. The body's natural defenses try to seal off any foreign material and make it non-threatening. However, there is a danger that the formed blood clots may dislodge into the patient's blood stream, which may cause a major problem.

The sutures used in many existing techniques to sew a cuff in place are knotted and cut off. This leaves raw edges exposed to the patient's blood stream. These raw edges of the cut off suture and knot provide surfaces for clot formation and provide potential for clots to break off into the bloodstream as they are newly formed. Loose clots in the bloodstream are dangerous for the patient as they have the potential for producing a stroke. Clots forming on sutures may also extend onto the valve and produce malfunctions by trapping the valve open or shut. It is common practice to treat a post-surgical patient with heparin or some other anticoagulant to minimize the production of clots. Therefore, there is a need for a prosthetic valve and surgical implanting process that minimizes the amount of foreign objects that remain exposed to the patient after the valve has been implanted. The exposed surfaces may also become a site of infection. Circulating bacteria may become attached and lead to infection at the valve. These infections are notoriously difficult to treat with antibiotics.

Yet another problem arises because it is difficult to effect a secure fit between the prosthesis and the patient's tissue. If there are gaps between the lumen and the valve, a leak may develop causing blood to bypass the valve. This can cause disastrous problems. Additionally, in many of the prostheses that are disclosed in the prior art as being sutureless, there is no way to ensure close approximation of the aortic lumen to the valve base prior to setting fasteners. This has allowed the lumen to pull away from the base and create the just-mentioned leak-generated problems. This is because anatomy is different from patient to patient. It is impossible to make the entire spectrum of valve bases to accommodate such differences in anatomy as would be required by some of the systems presently in use. Additionally, differences in diameter are not just in diameter of the lumen, but in the irregularities of the annulus where the valve is to be placed. Still further, disease and calcification can make the placement of known valves unmanageable. Whatever the cause of the imperfect fit between the prosthetic valve and the lumen, the variation in opening size and/or shape must be accounted for in placing the prosthesis. A securely anchored and tightly fit prosthesis is necessary for a successful outcome.

Furthermore, an improper fit between the prosthetic device and the lumen may greatly increase the duration of the operation or require corrective surgery to replace an improperly placed prosthesis.

Therefore, there is a need for a prosthesis valve that can be securely fit to a patient's lumen in an expeditious and reliable manner.

While the art contains several teachings which could be applied to one or more of the above-mentioned problems, such as the above-discussed cuffs, these disclosures have several drawbacks which are in addition to those already mentioned. For example, these prosthetic valves generally include a sewing ring or suture cuff that has some sort of stiffener therein. An example of such a stiffener is soft plastic. Plastic, even easily molded plastic, may require the patient's tissue to be severely handled and still have puckering even after great precautions have been taken. In this situation, stiffening elements may be more difficult to handle than fully flexible elements and may adversely affect the patient's tissue. Therefore, any new prosthesis valve should use a fully flexible material to attach that prosthesis to the patient to avoid the problems of unduly stressing the patient's tissue during the placement of the valve.

Dacron, Polyester and Teflon have been a very popular material for sewing cuffs. It is slightly stretchable, allowing it to be dilated. Needless readily pass through it without tearing or snagging the fabric fibers and the Dacron material has exceptional implant qualities with a proven track record of bioacceptance that allows ingrowth of endothelial cells. Due to its wide acceptance, it will be commercially advantageous to incorporate Dacron into any new prosthesis valve.

Therefore, there is a need for a prosthesis heart valve which can be tightly placed in a patient without requiring undue stressing of the patient's tissue.

There is yet additional need for a prosthesis heart valve which can have its size and shape expeditiously adjusted to produce a secure, non-leaking, fit to the particular patient, again without placing undue stress on the patient's tissue.

Still further, it is highly desirable for the surgeon to be able to adjust the orientation of the valve in situ. This will permit the prosthesis to be customized to the particular patient. While many known valves can be moved in place, there is still need for improvement in the ease and accuracy of such a step.

Still further, because the position of the junction between the coronary arteries and the aorta is variable, the choice of the location of the placement of the prosthesis should be as great as possible. The high profile of many of the finished sewing cuffs of the known devices severely limit this choice.

Still further, in many instances, it is advantageous for the surgeon to move the prosthesis into various positions relative to the sewing cuff. This will allow the valve to sit at the same level, above or below a certain level. For example, it might be advantageous to seat the valve cuff to be seated above the annulus to maximize the effective orifice area. It will be advantageous to be able to place the prosthesis in the most superior position without interference with the coronary arteries thereby allowing a larger diameter prosthesis to be placed. A lower profile cuff allows the surgeon to place the prosthesis as high as possible without interfering with the coronary artery junction.

Therefore, there is a need for a prosthetic heart valve that has a low profile finished cuff whereby the surgeon can have a greater choice in the superior/inferior placement of the prosthesis valve.

Current prosthetic valves are inefficient because the sewing cuff occupies part of the area available for flow through the valve. If a very small prosthesis is placed in the annulus, there can be a mismatch between the patient's cardiopulmonary requirements and the flow area of the valve. If a patient demands a high level of flow due to a larger size, a small sized valve may result in a significant transvalvular gradient. That is, the pressure in the left ventricle is considerably higher than the pressure in the aorta. This results in increased work for the left ventricular muscle and may predispose to myocardial failure.

If the surgeon suspects that the prosthesis placed is going to be too small, he may elect to enlarge the aortic root. Presently, this is accomplished by opening the aortic annulus opened perpendicular to the plane of the annulus in continuity to the aortomy. The incision is extended along the anterior leaflet of the mitral valve for a varying length. A patch of tissue or fabric material is then stitched to this incision to enlarge it. The procedure allows the insertion of a larger prosthesis into the newly enlarged annulus. However, there is an increased risk to the patient, principally because of the risk of bleeding from the suture line. This site is virtually inaccessible to repair after the aorta is closed.

Therefore, there is a need for a simpler way to expand the aortic annulus. Dilation is preferred, and thus, there is a further need to be able to expand the aortic annulus by dilation.

Still further, in minimally invasive surgery, it is sometimes difficult to gain access to a proper fastening plane with a straight instrument. Therefore, it is desirable to be able to use an articulated or curved shaft for a fastening or stapling instrument. Still further, it is often desirable to be able to manipulate the fastening instrument into the most advantageous orientation with respect to the area being stapled.

Therefore, there is a need for a fastening instrument that can be operated to gain access to a great number of fastening planes.

Still further, it is often desirable to stretch and manipulate an element prior to fastening that element to the patient. This is not always possible in minimally invasive techniques using instruments that are available prior to the instruments disclosed herein. Therefore, there is a need for an instrument that can stretch and shape a flexible element prior to and during fastening of that element to a patient in a minimally invasive procedure.

Still further, tough tissue, calcium deposits and the like make fastening an element to a patient difficult, especially in the context of a minimally invasive technique. Therefore, there is need for an instrument that can force a staple through tough tissue and/or calcium covered tissue in a minimally invasive technique. This should be achieved without bunching or damaging the tissue or the element being stapled.

Often, in minimally invasive surgery, it is difficult to place staples in precisely proper locations. This is especially true if the staples are being placed in a circular pattern. Since the circumference of a circle is often not evenly divisible by the width of a staple the gaps between staples are often difficult to establish with proper accuracy so gaps in the staple coverage or bunching of either tissue or material is avoided.

Therefore, there is a need for a device that can be used in minimally invasive surgery for properly placing staples.

Staple placement can be effected by manually locating the staple delivery assembly or by automatically locating the staple delivery assembly. If a manual location technique is used, it is desirable that the surgeon be given an opportunity to choose. between a manufacturer's suggestion and his own assessment of the situation. Therefore there is a need for a stapling device for use in minimally invasive surgery that will allow a surgeon to manually locate staples or to select a suggested location for the staples.

As above discussed, the placement of staples in a minimally invasive situation may be difficult to effect in an even manner. Therefore, there is a need for a means and a method for placing staples in a pattern wherein the spacing of the staples is even and no overlap or unwanted gaps occur even if an aorta or other such organ being stapled is an "off size."

bbb.

Still further, it is desirable that a staple used in a minimally invasive surgical technique drive through the tissue and the material being attached to the tissue in a manner that is most effective. Thus, no bunching or gaping should occur, even if the tissue is tough. The effort to drive the staple through the tissue should be minimized if possible since the mechanical advantage is not the most effective in many situations.

Therefore, there is a need for a staple that can be used in a minimally invasive surgical technique that can be driven through tough tissue in an effective manner.

Still further, there is a need to close the aortomy after completion of valve replacement surgery. This is now achieved using sutures. However, this is time consuming. Therefore, there is a need for a means and a method for closing the aortomy in an efficient and effective manner.

The previous co-pending patent applications, the disclosures of which are incorporated herein by reference, disclose novel ways to attach heart valve prostheses into human tissue. The present disclosure deals with more specific areas of the actual fasteners and fastener deployment mechanisms for accomplishing the fastening methods. As can be appreciated by the teaching of these and this disclosure, the invention is much more than merely a fastener type or delivery device. The invention pertains more broadly to a methodology and system for stretching the prosthesis and annulus, providing a flexible prosthesis anchoring ring and means and devices for deploying the fasteners and fastening the prosthesis to the tissue.

The fasteners disclosed in the co-pending applications are fasteners which are formed using a stationary anvil system and a moving driver system both of which are located on the same side of the prosthesis being attached to the patient, and more specifically, inside the prosthesis and the vessel or on the same operative side of the tissue. The need for this type of same-side positioning can be understood from the teaching of the incorporated material.

In the case of mitral valve repair, there is no ready access to the back side of the valve which is in a separate chamber of the heart. Moreover, there are more problems besides access that prevent help from outside the lumen in a fastener forming process. For example, consider the aortic valve. The annulus of the valve sits at the exit of the left ventricle. The coronary arteries of the heart (left and right) are above the annulus. In addition, the aortic annulus is below the junction of the vessel wall with the myocardium. To gain access to the back of the annulus, it is required to incise the epicardium. To further complicate matters, the AV node is very close to the aortic annulus.

If one tries to deploy a prosthesis fastening device that uses an outside anvil or support for forming the fasteners, one encounters many anatomical and surgical problems. First, for example, the surgeon would have to dissect the coronary arteries from the bed of the heart in order to "clear" a space below the coronaries to place such a helping tool. This alone would take an enormous amount of time and could be very risky. Then, dissection must proceed into the heart muscle in order to obtain direct opposition from within the lowest (inferior) portion of the aortic annulus. Therefore, to have a backing device on the outside of the annulus one must dissect into the myocardium. This would then risk intrusion into the AV node and create a very weak area of the heart which would need surgical closure when the outside component is removed.

In addition to the above-mentioned anatomical problems, there are numerous problems associated with mechanics of aligning a fastener pusher with a forming device located remotely. The tolerances required for alignment are very tight in order of only a few thousandths of an inch outside of which the proper fastener form will not be generated. Compound this with having to split or cantilever a forming member to get it around or under the dissected coronary arteries and it presents a truly monumental task. To further complicate this arrangement as the aorta or lumen size changes the corresponding outside forming member must accommodate these sizes. This would present a serious problem requiring many different size devices to accommodate varying sizes of human anatomy. Note also that in some cases, such as AAA procedures, there will be no way to access the outside of the lumen, so the very nature of the procedure requires that the delivery of fasteners be restricted to the inside of the lumen. Thus, prior art devices, other than the incorporated devices, have significant drawbacks.

Furthermore, fatigue resistance is an important factor that should be considered in placing a prosthesis into a patient, especially if the prosthesis will be exposed to blood flow in a heart. Fluid hammer can create significant forces on the prosthesis and any fasteners used to attach it to the patient. If such forces are not properly accounted for, problems can arise. Therefore, there is a need for a fastener placement system that can place fasteners in a manner so that fluid hammer and/or fatigue will not create significant problems for the prosthesis.

OBJECTS OF THE INVENTION

It a main object of the present invention is to provide a prosthesis heart valve which can be implanted in a surgical procedure that is minimally invasive.

It is another object of the present invention to provide a prosthesis heart valve that can be implanted in an expeditious surgical procedure.

It is another object of the present invention to provide a prosthesis heart valve that can present the largest possible flow area to the patient.

It is another object of the present invention to provide a prosthesis heart valve that reduces the number of objects exposed to the patient after implantation.

It is another object of the present invention to provide a prosthesis heart valve which can be customized to the particular patient without placing undue stress on the patient's tissue.

It is another object of the present invention to provide a prosthesis heart valve which can utilize widely accepted materials while still realizing the advantages set forth herein.

It is another object of the present invention to provide a prosthesis heart valve which utilizes a fully flexible sewing cuff.

It is another object of the present invention to provide a prosthesis heart-valve which can use a Dacron sewing cuff.

It is another object of the present invention to provide a prosthesis heart valve which has a finished cuff that has a low profile above the valve.

It is another object of the present invention to provide a prosthesis heart valve which eliminates suturing as a means for attaching the prosthetic device to the patient.

It is another object of the present invention to provide a surgical technique associated with the implanting of a prosthesis heart valve which is minimally invasive.

It is another object of the present invention to provide a surgical technique associated with the implanting of a prosthesis heart valve which is minimally invasive yet which is accurate, expeditious and results in a firmly, accurately and fixedly placed prosthetic device.

It is another object of the present invention to provide a surgical technique associated with the implanting of a prosthesis heart valve which reduces the amount of stress that is placed on the patient's tissue during the placement procedure.

It is another object of the present invention to provide a surgical technique associated with the implanting of a prosthesis heart valve which does not require opening the patient's chest wall.

It is another object of the present invention to provide a surgical technique associated with the implanting of a prosthesis heart valve which attaches the prosthesis valve with fasteners that are hidden inside the device whereby the chances of infection and thrombosis are significantly reduced.

It is a specific object of the present invention to provide a surgical technique associated with the implanting of a prosthesis heart valve which hides the fasteners inside the sewing cuff.

It is a specific object of the present invention to provide a surgical technique associated with the implanting of a prosthesis heart valve which significantly reduces the chances of the cuff puckering during the implanting procedure.

It is another specific object of the present invention to provide a surgical technique associated with the implanting of a prosthesis heart valve which dilates the graft or cuff and the lumen together to provide intimate contact during the fastening procedure.

It is another object of the present invention to provide a surgical technique associated with the implanting of a prosthesis heart valve which allows for endoscopic visualization of the placement of the valve in the heart.

It is another object of the present invention to provide a surgical technique associated with the implanting of a prosthesis heart valve which permits both dilation and placement of fasteners in a sewing ring or graft.

It is another object of the present invention to provide a surgical technique associated with the implanting of a prosthesis heart valve which assures secure attachment of the prosthetic device to the patient.

It is another object of the present invention to permit a surgeon to use a larger valve if such larger valve is indicated.

It is another object of the present invention to provide a means and method wherein the annulus of the aorta can be stretched as a prosthetic valve is being placed.

It is another object of the present invention to allow insertion of a larger prosthesis without opening the annulus and adding a patch.

It is another object of the present invention to provide a means and a method whereby annuloplasty can be performed.

It is another object of the present invention to provide a device that will allow the addition of standard sutures to repair or reinforce any area of potentially weak attachment of the suture ring to the annulus.

It is another object of the present invention to provide a means and a method for minimally invasive surgery which can gain at access to a proper fastening plane.

It is another object of the present invention to provide a means and a method for minimally invasive surgery is able to manipulate the fastening instrument into the most advantageous orientation with respect to the area being stapled.

It is another object of the present invention to provide a means and a method for minimally invasive surgery which can stretch and manipulate an element prior to fastening that element to the patient.

It is another object of the present invention to provide a means and a method for minimally invasive surgery that can force a staple through tough tissue and/or calcium covered tissue in a minimally invasive technique without bunching or damaging the tissue or the element being stapled.

It is another object of the present invention to provide a means and a method for minimally invasive surgery for properly placing staples.

It is another object of the present invention to provide a means and a method for minimally invasive surgery that will allow a surgeon to manually locate staples or to select a suggested location for the staples.

It is another object of the present invention to provide a means and a method for minimally invasive surgery that includes a staple that can be used in a minimally invasive surgical technique that can be driven through tough tissue in an effective manner.

It is another object of the present invention to provide a means and a method for minimally invasive surgery for closing an aortomy in an efficient and effective manner.

It is another object of the present invention to provide a fastener that is self forming, that is a fastener that does not need an anvil to secure it to a patient's tissue.

It is another object of the present invention to provide a fastener that is protected from fluid hammer.

It is another object of the present invention to provide a fastener that can attach a prosthesis to a patient in a manner such that the deleterious effects of fastener fatigue are minimized.

It is another object of the present invention to provide a fastener that can be used to attach a prosthesis to a patient in a manner such that the deleterious effects of a failure of one fastener are minimized.

It is another object of the present invention to provide a fastener that can be placed, will approximate tissue, and cinch that tissue all when controlled only from one side of the tissue.

It is another object of the present invention to provide a prosthesis fastening system which fastens a flexible prosthesis to human tissue which is resistant to the deleterious effects of fatigue.

It is another object of the present invention to provide a prosthesis fastening system which fastens a flexible prosthesis to human tissue which has shock absorbing qualities of a non-rigid assembly.

It is another object of the present invention to provide a method to attach a fully flexible prosthesis to tissue with a segmented array of fasteners whereby delivery of the fasteners is accomplished entirely from one side of the tissue.

It is another object of the present invention to provide a prosthesis fastening system which utilizes a segmented array of fasteners which allows for the expansion of the aorta during insertion of the prosthesis in heart surgery, It is another object of the present invention to provide a prosthesis fastening system which utilizes a fastening element which can grow with the tissue.

It is another object of the present invention to provide a prosthesis fastening system which utilizes spring-loaded fasteners.

It is another object of the present invention to provide a prosthesis fastening system that utilizes barbed fasteners.

It is another object of the present invention to provide a prosthesis fastening system that utilizes fasteners that are rotationally delivered.

It is another object of the present invention to provide a prosthesis fastening system which utilizes a segmented array of fasteners which allows the prosthesis to be flexible, moving in unison to the pulsating nature of heart tissue loading to resist fatigue of the fasteners used in heart surgery.

It is another object of the present invention to provide a prosthesis fastening system with the ability to install a fully flexible and expandable anchoring system which pre-stretches the aorta lumen tissue in heart surgery thereby permitting larger diameter valve to be inserted than is practical with prior art techniques.

It is another object of the present invention to provide a heart valve prosthesis fastening system with a means of fastening the heart prosthesis all from within a lumen.

It is another object of the present invention to provide a prosthesis fastening system which utilizes a fastening means whereby the fasteners are all hidden from a blood path in heart surgery.

SUMMARY OF THE INVENTION

These, and other, objects are achieved by a sutureless prosthetic heart valve or graft which has a flexible sewing cuff stapled in place prior to placement of the heart valve body. The objects are also achieved by a fastener and a tool and a surgical procedure for effecting placement of the prosthetic valve in a minimally invasive manner.

More specifically, the prosthetic valve includes a flexible sewing cuff, such as Dacron, or the like, which is stapled to heart tissue using a special tool that is inserted into the patient via an incision located in the thorax, either via a retrostenal approach or by removal or separation of the ribs. The tool releasably carries the cuff and includes means for continuously pressing the flexible cuff against the patient's tissue during the stapling procedure whereby the cuff is deformed rather than the tissue and puckering is essentially eliminated.

The cuff is attached to the valve body using drawstrings which extend outside the patient's body. The valve body is positioned in the in-situ cuff and the drawstrings are operated. Because the cuff is flexible, stretching of the tissue is minimized since inaccuracies are, at least, partially, absorbed by the flexible cuff.

The system disclosed herein should have improved blood flow and biological acceptance in the patient because suture knots and felt pledgets are not used. This provides additional advantages to use of this system due to a potentially reduced risk of stroke and infection post-surgery and potential for use of lower doses of anticoagulant and antibiotics post surgery.

Still further, due to the minimally invasive nature of the procedure, there is a possibility of applying the teachings of this invention to emergency procedures that may be performed outside of an operating room environment.

Yet another advantage of the present system is the low profile of the finished cuff above the valve base. This allows the surgeon greater choice in the superior/inferior placement of the valve. This is important because the position where the coronary arteries join the aorta is extremely variable. The low profile of the cuff allows for more distance between the cuff and the coronary junction.

Because the cuff of the present device is formed of material that has already been successful and is widely accepted, the commercial advantages associated with this device are enhanced.

Due to the surgical techniques that can be utilized with the present invention, it is possible to use video appliances, such as miniature video endoscopes.

One feature of the present invention is that of fatigue resistance. In mechanical systems which are subjected to repeated impact or other non-uniform loading, one needs to design for fatigue resistance. Just as a wire rope is more fatigue resistant than a single rod, the inventors have taken the approach that multiple small fasteners joined by a flexible member are much better suited to handling repeated loading of heart pulsation.

In the inventive system, each individual fastener will see only its local loading. Each fastener is isolated from adjacent fasteners. Therefore loading on one fastener does not influence the adjacent fasteners with bending moments. The flexing which causes fatigue will happen between each fastener thereby substantially reducing flexural loading on individual fasteners, thereby greatly reducing the chances of flex fatigue.

More specifically, the inventive system provides the extra security of having many fasteners in place and the redundancy to back up a failure of any one fastener. Additionally, since individual fasteners make up a peripheral plurality of attachment sites, small gaps between adjacent fasteners are desirable to allow the aortic wall to relax after insertion of a prosthesis in heart surgery through normal growth of minor tissue trauma incidents which will allow for an anchor ring and valve to essentially "sway with the breeze," but not become dislodged or leak. The inventive system takes multiple "bites" of tissue to build each on the other to create a chain of fasteners that each has a positive grip on the area to tissue within each fastener.

The fastener system of the present invention has several features that permits it to overcome the above-discussed problems and to achieve the above-stated objectives: a plurality of fastening elements spaced in a staggered but uniform pattern; the fastening elements are applied from inside the lumen only without the aid of external anvils or supports; the fasteners penetrate both the prosthesis and the tissue thereby approximating the prosthesis and the tissue at the individual fastening element; and the individual fastening elements can be placed in a pattern that allows the lumen and the prosthesis to flex without compromising hemostasis or security.

The presently disclosed means and method can be used to perform annuloplasty where the annuloplasty ring is fastened to an aorta above a leaky but salvageable human tricuspid valve. In this form, an annuloplasty ring would be constructed so the cuff material covers a malleable ring whereby the annuloplasty ring is fastened in place with the disclosed fastener element. The ring could be malleable metal or plastic to allow the surgeon to shape it correctly to impart forces in right area. The malleable ring is then shaped to size or compress the annulus and import a compressive force on the valve causing the leaflets to close more securely. This could be applied to mitral and other locations as well.

The placed cuff can be inspected by the surgeon to be sure that it is placed securely. If the surgeon decides that hand-placed sutures will be helpful, he can place such sutures as needed.

If desirable, the surgeon can use a stable delivery mechanism to place staples either according to a prescribed path or according to his best judgement at the time. The hereinbelow disclosed device includes a staple delivery instrument that can be used to place staples one at a time along a predetermined path, or in conjunction with a guide, automatically along a helical path. The helical path will place staples in a desired spacing and can be used with staples of different widths.

Still further, the device disclosed herein can be used to close an aortomy. If desired, a surgeon can use the staple delivery device to place staples along a path set by icons until he becomes more confident in an automatic placement technique. The instrument saves time in placing staples.

Yet another form of the stapling instrument delivers staples in staggered rows while being able to engage a cuff to force and stretch that cuff against the patient's tissue to ensure proper placement of the cuff.

BRIEF DESCRIPTION OF THE DRAWING FIGURES

FIG. 3 is a sectional view of a sutureless cuff used in the present invention when the cuff has been stapled to the patient and prior to placement of the prosthetic valve body.

FIG. 4 is a sectional view of the prosthetic valve of the present invention after the cuff has been stapled in place and after the prosthetic valve body has been placed in the cuff and before the cuff is attached to the valve body.

FIG. 5 is an enlarged sectional view of the sutureless prosthetic heart valve of the present invention with two rows of staples securing the cuff to the patient and the valve base attached to the cuff.

FIGS. 6, 7 and 8 illustrate how the sutureless cuff of the present invention is constructed.

FIGS. 34a–34e and 34a'–34e' show the steps through which a staple according to the present invention follows as it is being forced into and through elements to be stapled.

Figure 35:
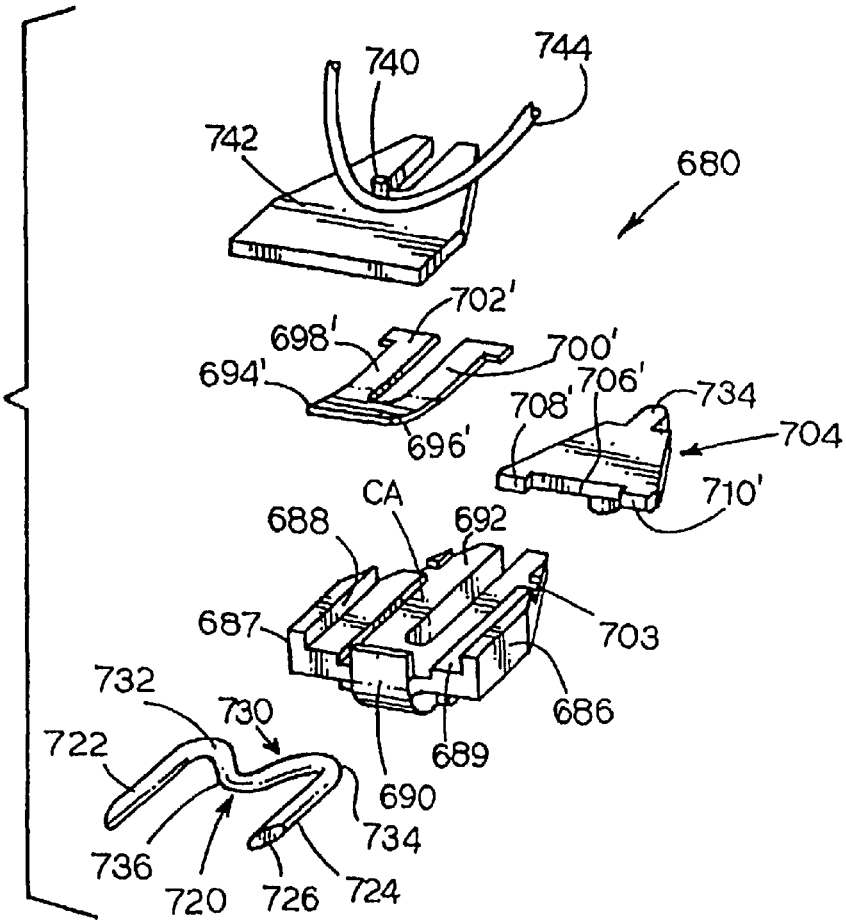

FIG. 35 is an exploded perspective view of another form of staple delivery assembly in which the assembly is returned to an initial position by an elastomeric element.

Figure 36:
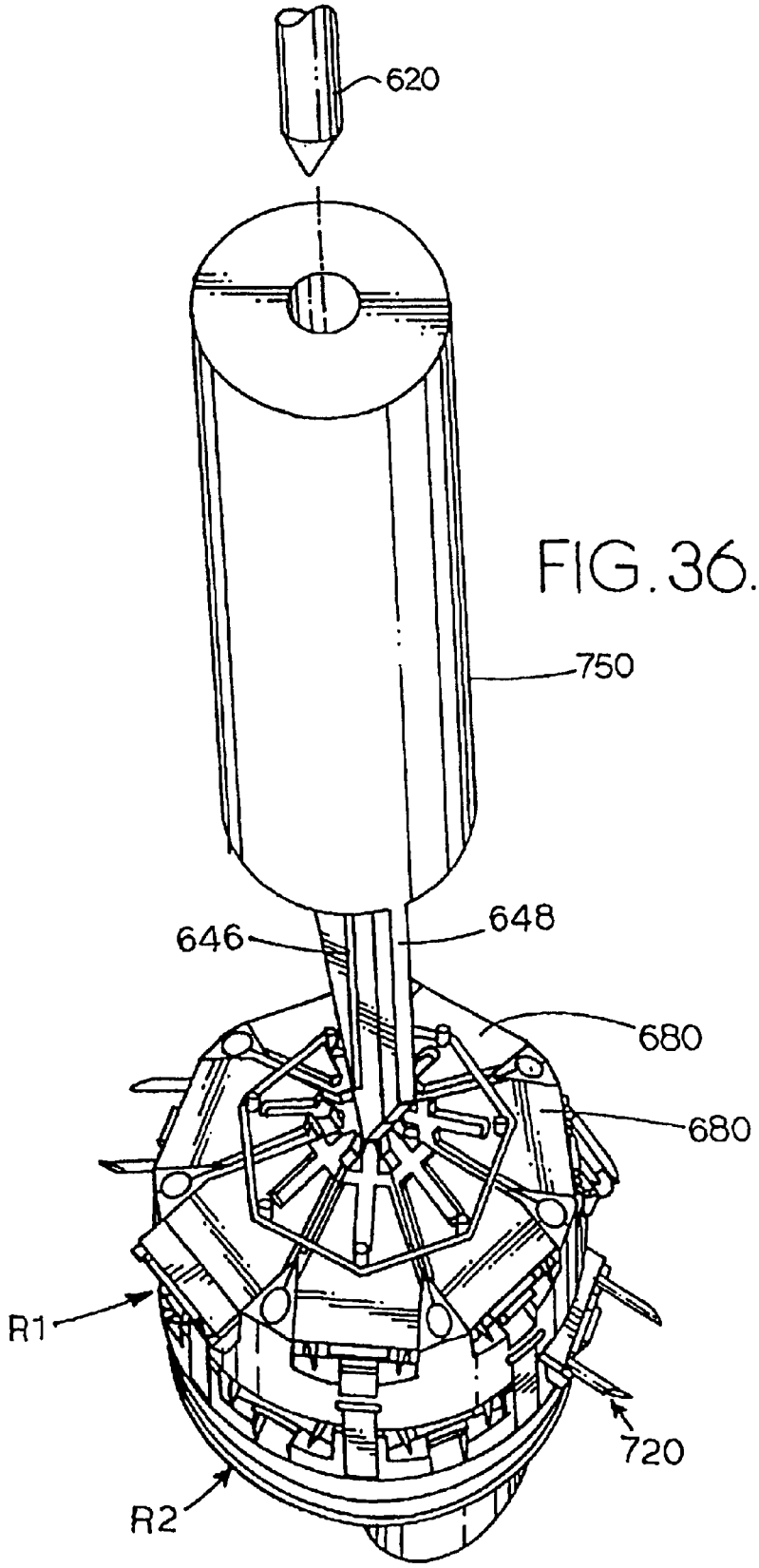

FIG. 36 is a perspective view of another form of staple delivery instrument according to the present invention.

Figure 37:
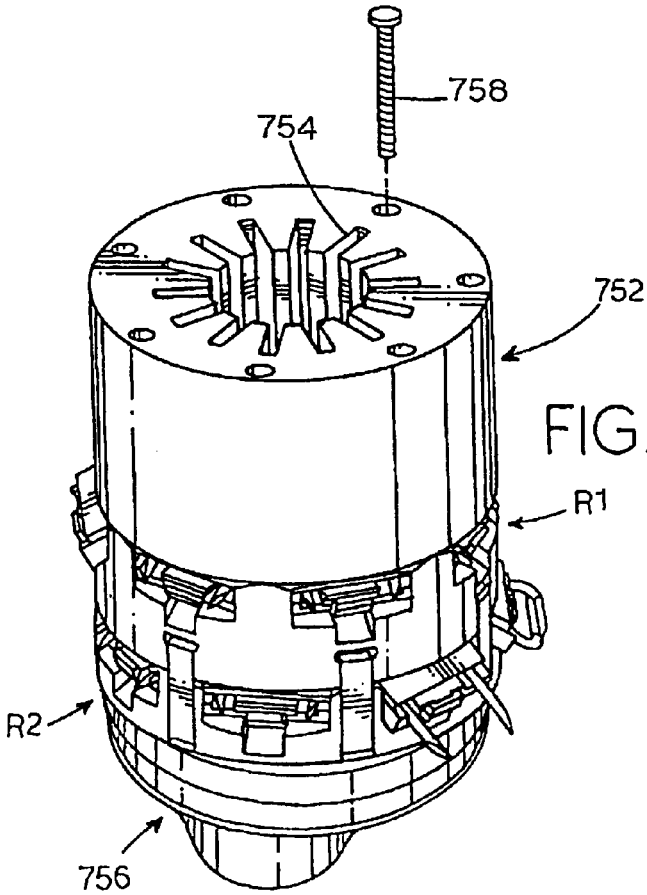

FIG. 37 is a perspective view of a head portion of the staple delivery instrument shown in FIG. 36.

Figure 38:
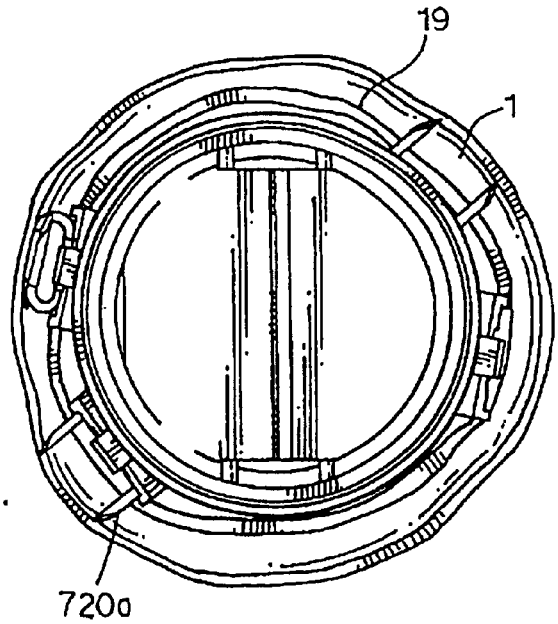
Figure 39B:
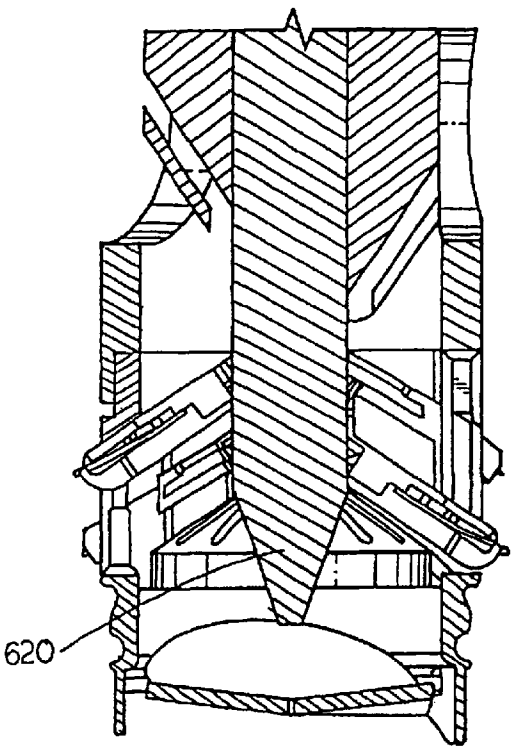
Figure 39A:
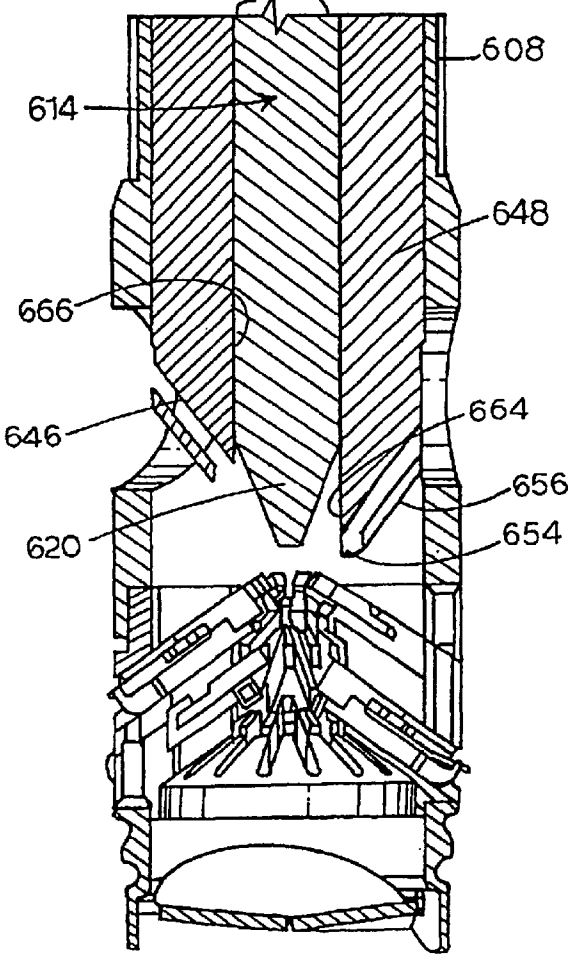
Figure 39D:
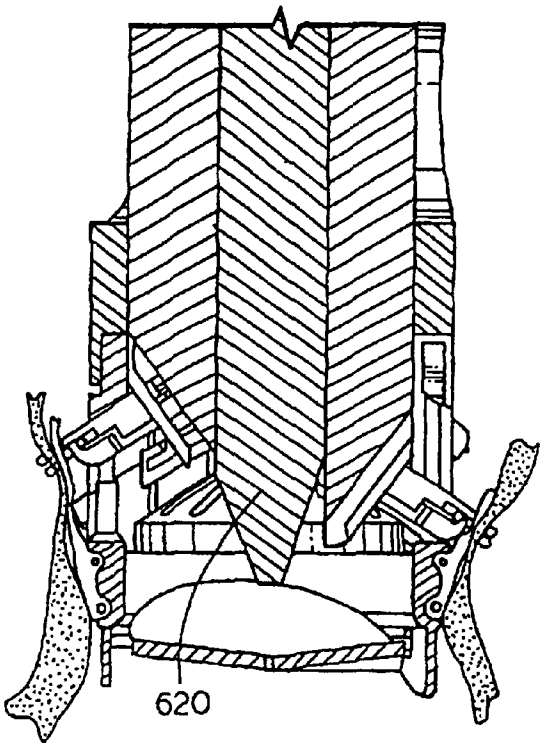
Figure 39C:
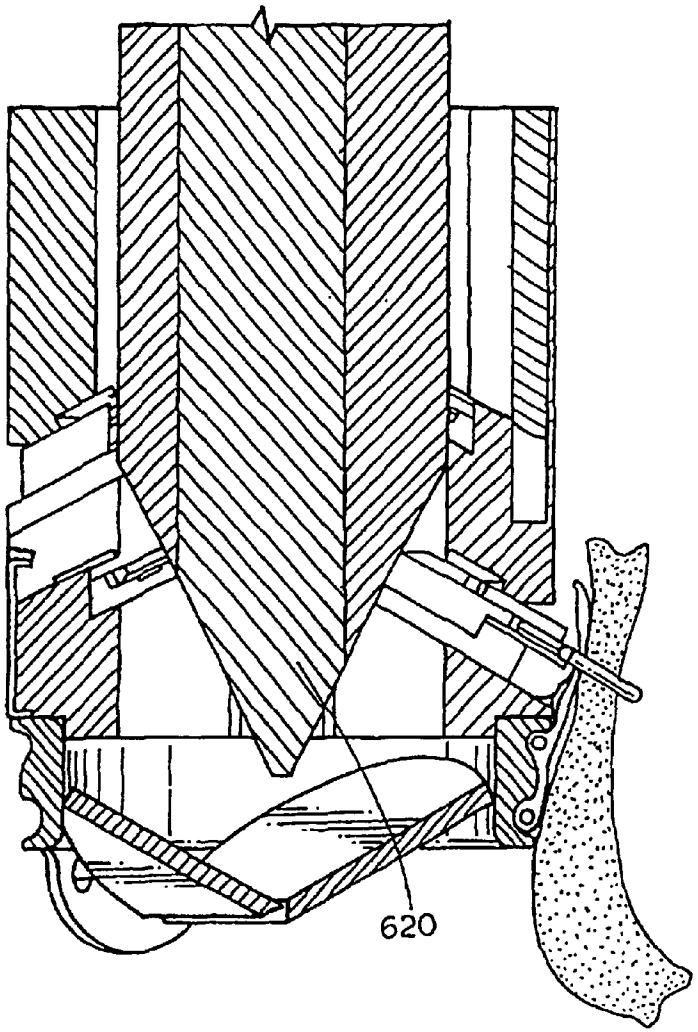

FIG. 38 is a top plan view of an anchor ring in place in an aorta illustrating how the means of the present invention can stretch the ring against the aorta and how the staples of the present invention attach the ring to the aorta.

FIGS. 39a–39d illustrate the operation of the staple delivery instrument shown in FIG. 36.

Figures 40A, 40B, 40C:
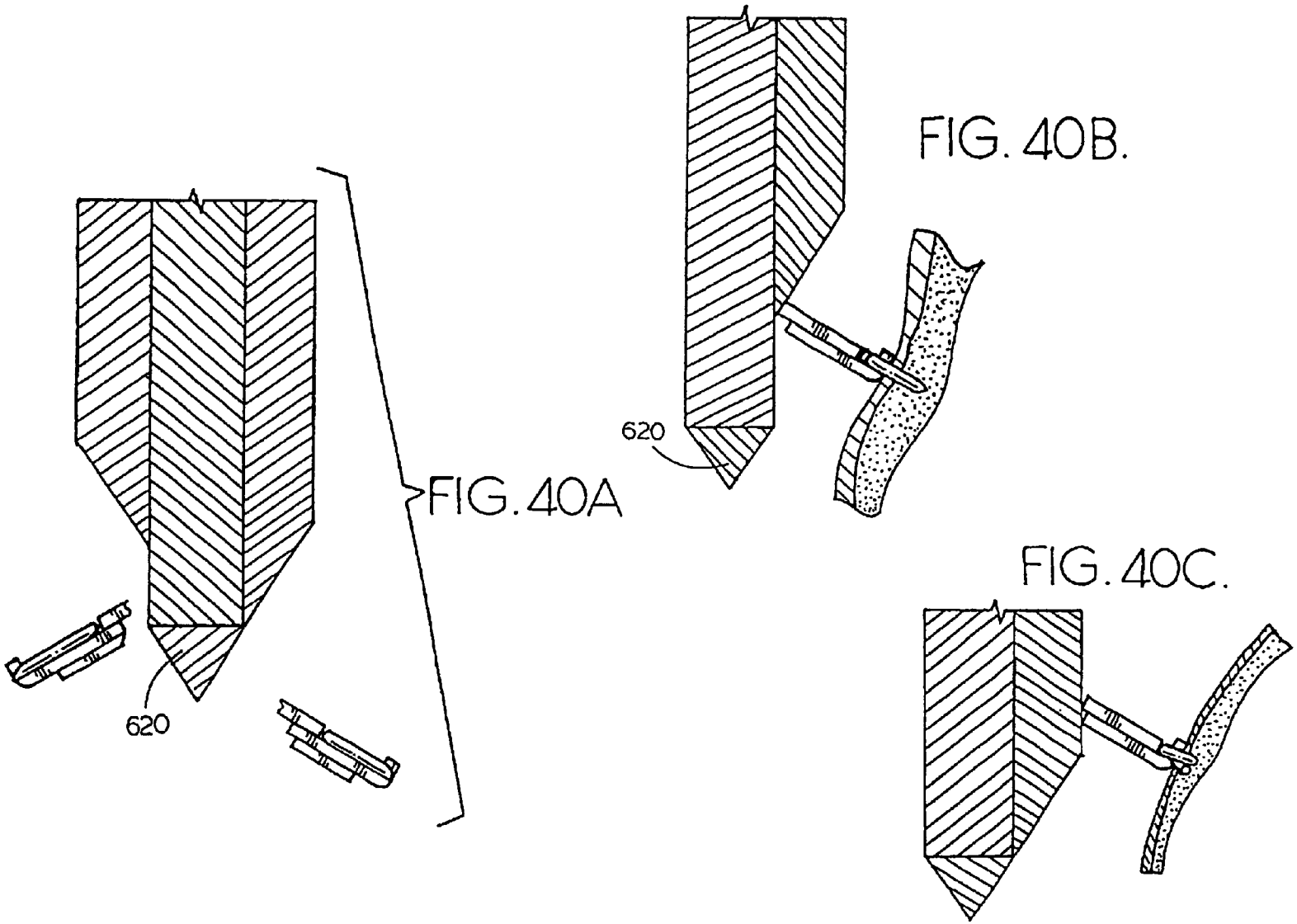

FIGS. 40a–40c further illustrate the operation of the FIG. 36 staple delivery instrument.

Figure 41:
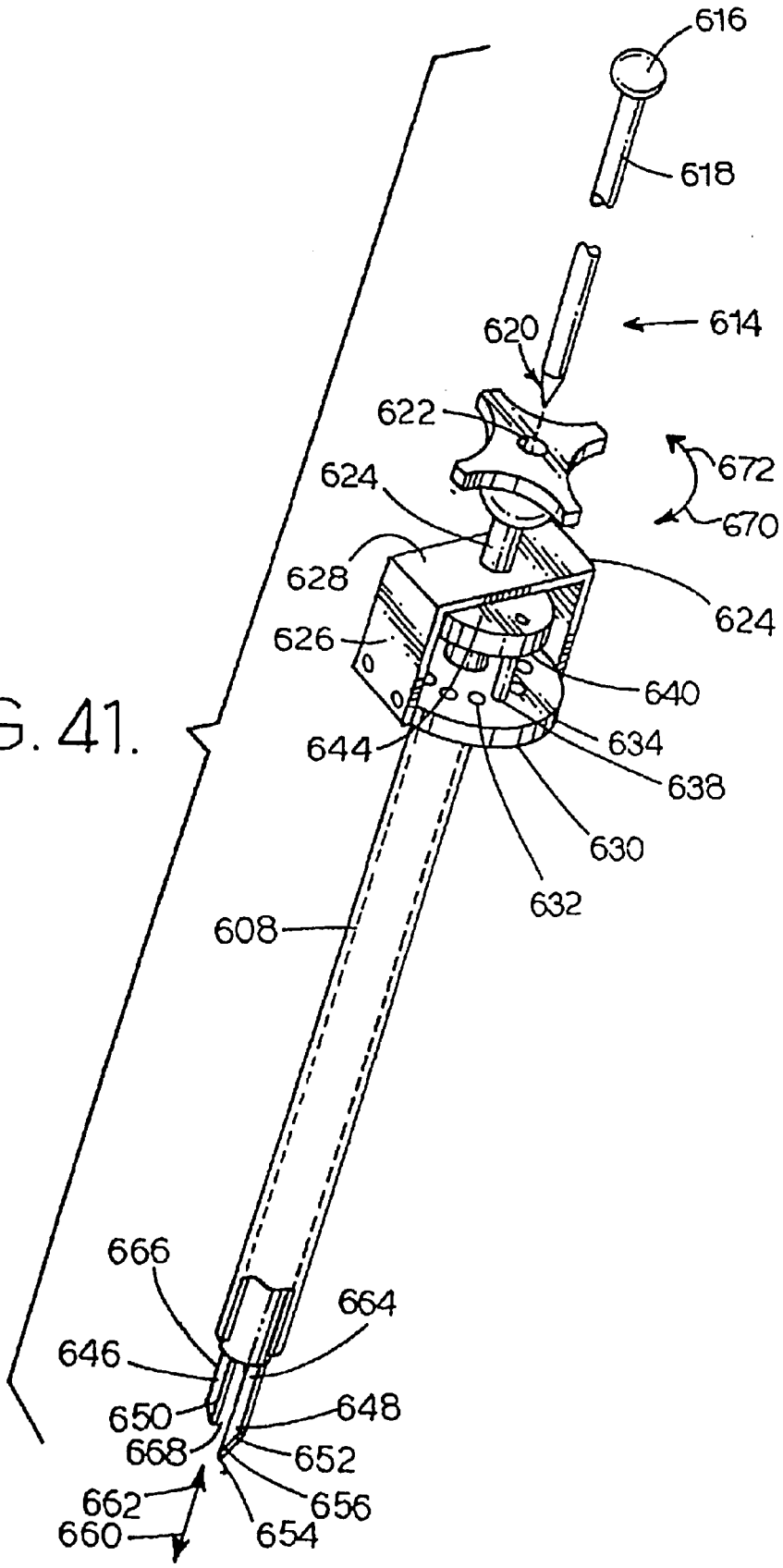

FIG. 41 is a perspective view of another form of a staple delivery instrument.

Figure 42:
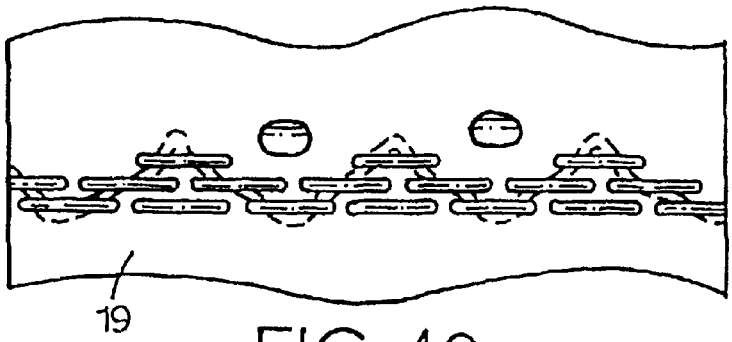

FIG. 42 is staple pattern in a cuff that can be established using the FIG. 41 staple delivery instrument.

Figure 43:
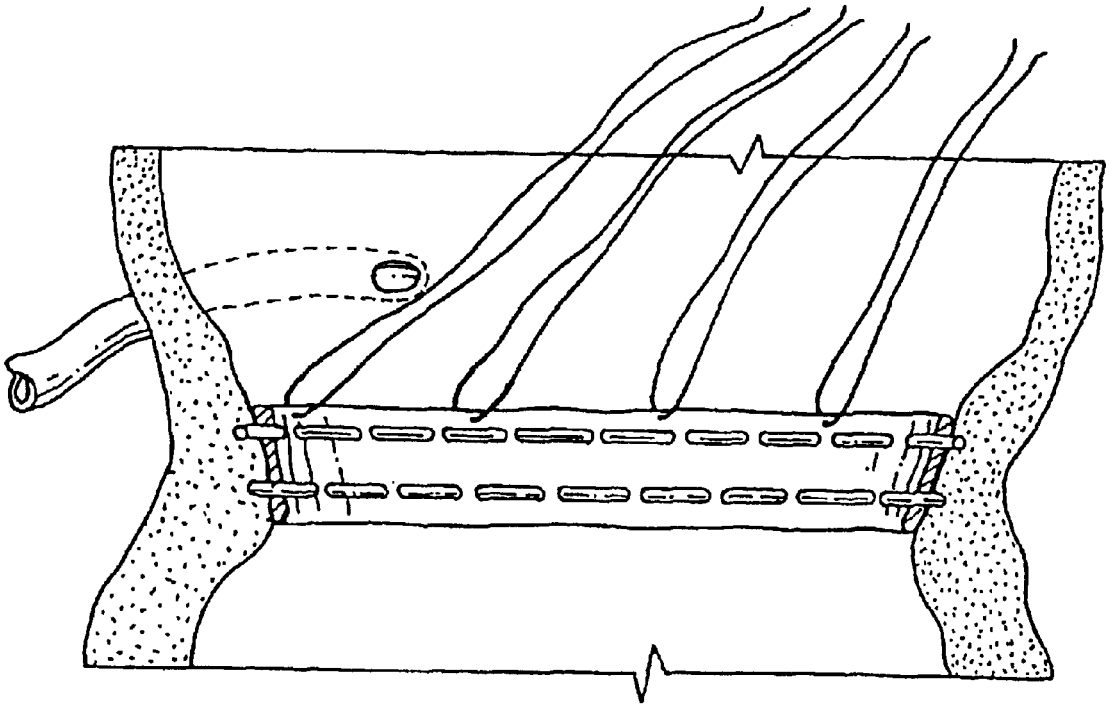
Figure 44:
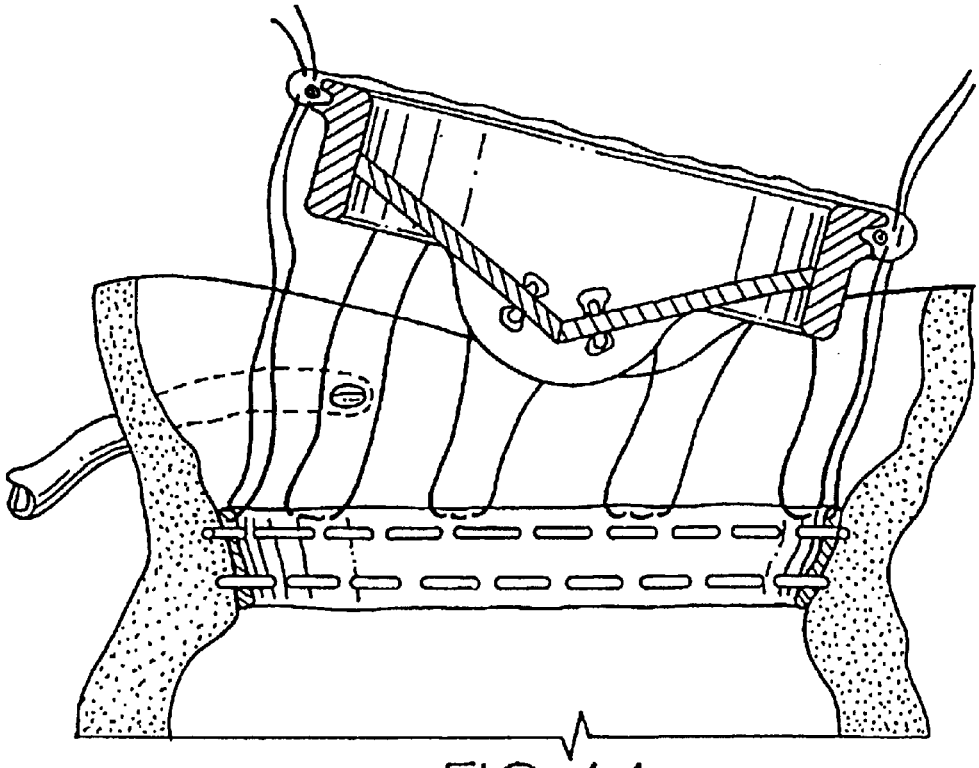
Figure 45:
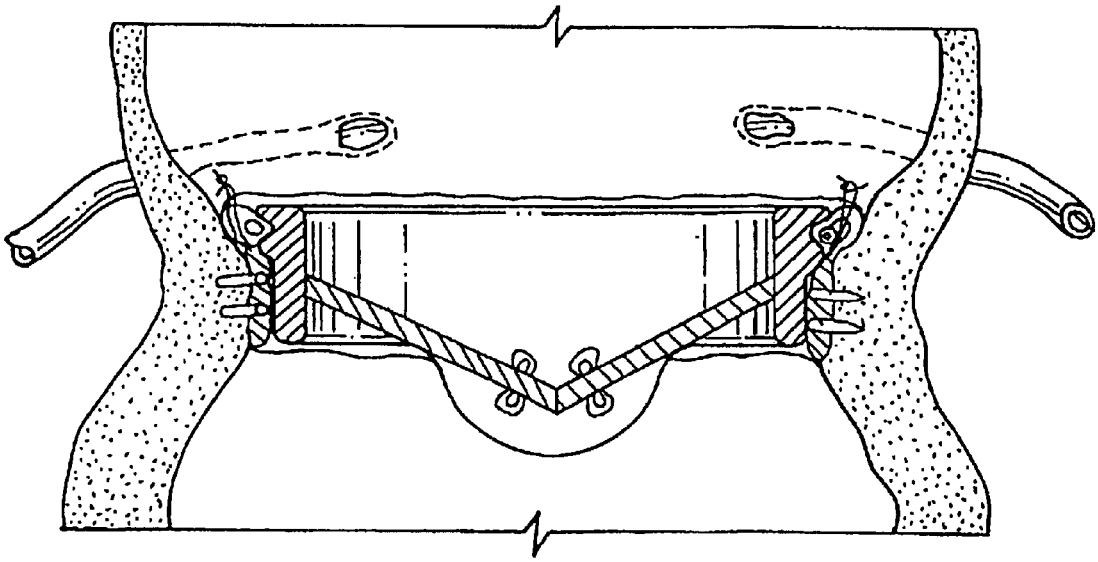

FIGS. 43–45 illustrate the steps in placing a heart valve onto a cuff that has been stapled to a patient's aorta.

Figure 46:
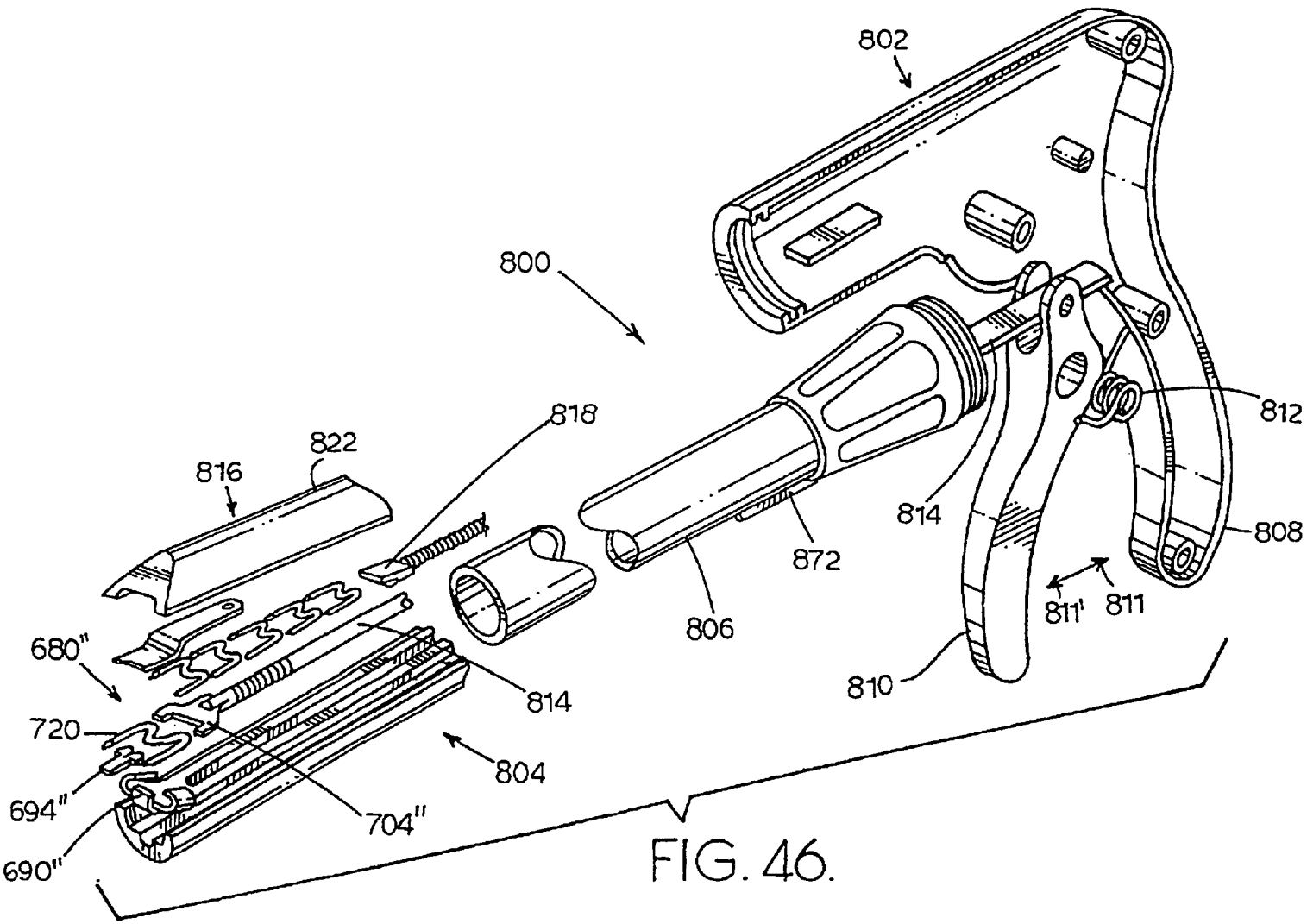

FIG. 46 is perspective of another staple delivery instrument.

Figure 47:
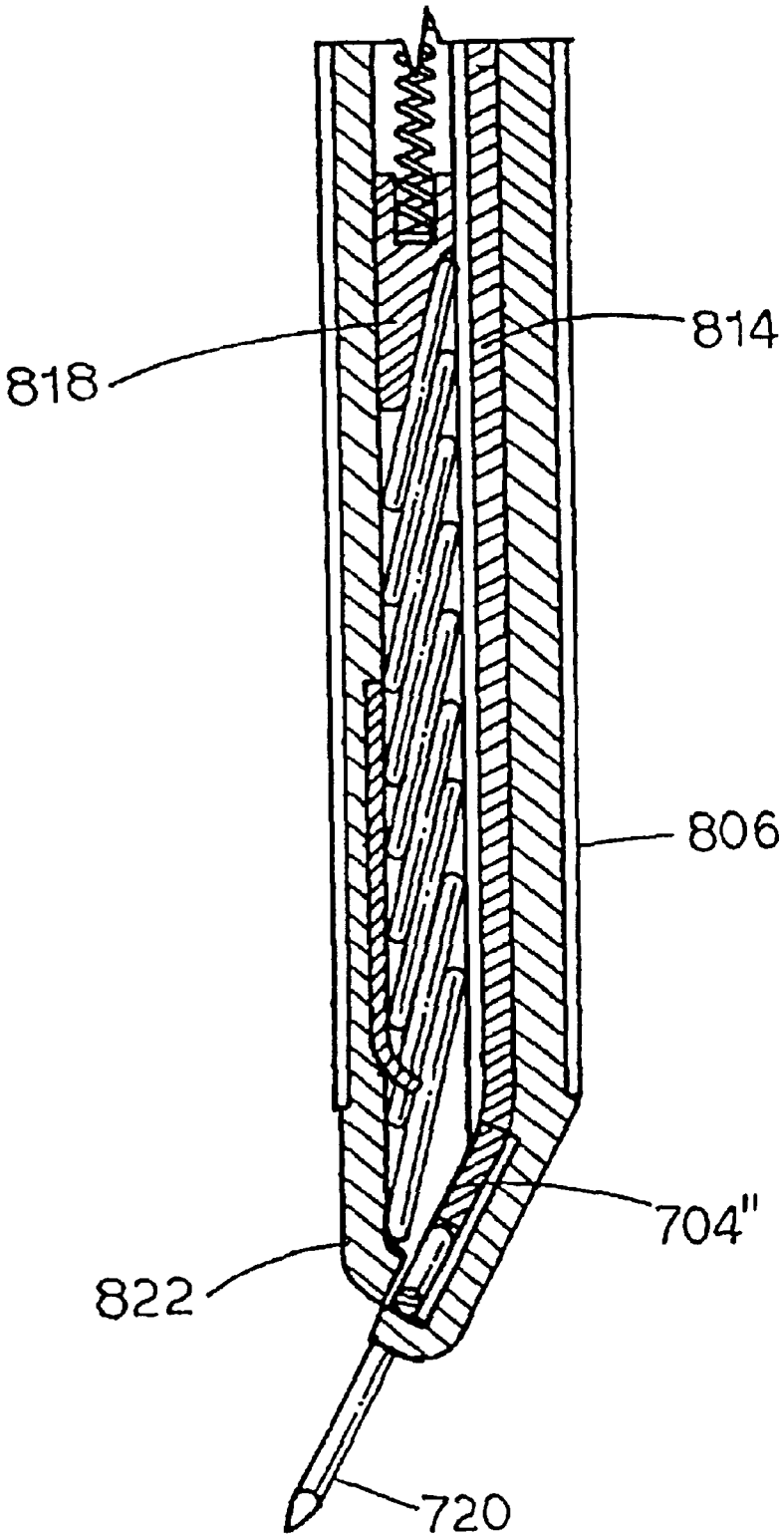

FIG. 47 is partial view of the FIG. 46 instrument illustrating the angled nature of the staple delivery associated with that instrument.

Figure 48:
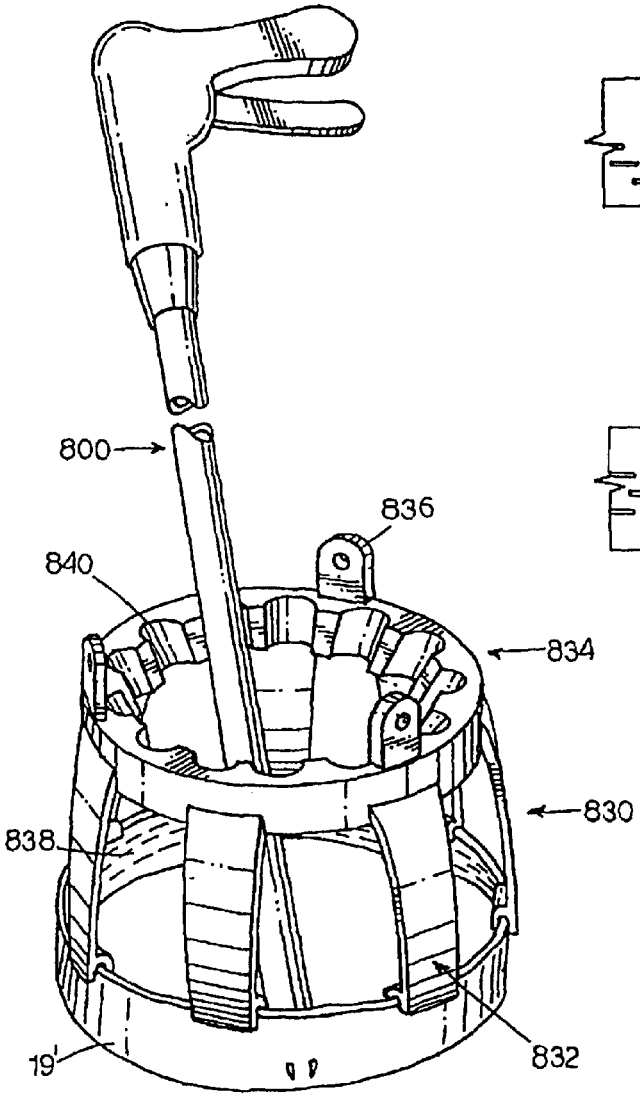

FIG. 48 shows an anchor ring placement element that can be used with the staple delivery instrument shown in FIG. 46.

Figure 49:
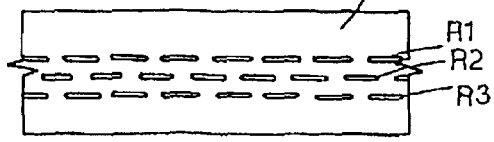

FIG. 49 illustrates multiple rows of staples placed using the staple delivery instrument shown in FIG. 46 and the anchor ring placement element shown in FIG. 48 and following a staple pattern established by icons placed on the anchor ring.

Figure 50A:
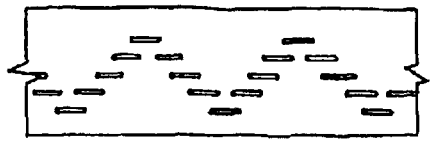

FIG. 50A shows a staple pattern established "on the fly" using the FIG. 46 staple delivery instrument and the FIG. 48 anchor ring placement element.

Figure 51:
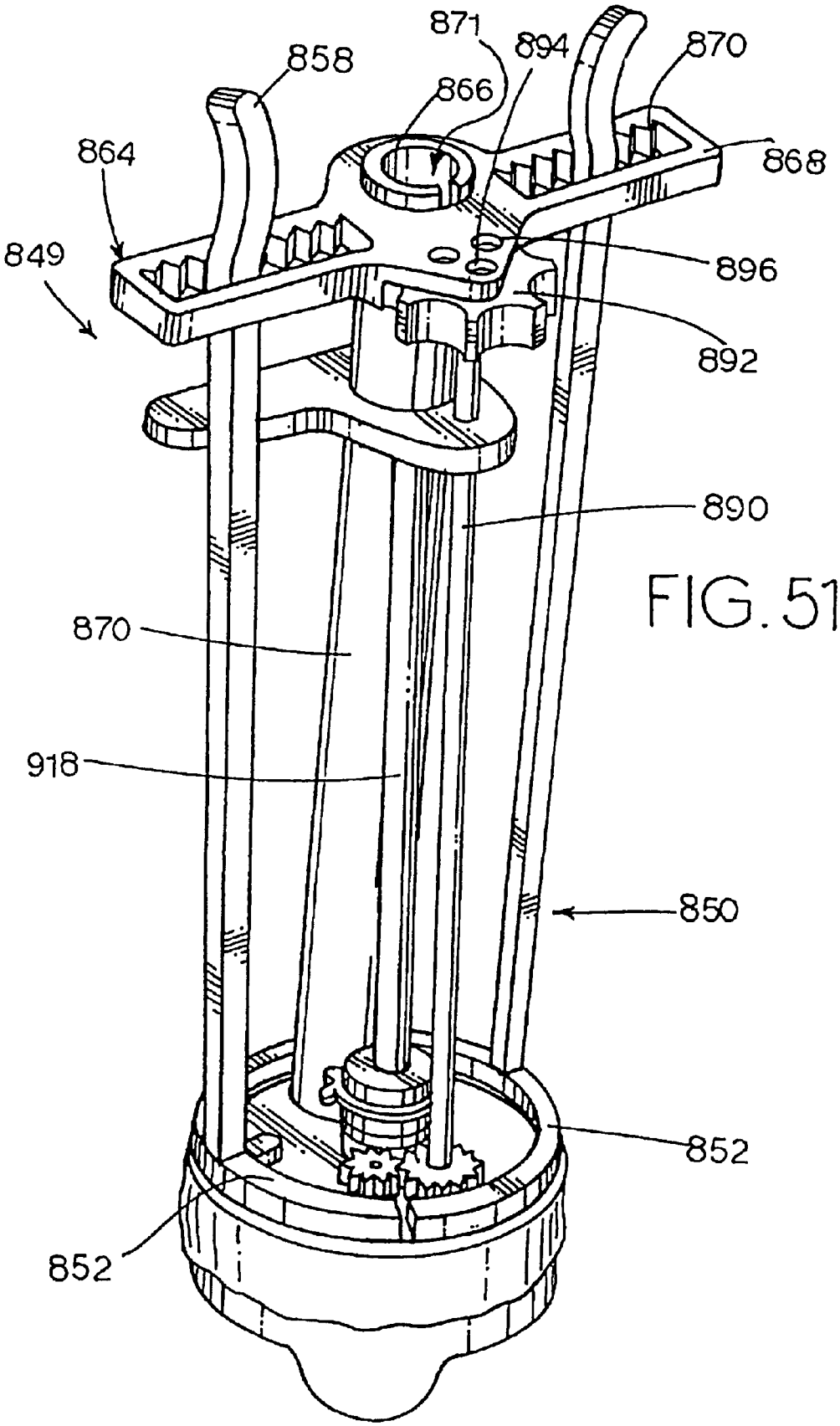

FIG. 51 is a perspective view of an automatic staple placement system that uses the staple delivery instrument shown in FIG. 46.

Figure 52:
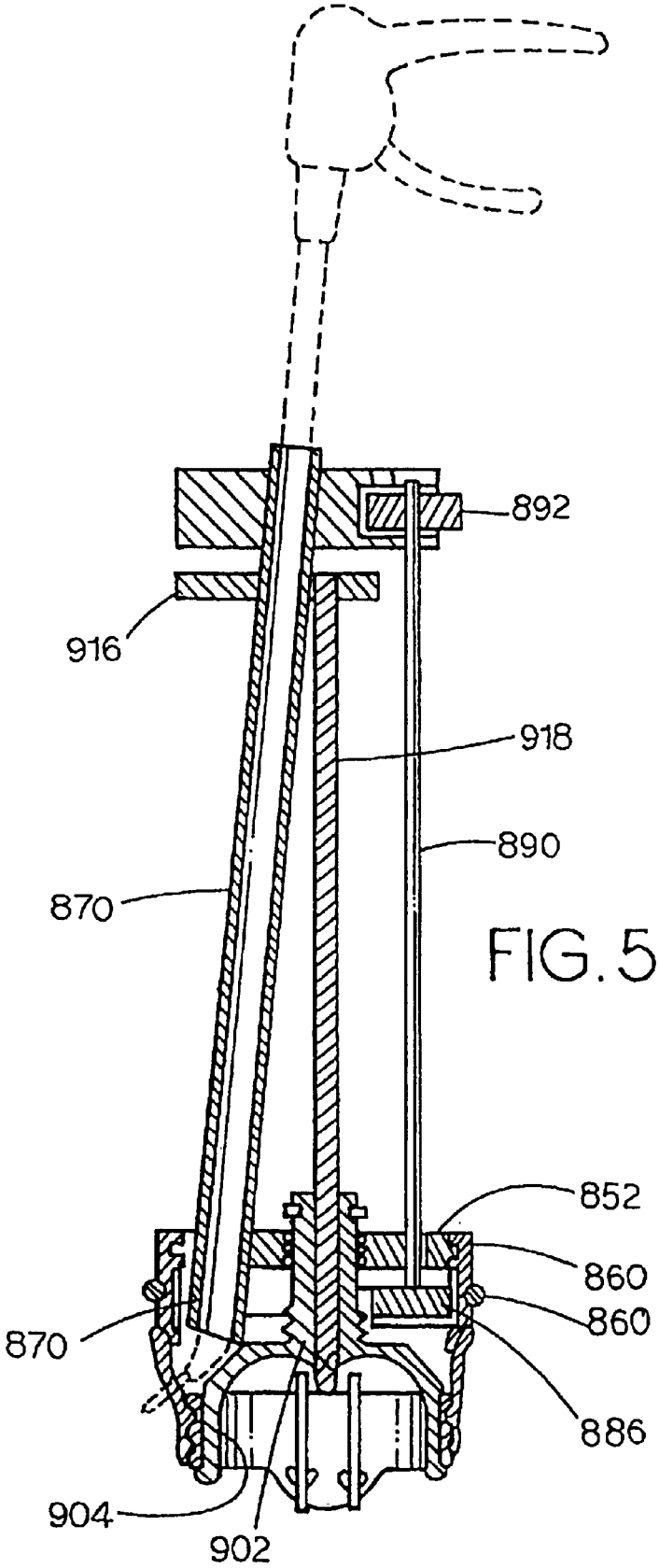

FIG. 52 is an elevational view of the FIG. 51 system showing the FIG. 46 tool in place in the system.

Figure 53:
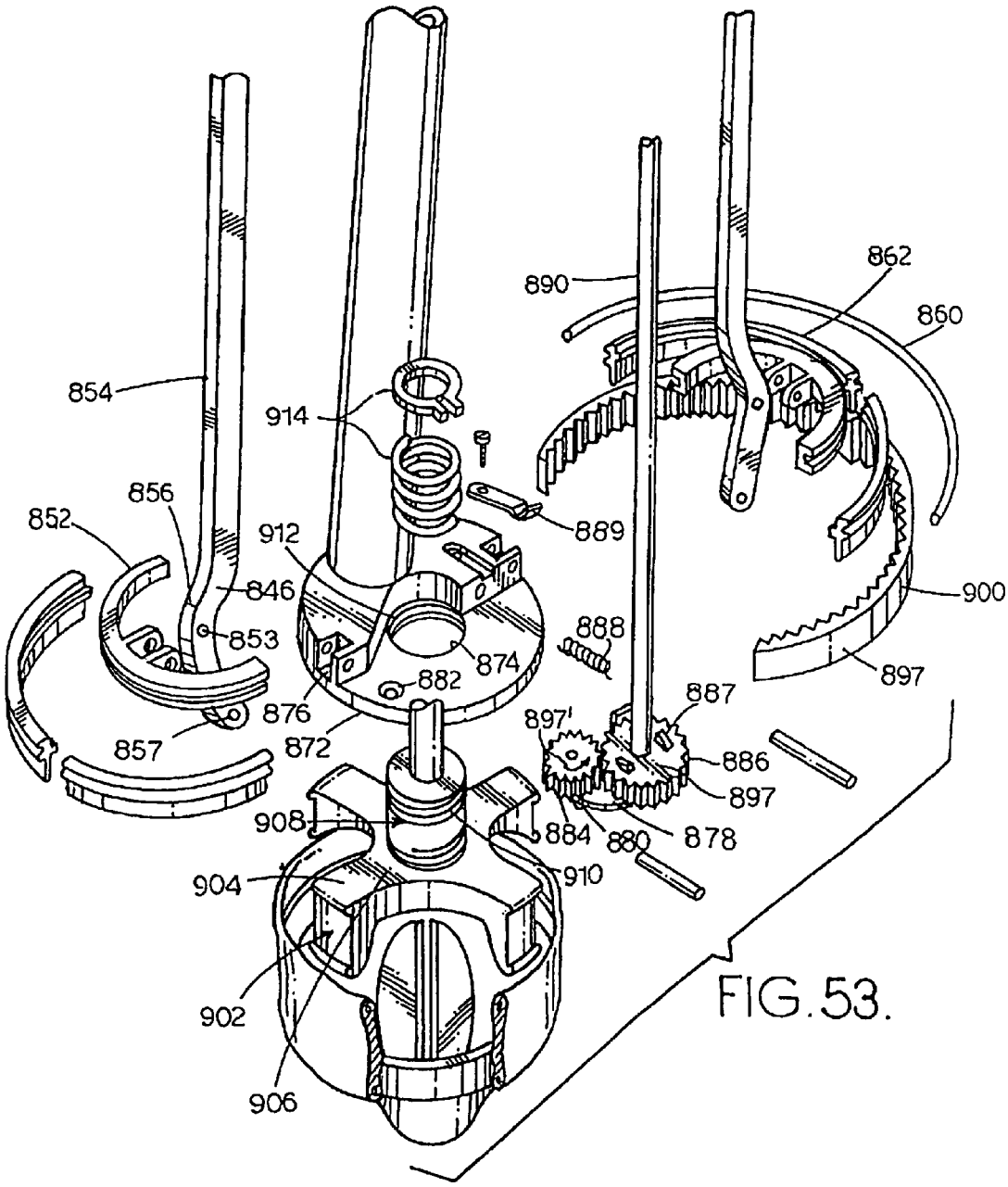

FIG. 53 is an exploded perspective partial view of the FIG. 51 system.

Figure 54A:
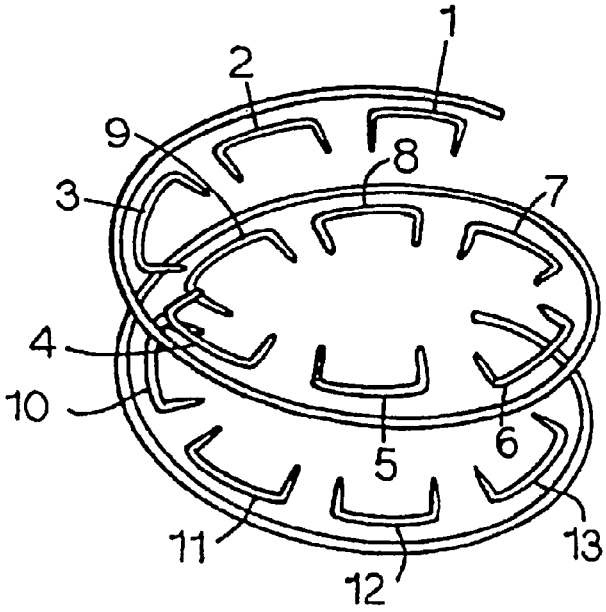
Figure 54B:
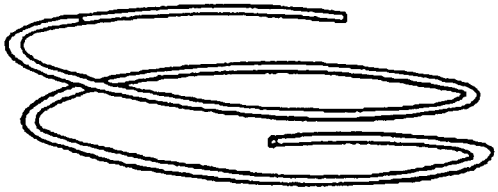
Figure 54C:
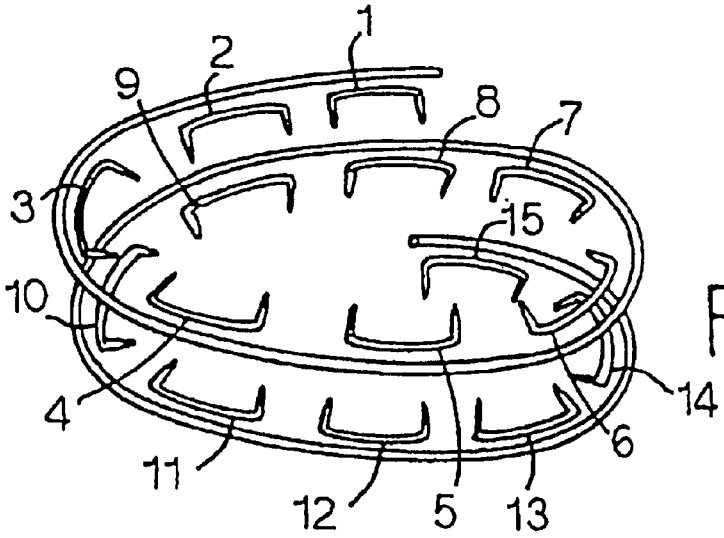

FIGS. 54a–54c illustrate helical staple patterns that are established using the staple system shown in FIG. 51.

Figure 55:
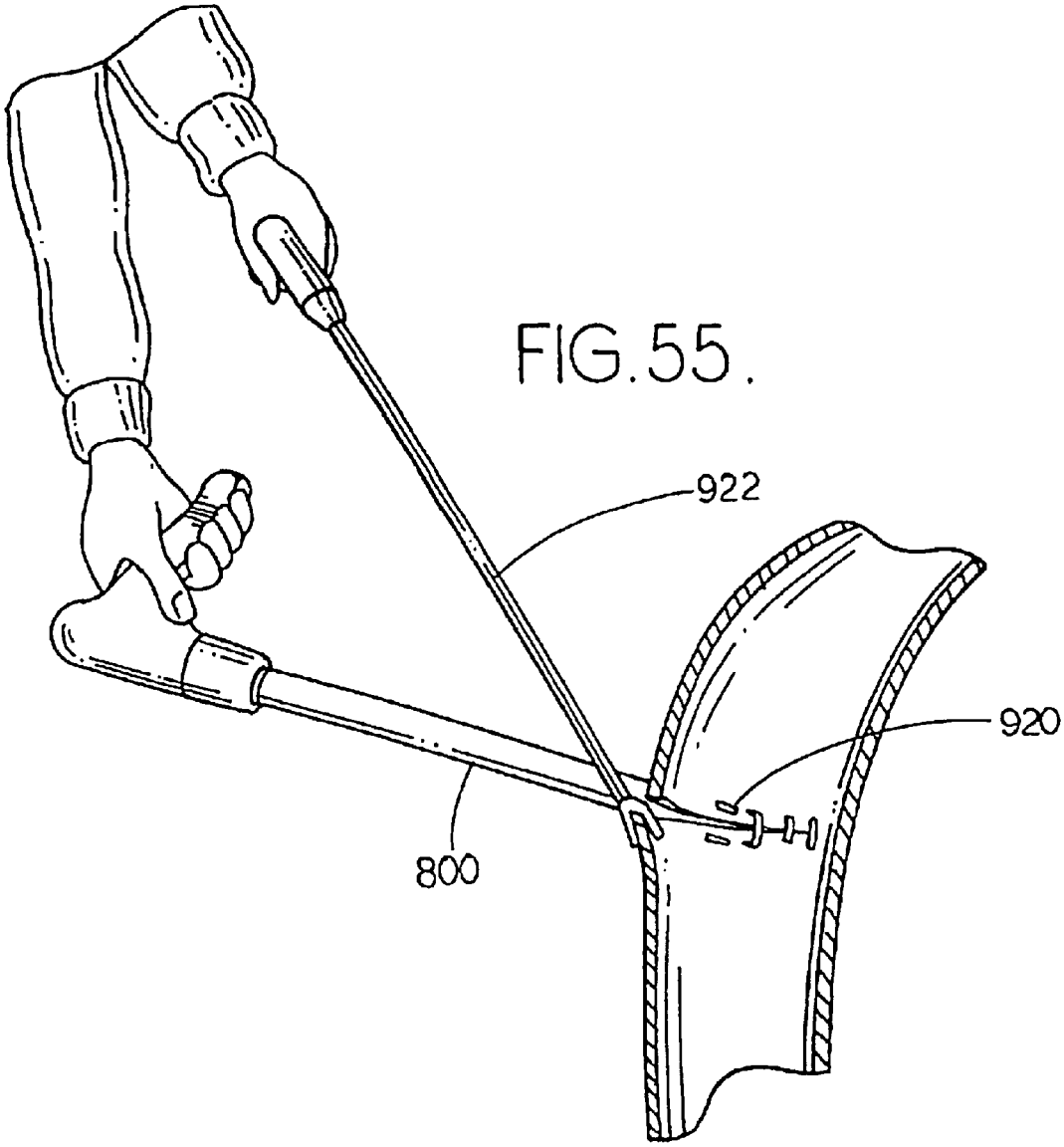

FIG. 55 illustrates the use of the FIG. 46 tool to close an aortomy.

Figure 56:
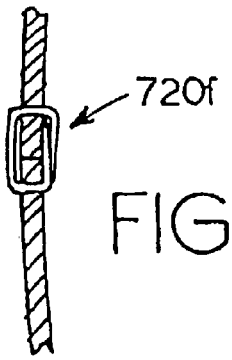

FIG. 56 illustrates the closed aortomy showing how the staple of the present invention brings incised edges together.

Figure 57:
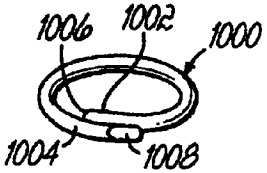

FIG. 57 shows one form of self-forming fastener.

Figure 58:
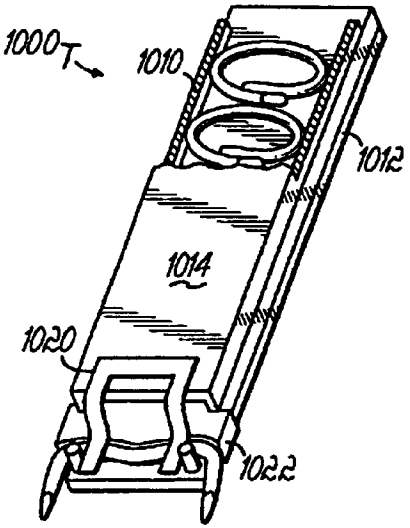

FIG. 58 shows a tool element that can be used in connection with the fastener shown in FIG. 57.

Figure 59:
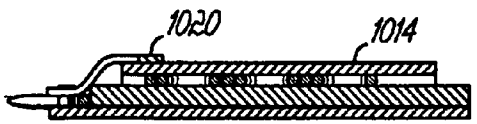

FIG. 59 is a side elevational view of the element shown in FIG. 58.

Figure 60:
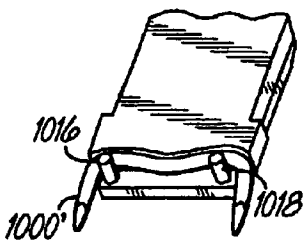

FIG. 60 shows an end of the FIG. 58 element.

Figure 61:
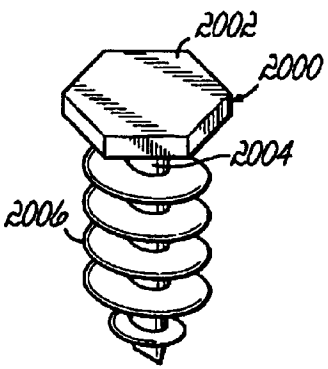

FIG. 61 shows another form of self-forming fastener.

Figure 62:
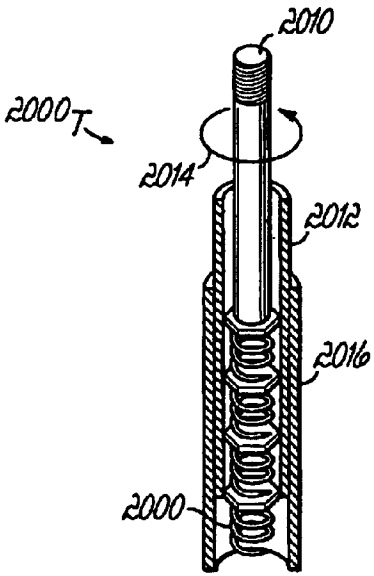

FIG. 62 shows a tool element which can be used to place the fastener shown in FIG. 61.

Figure 63:
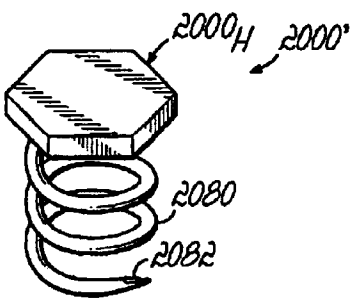

FIG. 63 shows another form of self-forming fastener.

FIG. 64 shows another form of self-forming fastener.

FIG. 65 shows another form of self-forming fastener.

FIG. 66 shows another form of self-forming fastener.

FIG. 67 shows a tool element that can be used to place the self-forming fasteners shown in FIGS. 65 and 66.

FIG. 68 shows the FIG. 67 tool element in an assembled condition.

Figure 69:
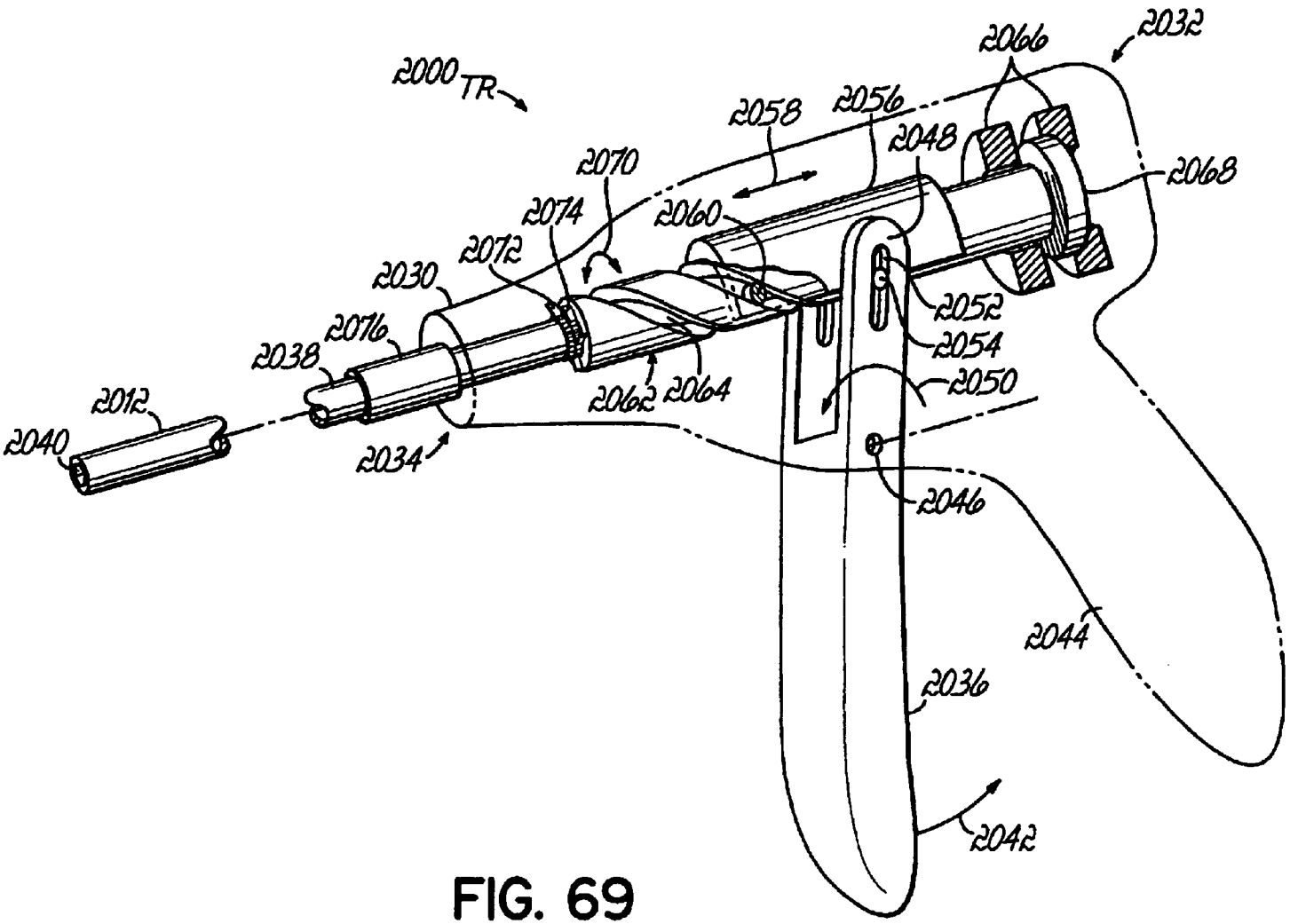

FIG. 69 shows a tool that can be used in connection with the FIG. 62 tool element to place fasteners.

DETAILED DESCRIPTION OF THE PREFERRED EMBODIMENT OF THE INVENTION

The invention is a device and method of fastening an aortic valve prosthesis or vascular graft, into living tissue, particularly suitable for minimally invasive surgery. In the preferred embodiment, the heart valve is separable from its sewing cuff. The valve body has special grooves in its periphery to allow the valve to be attached to the sewing cuff after it has been fastened into the annulus of the patient's aorta. The sewing cuff is specially constructed to provide a means to open up or unfold it and then detachably retain it to the fastener tool to allow for remote attachment of the cuff deep in the aortic lumen. Once the fasteners have been driven and the cuff is securely attached to the aortic annulus, the cuff attachment means is released and the fastener driver tool is removed from the heart. The prosthetic heart valve is then inserted into the aortic lumen and docked to the cuff. A special element is provided between the heart valve body and the cuff to signal to the surgeon when the valve body is properly seated in the in-situ cuff. An annular extension spring provides tension to hold the valve in place. It provides a tactile feedback which indicates to the surgeon that the valve body is securely attached to the cuff. Once the valve body is properly seated in the cuff, the cuff is attached to the valve body with drawstrings or the like. It is noted that while drawstrings are one means for attaching the cuff to the valve body, many other means, such as will be known to those skilled in the art based on this disclosure, can also be used without departing from the scope of this disclosure. Once tightly secured to the valve body, the cuff drawstrings are trimmed thereby completing the installation.

Currently-available valve replacements are hand sewn into the aorta after surgical removal of the defective valve. A critical component of the present invention is that the cuff is fastened to the living tissue with a series of metal fasteners or staples. The staples are arranged in two rows and are staggered to ensure a secure fit between the cuff and the tissue. The fastener driving tool has two stapling mechanisms on two different levels with the staple driving mechanisms on each level being spaced apart by 105° (see FIG. 11). The staples in each row are set two at a time, preferably 180° apart in each row, with both rows being at the same time. The staple mechanisms in one row is off set from the staple mechanisms in the other row. After forming the two sets of opposed fasteners, the attachment tool is rotated. This automatically indexes to the proper fastener offsets to create two staggered rows of fasteners. The offset between staple mechanisms in the two rows is preferably a 30° index and will provide twelve fasteners per row for a 19–21 mm aortic annulus. The fastener driver tool has means to dilate between standard size valve bodies. Thus, the same fastener driving tool can be used on all sizes from 19–23 mm and then the next size up would cover ranges from 23–27 mm, the next 27–32 mm and so forth. This is an important advantage because the surgeon will always want to place the largest body in the cuff. Presently, if a surgeon chooses a 19 mm valve and finds the cuff to be slightly loose in the annulus, it is a major expense to cut loose the 19 mm valve and try again with a 21 mm valve. The fastener driver tool of the present invention may include an indicator that indicates to the surgeon when he is fastening the cuff what size valve the annulus has been stretched to, thus eliminating guesswork.

Figure 1:
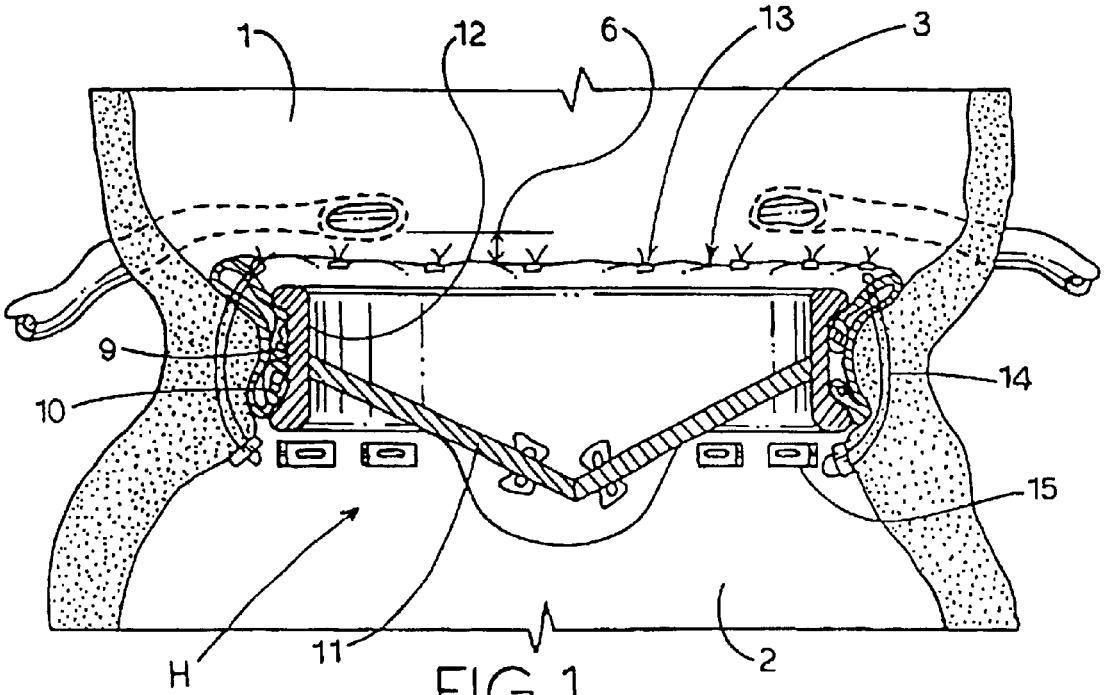
FIG. 1. PRIOR ART
FIG. 1 shows a sectional view of a prior art prosthesis heart valve in place in a patient.

Referring first to FIG. 1, a prior art prosthetic heart valve H is shown installed in the annulus of an aorta 1 next to a left ventricle 2. Valve H is secured in place by a series of sutures 14 which are tied in knots 13. The sutures are most often used with felt pledgets 15 to spread the load of the sutures evenly so as not to tear the tissue. Valve H includes a cuff 3 which is attached to the perimeter of base 12 of valve H in the factory. Drawstrings 9 and 10 are used to effect this attachment. The cuff and valve body are implanted as a single unit with the cuff being hand sewn to the tissue. Leaflets 11 are also shown as is the distance between the top plane of the valve and the right coronary artery junction with the aorta. This distance is indicated in FIG. 1 by numeral 6.

Figure 2:
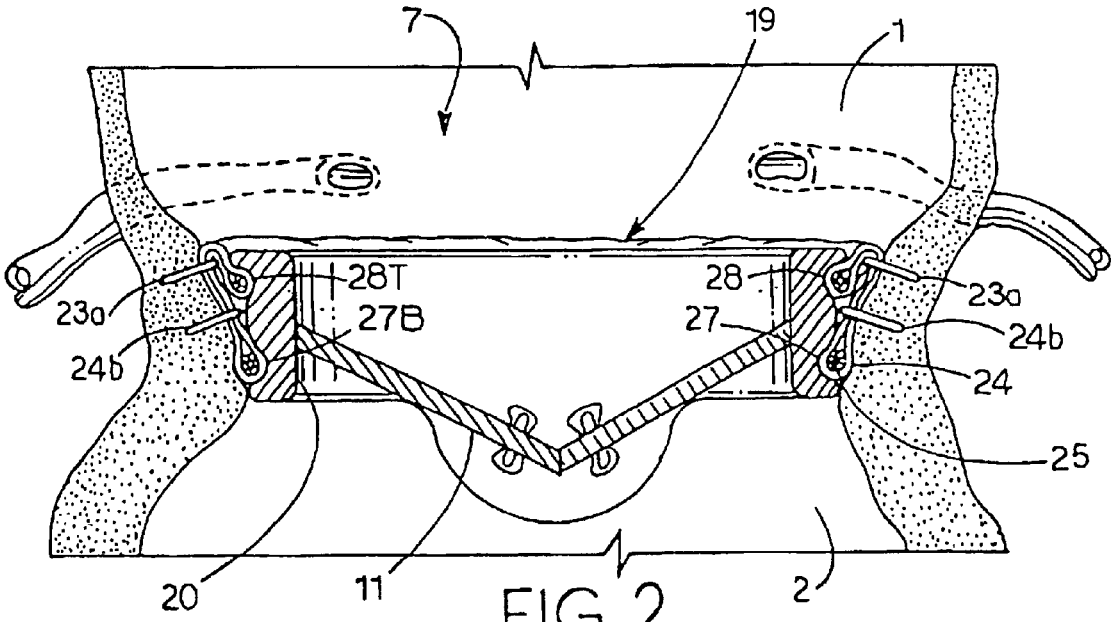
FIG. 2 is a sectional view of the prosthesis valve of the present invention installed in the aortic annulus of a patient.

Shown in FIG. 2 is a prosthetic valve 7 embodying the present invention installed and seated in the annulus of the left ventricle. Fasteners 23a and 24b are used to fasten sewing cuff 19 to the annulus of the aorta. The fasteners are staples in the preferred form of the invention. Drawstrings 27 and 28 are used to secure the cuff to the body 20 of the valve, and an indicating means 25, such as a garter spring or the like, is located in the lower section of the cuff. One form of the indicating means includes a garter spring inside a pocket in the cuff. Indicating means 25 is used to signal the surgeon when the heart valve body 20 has been seated properly in the cuff 19 prior to activating the drawstrings. Contact between means 25 and the valve body provides the surgeon with a tactile signal that the valve body is properly seated in the in-situ cuff.

As can be seen by comparing FIGS. 1 and 2, prosthetic device 7 has no sutures, no pledgets and will be installed as two parts—the cuff followed by the body; whereas, device H has sutures 14, pledgets 15 and is installed as a single unit. However, as can also be seen, the cuff in both instances is still securely connected to the valve body and the cuff can remain a flexible material, such as Dacron or the like whereby the surgeon will still be able to use familiar material. As will be discussed below, the cuff 19 is totally flexible so it can be deformed to fit the aorta rather than requiring the aorta to be deformed to fit the valve as is the case with the valve shown in FIG. 1. Still further, the fully flexible nature of the cuff 19 permits easy deformation of the cuff and thus significantly reduces stress on the tissue surrounding the prosthesis. Still further, the fully flexible nature of cuff 19 permits it to be pressed against the tissue at all times during the installation process so the chance of puckering or paravalvular leak paths is significantly reduced, if not completely eliminated. Using staples in place of the hand-set sutures of the prior art will, as will be understood from the present disclosure, permit the installation of valve 7 using a surgical technique that is minimally invasive.

Cuff 19 is shown in place in the aorta prior to placement of the valve body in FIG. 3. Fasteners 23a and 24b are shown in two rows, with staples in one row being offset from corresponding staples in the other row. Thus, for example, staple 23a' in the top row corresponds to staple 24b' in the bottom row. The staggered nature of the staples in the two rows causes the cuff to be set by a continuous set of staples if the two rows are viewed together. That is, there is some portion of a fastener connecting the cuff to the tissue everywhere in the 360° of the circumference of the cuff. The two rows of staggered fasteners thus forms a means for connecting of the cuff to the tissue in a continuous manner about the entire perimeter of the cuff, and eliminates leak paths.

As shown in FIG. 3, the drawstrings 27 and 28 of valve 7 extend out of the cuff for a significant distance. As will be understood from this disclosure, these drawstrings have extensions 27' and 28' which extend out of the patient's body when the valve is being implanted. The extensions 27' and 28' are connected to the drawstrings 27 and 28 in the cuff which are means for fixedly attaching cuff 19 to body 20, and are actuating means attached to the drawstrings for operating the drawstrings from outside of the body after the sewing cuff has been attached to the patient to secure the cuff to the body 20. The prior art valve has no such drawstring extensions.

A zig-zag drawstring 26 is connected to extension 28' to be in activated thereby. Drawstring 26 is sewn from top pouch 28 through the cuff and up again through the top pouch. When the activating means is activated, drawstring 28' is pulled and drawstrings 26 and 28 are activated. When drawstring 27 is pulled, drawstring 27 is activated and is pulled into recesses in the body of the valve. The recesses are shown in FIG. 2 at 28T and 27B respectively. FIG. 4 illustrates how the cuff will be drawn into the recesses of the valve body during this cinching procedure. In the FIG. 4 condition, the top cords have not yet been seated. When the cords are pulled tight and cinched up the zig zag drawstring will automatically pull the top cords down into the top recess. Further tightening will cinch the cords tight into the recesses. After tightening, knots can be defined in the cords to secure the means 27' and 28'. FIG. 5 shows the prosthesis after it has been set and the cuff attached to the body.

The sutureless cuff 19 is shown in FIGS. 6, 7 and 8. This cuff can be expanded for sizing. As shown in FIG. 6, the cuff is formed of a single, unitary tubular piece of fabric 18 which is folded over at location 21 to form an inner layer 19I and an outer layer 190, with top cord 28 and bottom cord 27 being located at corners in the fabric. Cord 27 is adjacent to guide means 25. As shown in FIG. 7, stitching 29 and 31 create drawstring pouches 27P and 28P. A final suture stitch 30 is shown in FIG. 8 completes the cuff.

A tool T for placing the cuff in the patient and for applying the fasteners to attach the cuff to the patient is shown in FIGS. 9–16. This tool can be inserted into the patient to initially place the cuff in position, and to set the fasteners to attach the cuff. The tool is operated from outside the patient's body so the overall procedure is minimally invasive.

Figure 9:
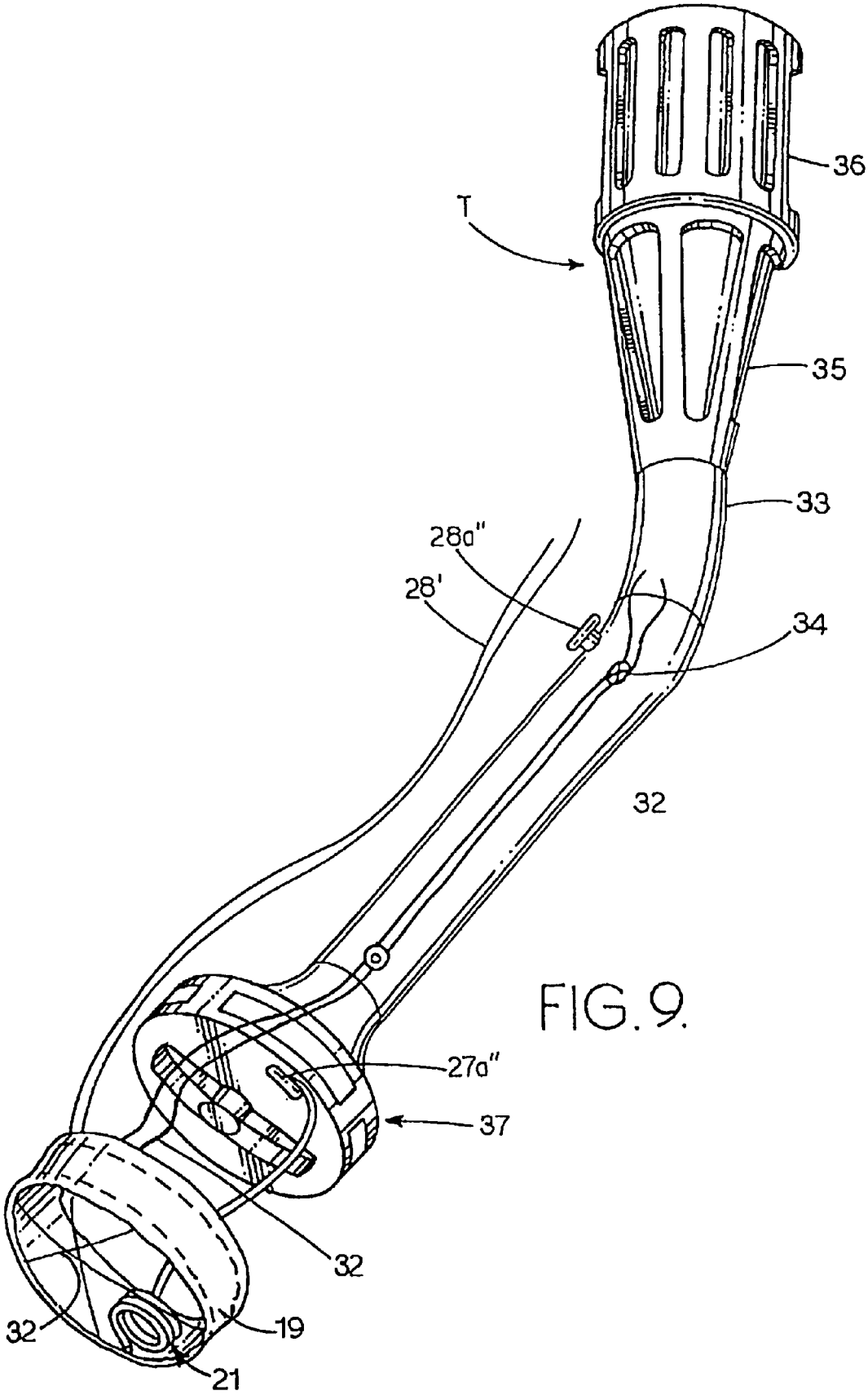
FIG. 9 is a side and bottom perspective view of a preferred form of a fastener driving tool used in the present invention.

Tool T broadly includes an operating handle 35 and a fastener deployment knob 36 on one end of a body 33 which can be curved if desired. An operating head 37 is on the other end of body 33. Anchor means 28a" are located adjacent to handle 35 and releasably attach the activating means 28' to the tool so these activating means are located outside of a patient's body during the cuff attaching procedure. As will be understood from the teaching of this disclosure, once the cuff is attached to the patient and the valve body is in place, the activating means are released from the tool and are operated to attach the cuff to the body. For the sake of clarity, the activating means are shown in FIG. 9 released from the tool. It is also noted that there will be a sleeve on the shaft to keep the drawstrings from winding up on the shaft. Alternatively, the drawstrings can extend through the center of the shaft or held in a coiled at the bottom of the tool.

Suture stays 32 (see FIG. 9) are attached to the tool head 37, and the cuff is stretched over the head 37. The temporary suture stays 32 are drawn over the distal and proximal ends in order to secure the cuff to the head 37 during placement into the patient's body. The temporary suture stays 32 are tied to post 34 so that once the fasteners are deployed, the suture stays 32 can be cut to release the cuff 19 from the head 37 to help the surgeon with alignment of the body 20. The stays 32 act as a hammock or safety net to prevent the body 20 from being placed too low in the cuff which would result in the misalignment of lower drawstring 27 into the lower recess 27B. As deployment knob 36 is turned in a clockwise direction, each half revolution of the knob delivers two pairs of fasteners through the cuff. During that rotation, the latter part of the handle movement indexes head 37 inside the cuff 19 staggering the next pair of fasteners to be delivered. Drawstring activating means 28' is fed up along the shaft of the tool T to the holding cleats 28a" and are removed from this cleat, allowing tool T to be removed from the patient. Activation means 27' is retained coiled at the bottom of the instrument. The means 27' will be played out as the tool is removed from the patient whereby this means 27' will also be located outside the patient for activation.

The tool T has several functions. One function is to insert the cuff into the patient, another is to position the cuff in the patient, another is to fasten the cuff to the patient, and yet another is to hold the cuff securely against the patient's tissue during the fastening procedure. This last function is performed as a dilation and spreading procedure as will be understood from the teaching of this disclosure.

Figure 10:
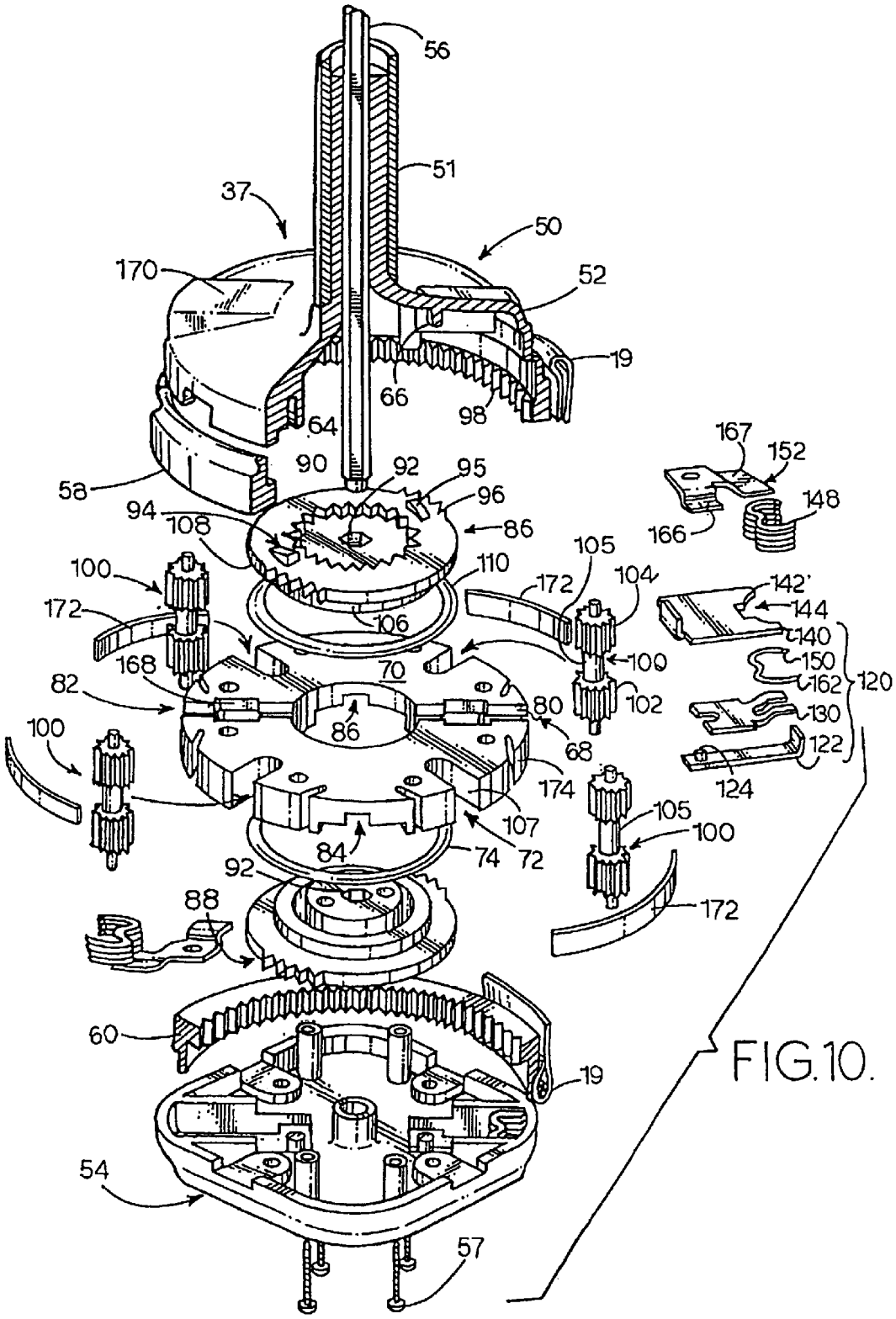
FIG. 10 is an exploded perspective view of the tool shown in FIG. 9.

Referring to FIG. 10, head 37 of tool T is shown as including a housing 50 which includes two sections, upper housing 52 and lower housing 54 both of which are attached to a hexagonal shaped drive shaft 56 and which are attached together by fasteners, such as screws 57. Drive shaft 56 is operatively connected to operating handle 36 to be rotated thereby. The housing sections are slidably connected to index rings 58 and 60 respectively and the cuff is connected to the index rings. As will be explained below, the housings are rotated during the fastening procedure, but the index rings remain stationary with, respect to the housing so the cuff will remain stationary with respect to the housing. The index rings fit into grooves, such as groove 64, to be slidably connected to the housing sections. Upper housing 52 includes an anchor pin 66.

Also fixedly attached to the housing is a driver head plate 68 so that plate rotates with the housing. Plate 68 includes a top surface 70 and a bottom surface 72. Two identical fastener driver accommodating slots are defined on each surface of the driver head plate. These slots are identified in FIG. 10 by the reference numerals 80, 82, 84 and 86 and each extends radially of the plate. The slots are arranged so that top surface-located slots 80 and 82 are offset from each other by 180°, and bottom surface located slots are offset from each other by 180°, with the top surface-located slots being offset from the bottom surface located slots by 105°. After each fastener is set, the tool is rotated by 30° whereby the above-discussed stagger is established for the fasteners. The indexing of the head is achieved by movement of the handle 36 which is attached to a visually indicating means whereby a surgeon can keep track of where the fasteners are being set.

A cam means is located inside the housing. The cam means includes two cam plates, 86 and 88. The cam plates are identical, therefore, only one will be described. Cam plate 86 includes a top surface 90 and has a hexagonal hole 92 defined therethrough to attach the cam plate to drive shaft 56 for rotation therewith. An anti-retrograde means is included on cam plate 86 for preventing the cam plate from rotating in an undesired direction. Rotation in an undesired direction may interfere with the firm placement of the fasteners. The anti-retrograde means includes cleats 94 which are engaged by a one-way prong which permits rotation of the cam plate in one direction only. A second larger set of index lugs 95 can be provided to give feedback to the surgeon at the end of the fastener cycle. Index gear teeth 96 are defined on the outer peripheral edge of the cam plate and are operatively connected to index gear teeth 98 on the index ring 58 in a manner that rotates index ring 58 in a direction opposite to the direction of housing rotation at the same rate of rotation whereby the index ring remains stationary with respect to the patient as the housing rotates. This operation keeps the cuff, which is attached to the index ring, stationary with respect to the patient. Gears 96 and 98 are operatively coupled together by pinion 100 that is mounted at one end thereof on driver head plate 68 and at the other end thereof to the housing section 52, 54. Pinion 100 has a first gear teeth 102 engaging teeth 96 and second gear teeth 104 engaging gear. teeth 98 for transmitting rotation of the cam plate to the index ring. Each pinion has a waist section 105 that is received in a pinion slot 107 defined in driver plate 68.

Figure 11:
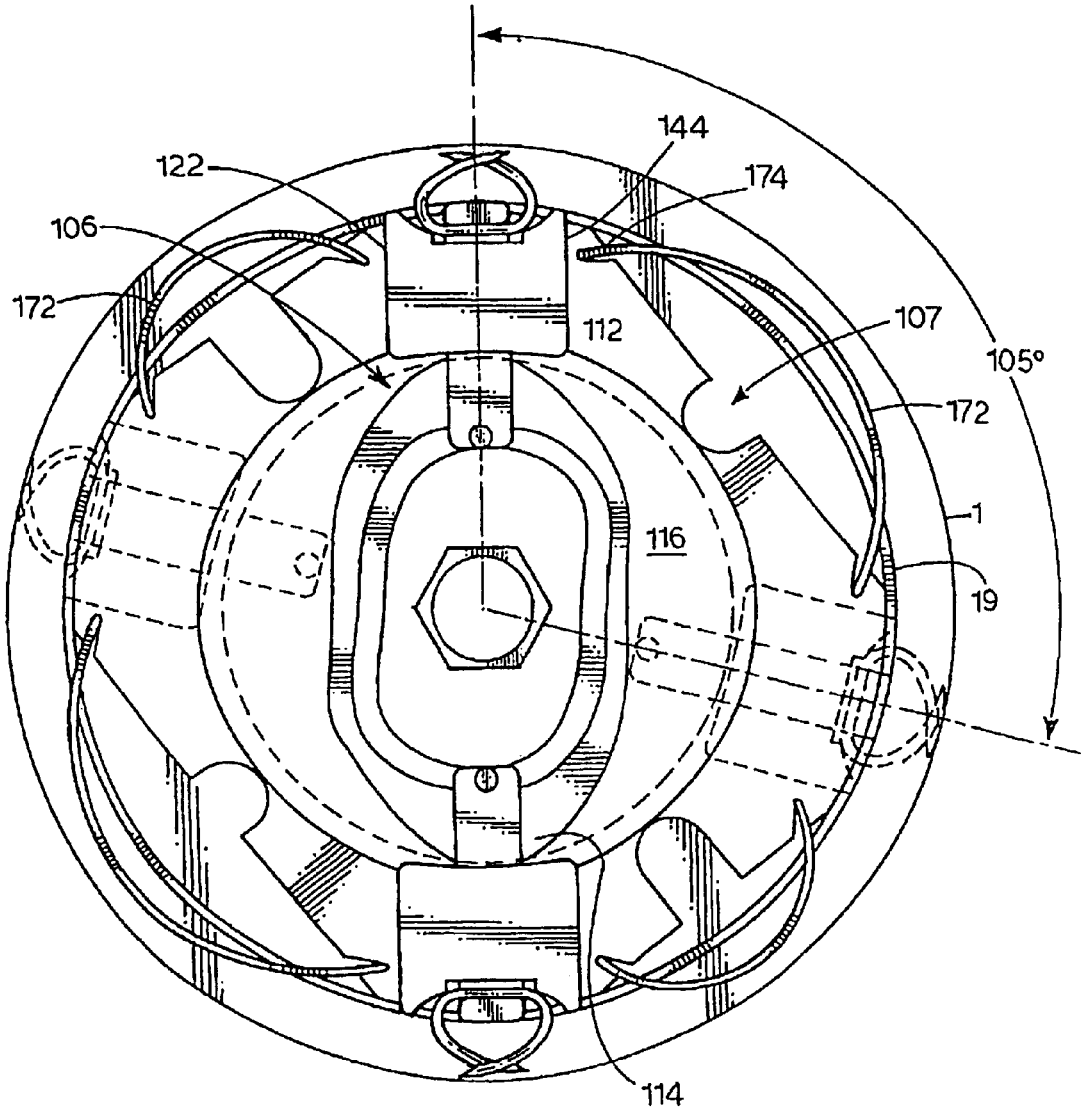
FIGS. 11, 12, 13 and 14 illustrate the various positions of the staple driving mechanism during operation of the fastener driving tool of the present invention.
Figure 14:
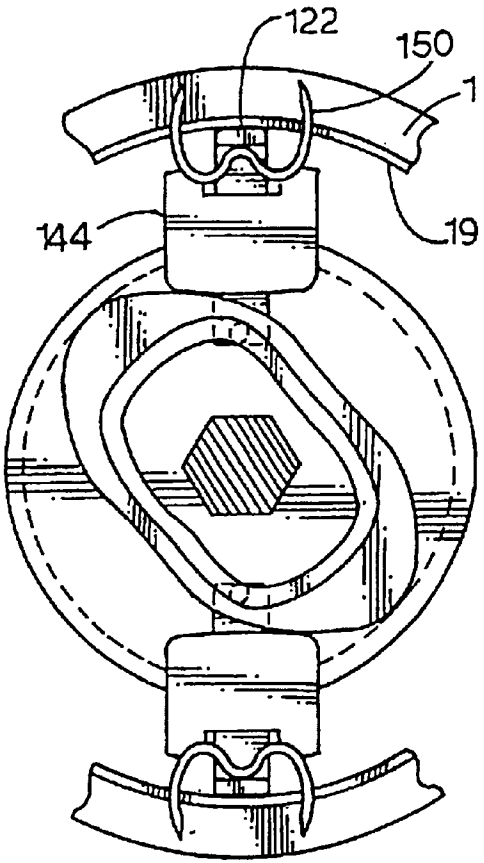
Figure 13:
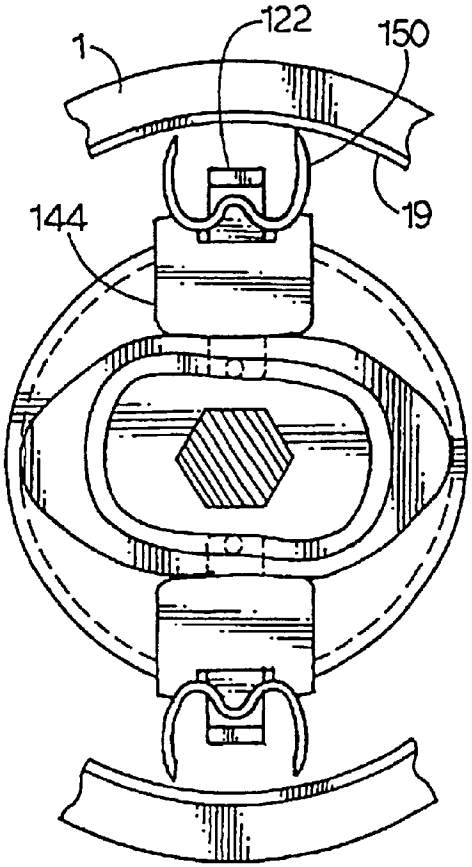
Figure 12:
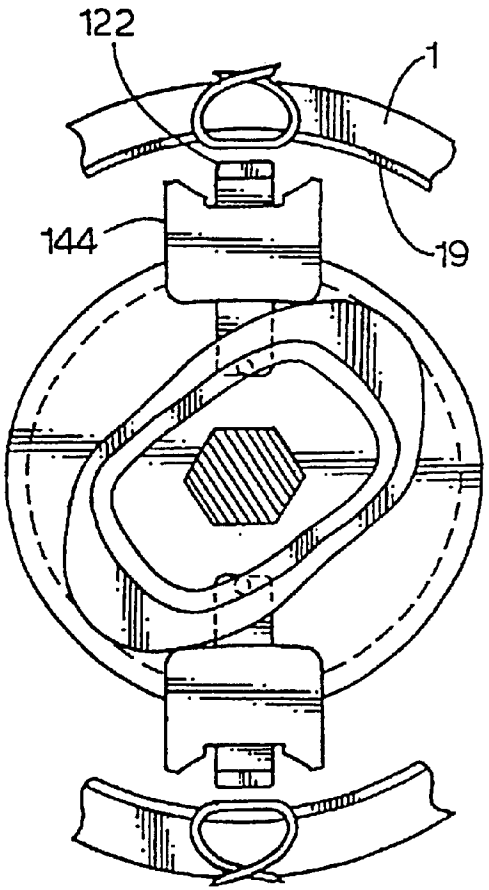
Figure 15:
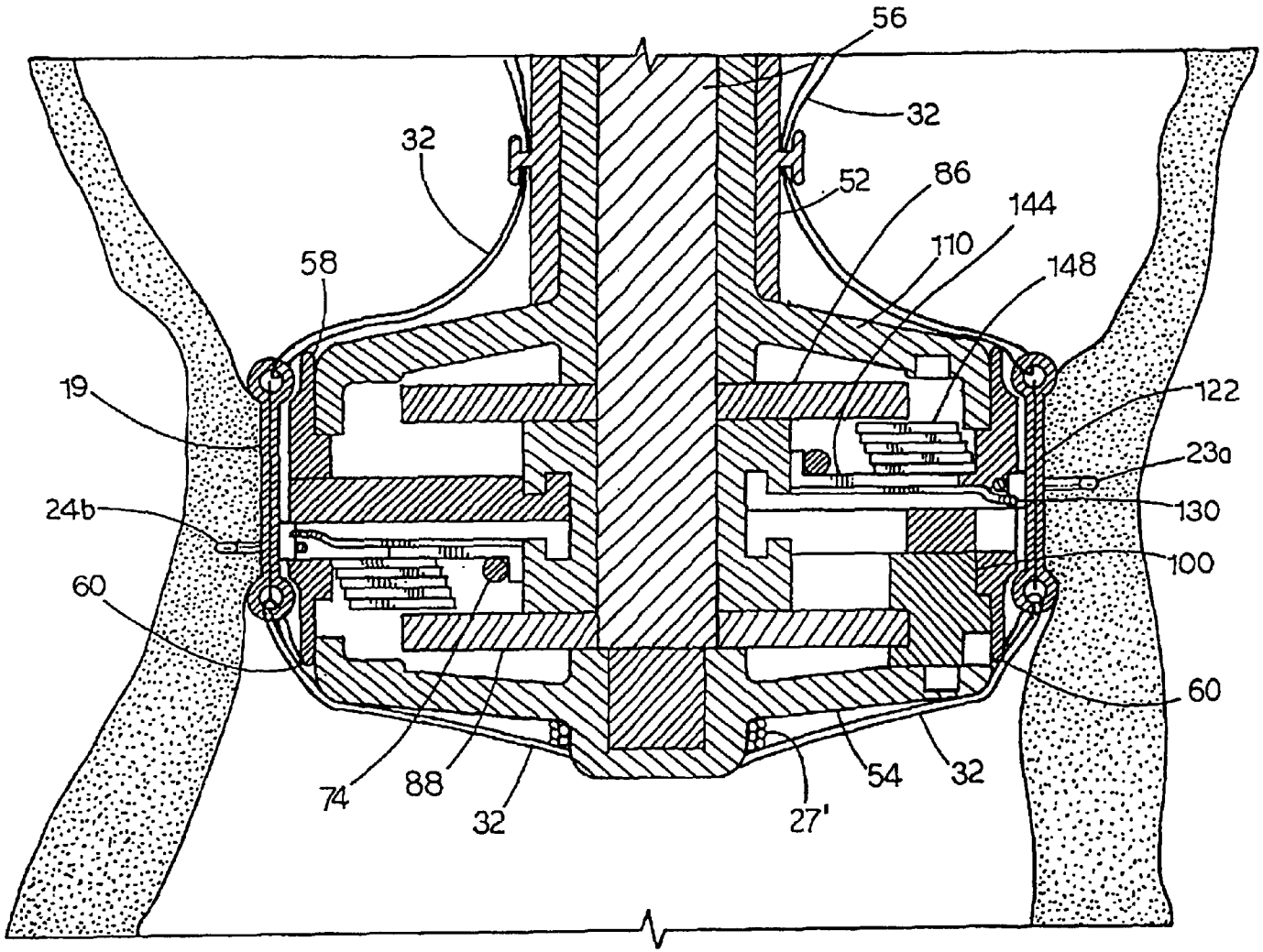
FIG. 15 is a sectional view of the fastener driving tool in the assembled condition.

A cam 106 is mounted on surface 108 of cam plate 90 and has an elastomeric band 110 thereon. The cam 106 is shown in FIGS. 10–12 and rotates with the cam plate. The cam has two lobes, 112 and 114 spaced apart by 180° as well as a groove 116 defined therein for a purpose that will be understood from the ensuing disclosure. The cams are rotated with respect to the driver head plate 68 whereby each cam lobe passes each slot 80 and 82 once each revolution of the drive shaft 56. As will be understood, each revolution of drive shaft 56 thus drives two fasteners from the top surface of driver plate and two fasteners from the bottom of the driver plate. In this manner, even pressure is placed on the cuff and tissue during each fastener driving step because the slots are offset from each other by 180° on each surface of the driver plate. This keeps the cuff and tissue from puckering due to unbalanced fastener driving forces.

Each of the slots 80, 82, 84 and 86 has a fastener driver mechanism 120 accommodated therein. All of the fastener driver mechanisms are identical, therefore, only one mechanism 120 will be described. Mechanism 120 includes an anvil 122 mounted on driver plate 68 to slide thereon, with movement of the anvil in a direction that is longitudinal with respect to the anvil being radial with respect to the driver plate. The anvil includes a pin 124 that is slidably received in groove 116 defined in the cam so the anvil is moved into and out of the slot as the cam rotates. This anvil movement is timed so fasteners can be driven without jamming. A lifter spring 130 is mounted under the driver plate to remain stationary on that plate whereby the anvil moves with respect to the lifter spring. A driver 144 is slidably mounted in the slot and is attached to the cam lobe by ring 110 engaging both the cam lobe and a rider 111. The driver moves radially of the driver plate and is held against chordal movement with respect to that driver plate. Therefore, rotation of the cam plate moves the driver 144 radially inwardly and radially outwardly with respect to plate 68. The groove 116 is formed so that driver and anvil movements are in timed relation to each other. The driver includes two fastener-engaging tips 140 and 142 which are separated by a U-shaped opening 144 having an anvil-receiving notch 146 located therein.

A stack 148 of fasteners, such as staple 150, is contained in the housing to feed fasteners between the driver head and the anvil in a manner that is timed to place a fastener in driving position prior to the driver head moving radially outward in a fastener driving movement. Opening 144 is sized and shaped so that lifter spring 130 moves a driven fastener off of the anvil prior to the anvil moving arcuately away from the driving location and prior to a new fastener moving into the driving position between the driver and the anvil. A stack spring 152 is anchored to the housing section 52 by projection 66 and maintains force on the fasteners that is directed to feeding fasteners to a fastener-setting location after a previous fastener has been driven through the cuff and into the tissue. The anvil folds the fastener in a manner such that the sharp points 162 of the fastener drive directly through the cuff and the tissue rather than tear through the cuff and tissue. The anvil then folds the fastener after that fastener has pierced the cuff and the tissue to establish the closed fastener. Each stack spring also has an anti-retrograde spring 166 thereon. Spring 166 engages cleats 94 on the cam to prevent the cam from moving in an undesired retrograde direction. Fasteners are retained into the housing via recesses or doors, such as pocket 170. Each stack spring 152 also has two wings 167 that engage slots 168 defined in the driver plate to maintain the stack spring in the proper orientation and position to feed the fasteners, yet which will permit the stack spring to be removed via the door 170 to load fasteners. However, the preferred form of the tool is disposable.

As above discussed, it is a significant advantage of the tool T that the cuff is maintained in contact with the tissue during the fastener setting procedure. This advantage is realized by means of cuff dilation means, such as spring 172, mounted on the driver plate and extending radially outward from the outer peripheral edge of that driver plate. The springs curve gently outward and inward in a U shape to gently engage the cuff from the inside of that cuff and gently urge it against the tissue. The springs are mounted on the driver plate by spring-receiving slots, such as slot 174, defined in the outer peripheral edge of the driver plate so the spring is maintained on the plate and in the desired orientation.

For purposes of clarity, four positions of the fastener driver mechanism are shown in FIGS. 11, 12, 13 and 14. Beginning a cycle, a fastener has been driven through the cuff and the adjacent tissue, and is formed in FIG. 11 when the driver forces the fastener against the anvil. As the drive shaft is further rotated, the cam lobe moves from the FIG. 11 position to a retracted position shown in FIG. 12, with the anvil being pulled back after the set fastener has been pushed off that anvil by the lifter spring 130. Continued rotation of the drive shaft rotates the cam lobe into a loading position shown in FIG. 13 during which time, a new fastener is fed between the anvil and the driver. Further rotation of the drive shaft rotates the cam into an advance position shown in FIG. 14 which forces the driver against the fastener and the fastener through the cuff and the tissue.

Once all of the fasteners have been set, sutures 32 are unfastened from the cleat 34 on the body 33, cut and loosened to permit the tool to be removed from the patient. Then means 28' is removed from the cleat on the tool. Then, tool 85 is removed from the patient which plays out activating means 27' to the outside of the patient. A prosthetic valve body 20 is then inserted into the patient using a tool T' shown in FIG. 20, and is placed in position adjacent to the cuff. The valve body is moved until the surgeon is notified by the indicating means that the body is in the desired orientation. The activating means 27' and 28' are then activated to pull the cuff over and against the body by the above-discussed action of the drawstrings. Once the drawstrings are operated and the cuff is held tightly against the body 20, the activating means can be severed and removed from the patient. The prosthetic valve is now in place. Any tools can be removed from the patient and closure can be effected. As above discussed, the fasteners will be continuous over the entire perimeter of the cuff thereby further ensuring that no leak paths will develop. The continuous nature of the fastener coverage is best understood by visualizing a unit vector UV as shown in FIGS. 3 and 4, which is centered at the center of the cuff and being two rows thick, that is having a thickness indicated in FIGS. 3 and 4 by dimension $t_v$. As this unit vector moves through 360°, it will never be out of contact with a fastener whereby the entire circumference of the cuff is fastened to the tissue. The horizontal orientation of the fasteners further contributes to this feature.

Figure 20:
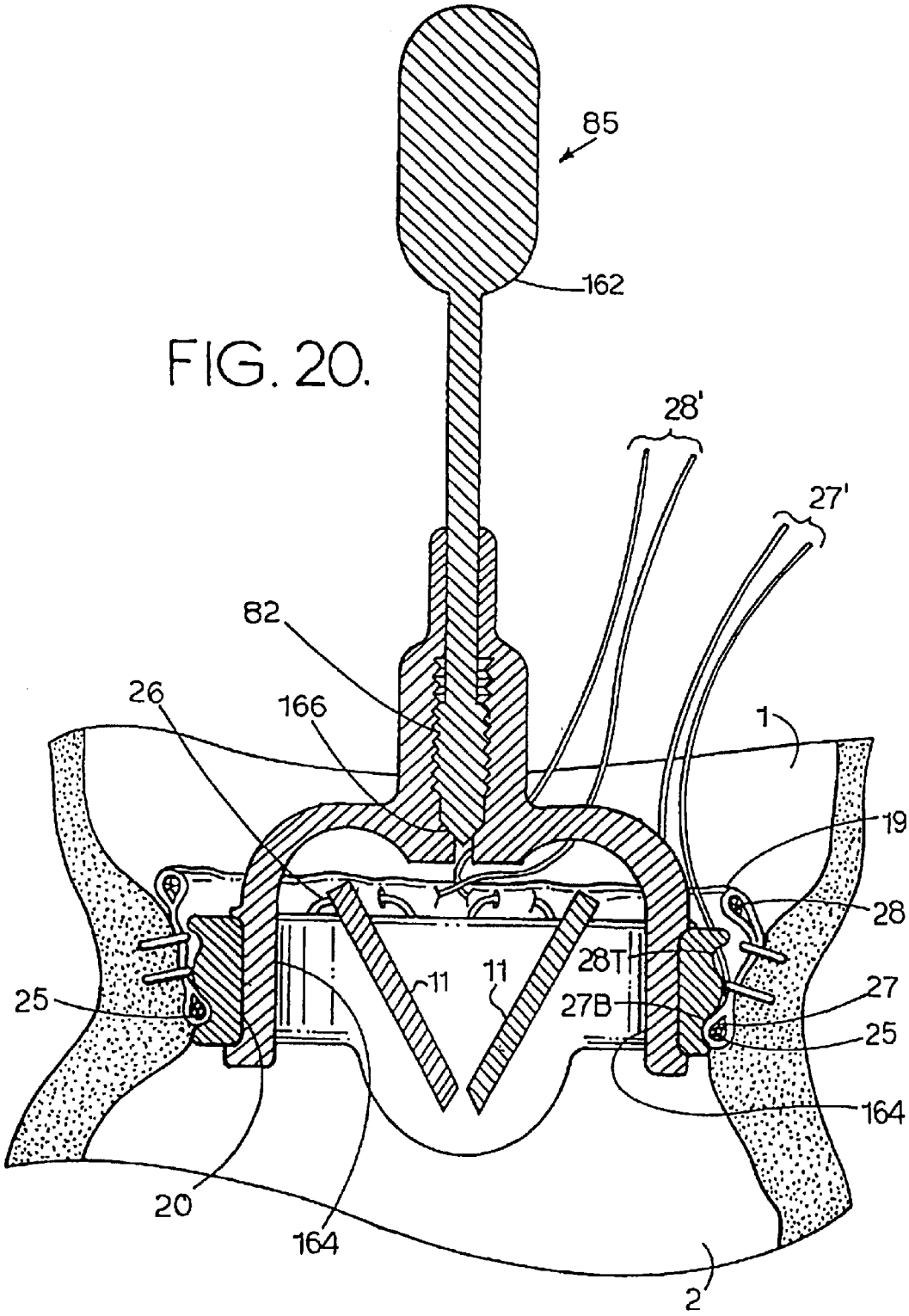
FIG. 20 shows a valve body holding tool inserting a valve body into an in-situ cuff.

As shown in FIG. 20, tool 85 includes a handle 162 and a pair of legs 164 which are spread apart by screwing handle 162 into the bottom of a holding fixture 164, forcing tapered edge 166 into the legs. The valve may then be inserted down into the cuff 19 until the garter spring 25 in the cuff is felt to detent into the lower recess 27B indicating proper seating of the valve body in the cuff.

Figure 16:
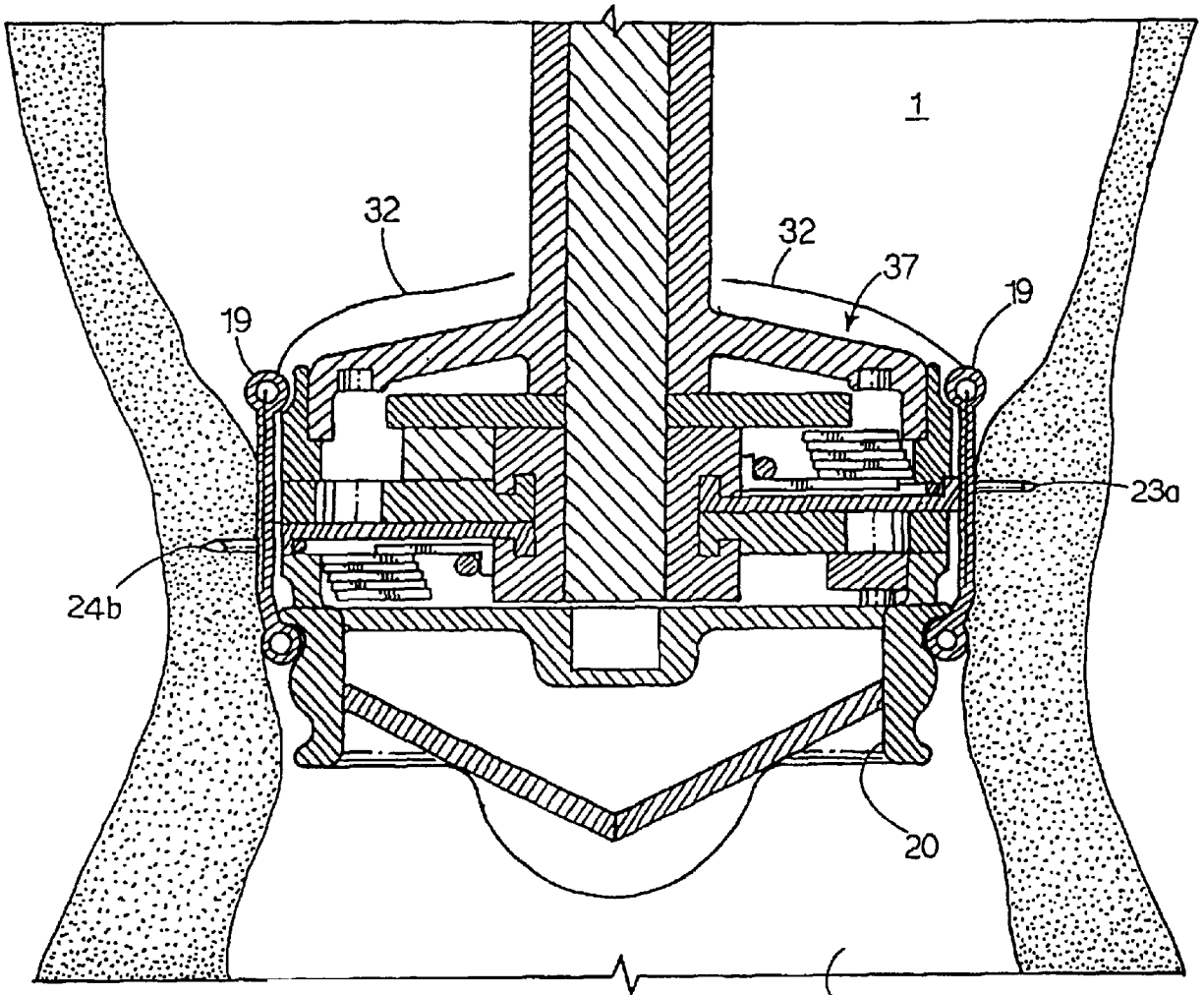
FIG. 16 shows the fastener driving tool in position after the cuff has been stapled to the patient and prior to movement of the valve body into position in the in-situ cuff.
Figure 17:
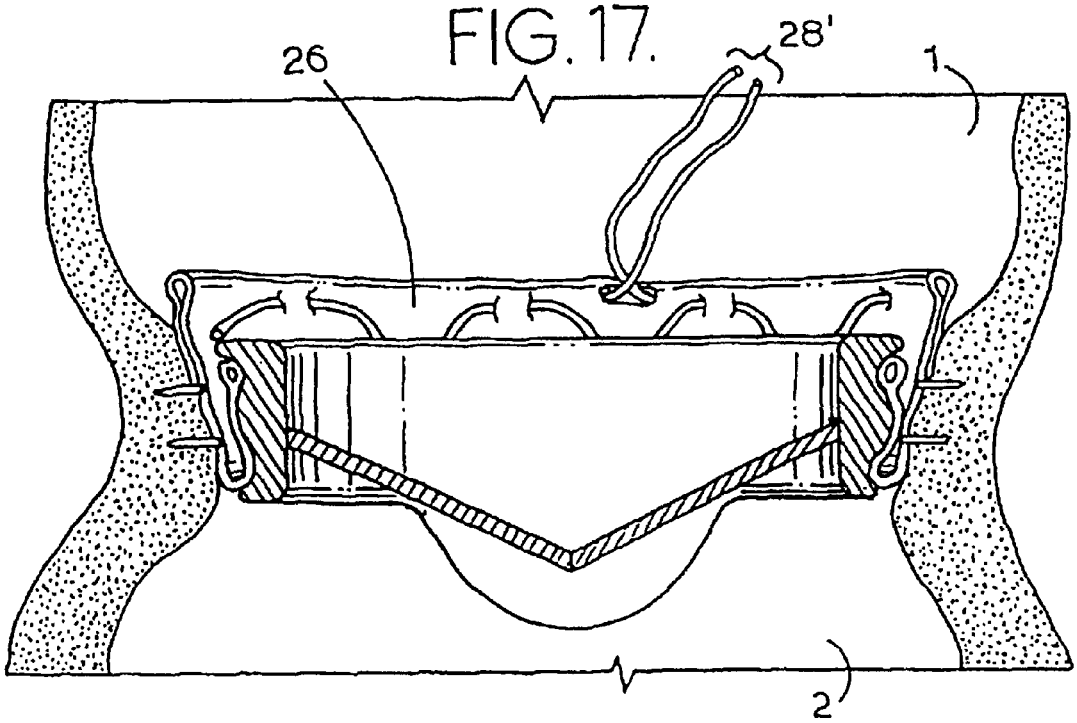
FIG. 17 shows the in-situ cuff with the valve body in place prior to attaching the valve body to the cuff.
Figure 18:
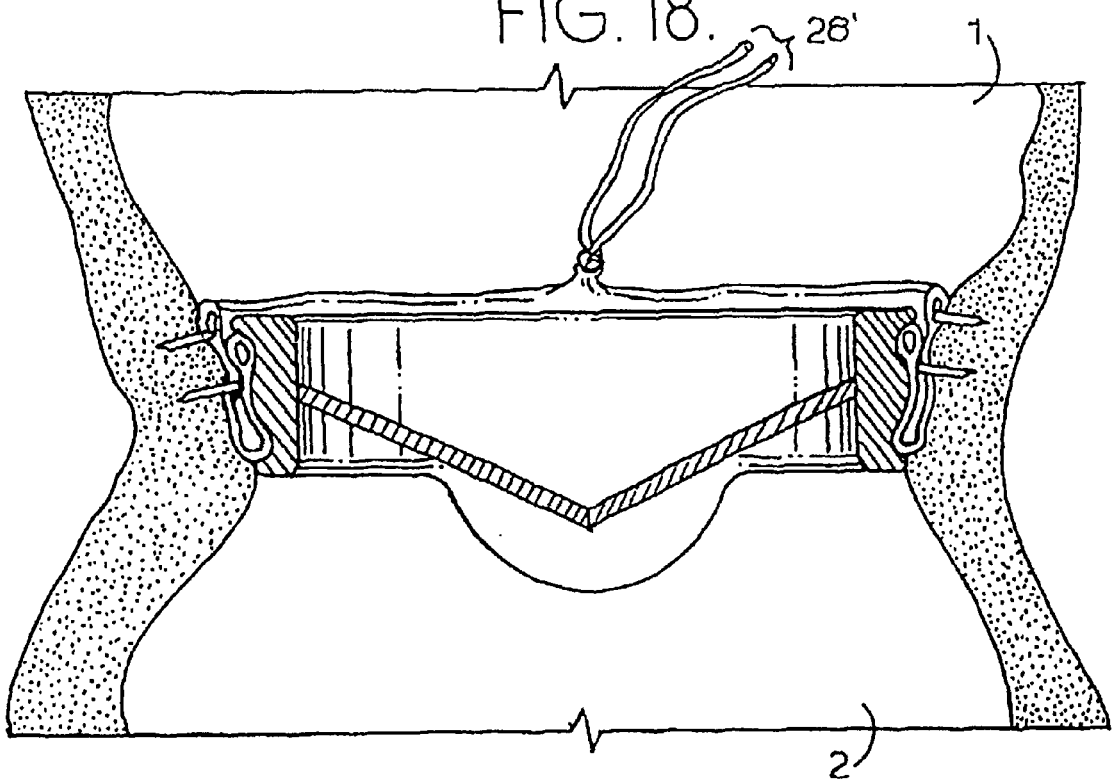
FIG. 18 shows the cuff attached to the patient and to the valve body that has been moved from the FIG. 16 position to the FIG. 17 position.

An alternative form of the tool is shown in FIGS. 16–18 and maintains contact between the tool and the cuff whereby the cuff can be inverted after the valve body has been moved into position. The valve body is attached to the tool and to the cuff during fastening of the cuff to the tissue. After completion of the fastening step, the valve is pulled up thereby inverting the lower section of the cuff. The drawstrings are then cinched as above described.

Figure 28:
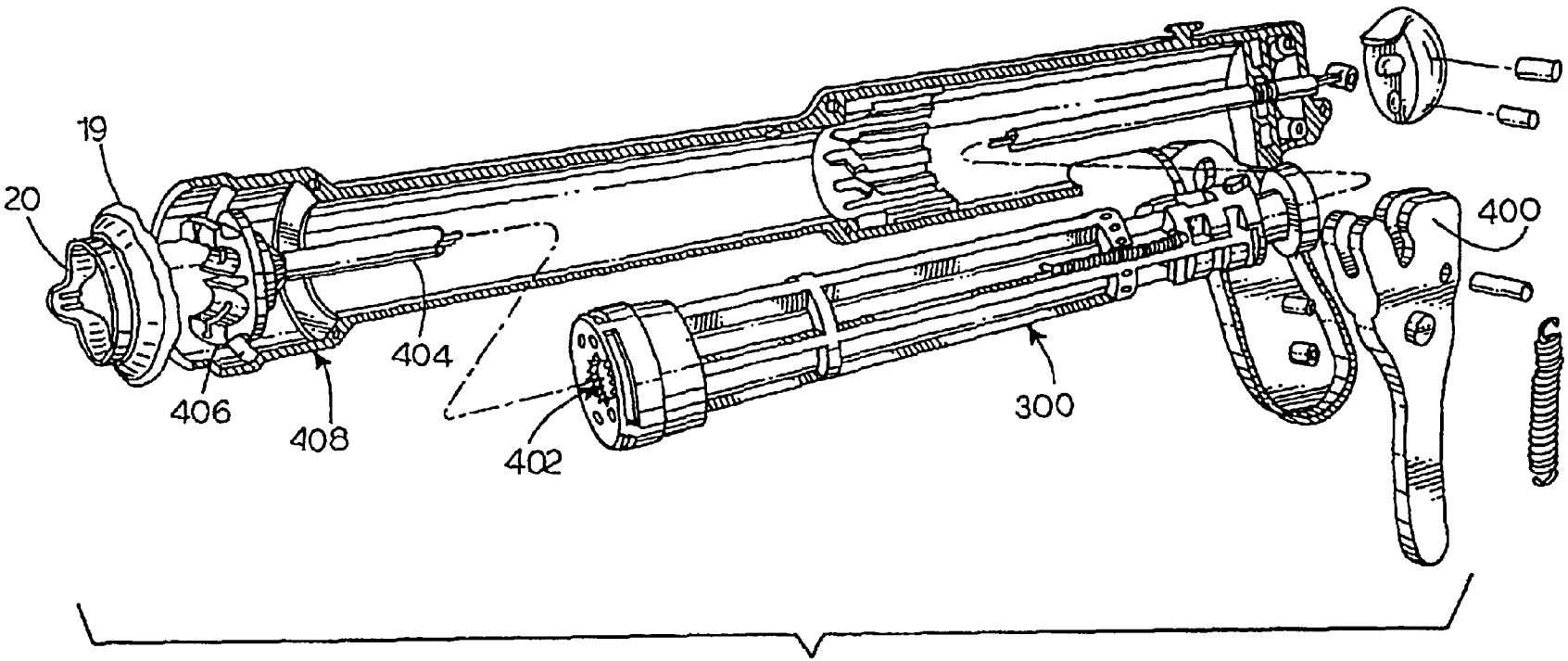
FIG. 28 is an exploded perspective view of another form of the tool which maintains the handle and shaft stationary during fastener delivery.
Figure 29:
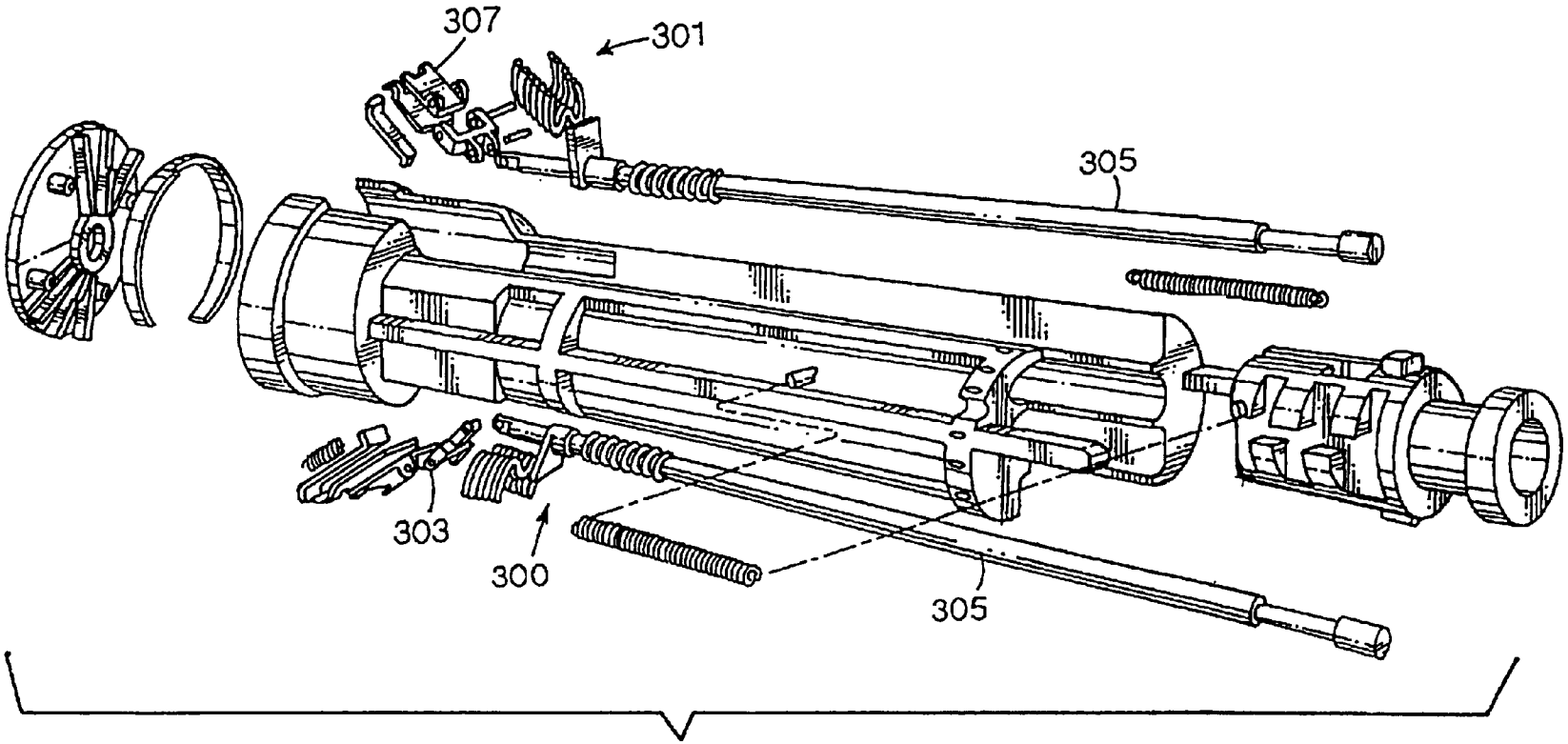
FIG. 29 illustrates a rotating fastener assembly for use in the tool shown in FIG. 28.
Figure 30:
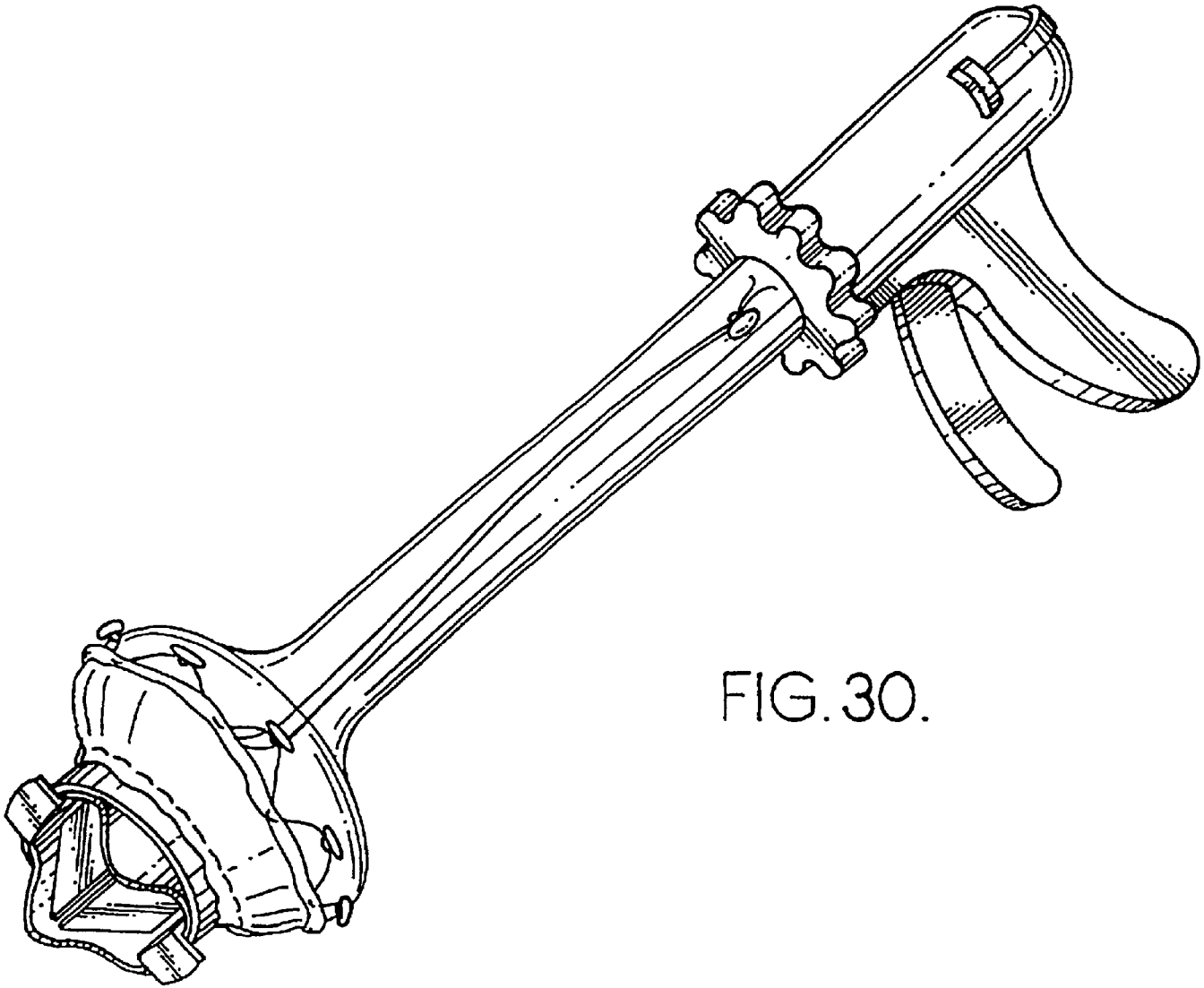
FIG. 30 is an assembled view of the FIG. 28 tool.

As above discussed, the central shaft experiences a counter-rotation as the driving head is indexed so the cuff is held stationary with respect to the patient's tissue while the fastener head is being indexed to the various positions. A further alternative form of the tool is shown in FIGS. 28 and 30 at T' and keeps the handle and the shaft stationary while the fastener delivery system rotates. A rotating fastener assembly 300 is shown in FIG. 29. Tool T' includes mechanisms necessary to deliver the fasteners and which are located inside the central shaft. A lever 400 actuates the mechanisms from within the housing. A central bore 402 is defined in the housing of the tool and has a central retaining stalk 404 therein on which the distal end 406 of the sewing cuff 19 is located. The heart valve base can also be attached to the stalk end 406 if the base is attached to the cuff 19 prior to setting the fasteners. The cuff is temporally attached to the outer housing 408 and the stalk 404 which remain stationary during the fastening procedure and the fasteners are delivered in a coaxial method from between two stationary parts. Within the central fastener delivery assembly 300 are components similar to the above-described cam mechanisms needed to drive staples through the cuff and form them in the annular tissue from within. As above described, driver mechanisms 301 are diametrically opposed and offset with respect to each other to create the appropriate overlapping staple spacing discussed above. Staggering allows two distinct rows of staples to be formed as above discussed whereby total coverage of the cuff is effected. Toggle links 303 are used and are connected to longitudinal drive rods 305. Drive rods 305 translate handle-generated forces into fastener delivery forces at the toggle links 303. Each toggle link 303 is connected to a staple driver 307. The fastener assembly 300 is rotated a plurality of times to form the two rows of staples. Flexible shafts (not shown) can also be used to permit the driving angle of the fasteners to be altered as necessary. Flexible shafts can also be used to permit the tool to operate to drive fasteners from the superior to inferior side of a suture cuff which might be pre-attached to the valve body. Such a cuff could be temporarily tied to the stationary housing. Upon insertion of the valve, cuff and instrument would be inserted into the annulus. Each fastener would form from the superior side of the cuff penetrating the cuff and annular tissue below. Again, as above discussed, one or more complete rows of fasteners would be formed holding the cuff to the annular tissue.

A balloon B (see FIG. 24) is used as a means for anchoring and positioning. Balloon B can either be attached to the fastener driving device or be separate. The balloon can be inflated using a hand pump HB. The balloon is pulled up snugly under the annular tissue and the device is brought down to it. Then, the tool can be drawn up close to the balloon trapping the annular tissue and aligning the tool for forming fasteners.

Figure 25:
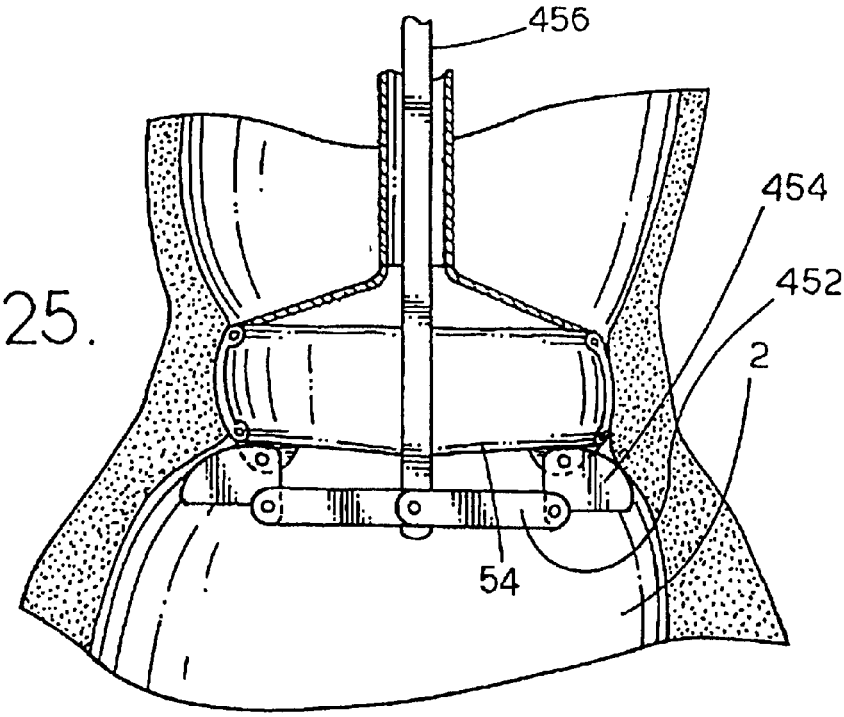

A second method (see FIG. 25) uses levers 450 and links 452 to deploy small flanges 454 around the lower periphery of the lower housing 54. By actuating a central rod 456, the connecting links pivot the flanges outwardly providing a lip in which the surgeon can draw the tool upward locating the staples in the proper location in relation to the annular tissue.

Figure 26:
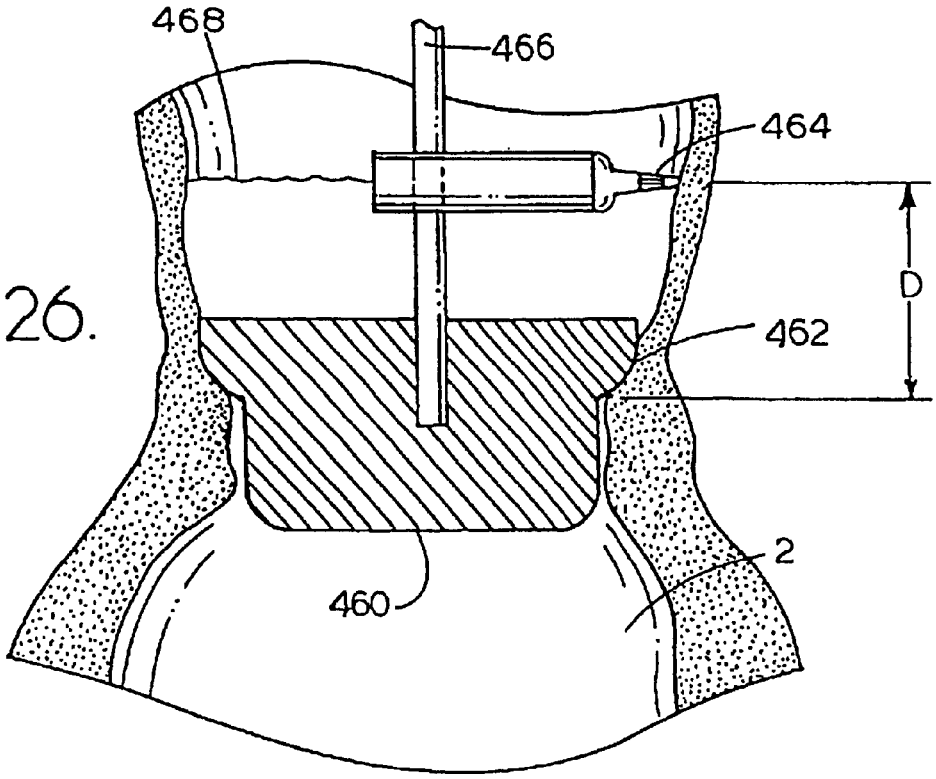

A third method (see FIG. 26) uses a clear cylindrical sizing tool 460 which uses a lip 462 or flange that sits on top of the annular tissue 464. It also has a special tissue marker mounted on a central shaft 466. The surgeon will visualize the contact of the annular tissue from above. The contact with the surface will create a wetted dark circle when properly seated on the annulus. At that point, the surgeon rotates the central shaft 466 which creates a line 468 inside the aorta. This line would have a distance D (FIG. 26) that would correspond to a pointer or landmark to be used to line up the device in the correct position.

Figure 27:
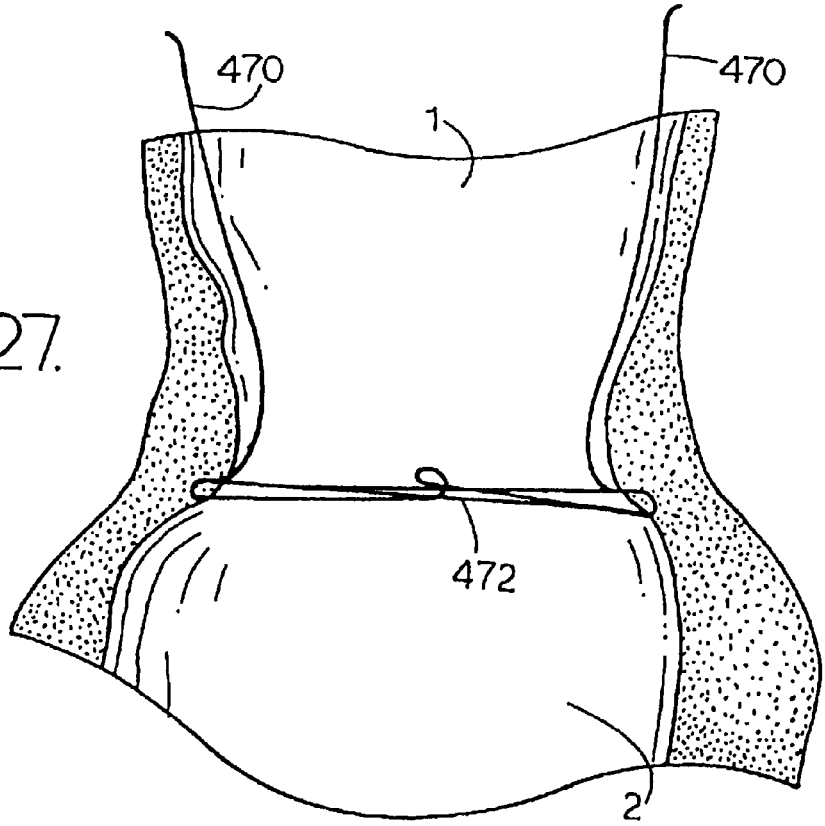

Still another way (see FIG. 27) to gauge the placement of the device is to drive sutures 470 below the annulus to create a safety net 472 that will not allow the device to plunge too deeply into the left ventricle 2. The device is then inserted until the resistance of the suture net is felt by the surgeon. Once the cuff is fastened into the annulus, the sutures can be cut and removed from the annulus.

In the interest of completeness, an open thoracotomy surgical technique for aortic valve replacement will now be discussed (see FIGS. 19A and 19B). A surgical incision 200 is made in one of several locations: a midline sternotomy incision; or a small anterior right or left thoracotomy; or a mini-thoracotomy (with or without rib removal); or a posterior thoracotomy; or a suprasternal or supraclavicular approach; or through port sites (mini incisions) over the chest wall. The pericardium is then opened. The patient is then placed on cardiopulmonary bypass using: right atrial cannulation; or femoral vein-femoral artery; or femoral artery-left atrium; or aortic-left atrial cannulation. The aorta is dissected for access and clamping. The aorta is then crossclamped and cardioplegia is delivered through: the aorta, coronary ostial cannulation or retrograde through the coronary sinus to arrest the heart. A venting device is then inserted.

The aortomy is then performed. The aortic valve is excised and the annulus, aorta and/or the anterior leaflet of the mitral valve, and septum are debrided as necessary and appropriate. A device or devices that determine the relative size of the annulus and that identify the position of the staples and stapling device, is inserted into the annulus. When appropriate, sizing and positioning are determined, a biologic marker is circumferentially traced over the top (most superior) edge of the position/sizing device, to guide the proper placement of the stapling device. A balloon or levers can also be used.

The position/sizing device is then removed and the stapling device is inserted and positioned in the annulus with the cuff of the valve. The stapling device is positioned with the cuff lying in the annulus and the position confirmed by its proximity to the circle previously marked. The stapling device is enabled to dilate the annulus with the valve cuff in situ.

The stapling device is then actuated. The appropriate size of mechanical valve skeleton is then inserted into the cuff. The valve and the perivalvular area are tested for proper size and the device is removed. Once the proper size is established, the skeleton is removed and the valve base is inserted. The drawstings of the cuff are then tightened and tied securely to trap the mechanical valve to the cuff. This assures that the largest desirable valve base will be used. The aortomy is closed with traditional sutures or with vascular staples. The heart is de-aired and the crossclamp removed. The patient is then removed from cardiopulmonary bypass and the wounds are closed.

An alternative technique with the valve pre-attached includes the following steps. All methods up to and including placement of the biologic marker circumferentially over the top edge of the position/sizing device are repeated. Then, the position/sizing device is removed. The stapling device already pre-attached to a mechanical or tissue valve of appropriate size is lowered into the annulus. The stapling device and the cuff of the valve are positioned in the appropriate place in the annulus using the biological marker circle previously marked on the aortic wall for verification. The cuff-valve border at this time would be found in a slight subannular position.

The stapling device is then actuated. The drawstrings in the cuff of the valve are drawn and tied securely to bring the valve in proximity to the annulus. The remainder of the steps are the same as above described.

Yet a third technique for aortic valve replacement is through the left atrium. This technique includes the following steps: surgical incisions are made in the manner discussed above; the pericardium is opened; the patient may or may not then be placed on cardiopulmonary bypass. The technique then includes the use of imaging devices (both intra and extra-vascular) being used to guide the conduct of the operation. Purse string sutures (access) are then placed on the left atrium and aorta. Flexible imaging devices and instrumentation is then inserted through the left atrium (and aorta). The devices are lead through the mitral valve and into the left ventricle. The aortic valve is then imaged both through the aorta and left ventricle and is excised.

The valve stapling device is then inserted through the left atrium and positioned in the aortic annulus. The stapling device is then activated and positioning assessed both through the left ventricle and aorta using the imaging devices. The stapling device is then removed, and all cannulation sites secured. The heart is then deaired and taken off cardiopulmonary bypass if appropriate. The wounds are then closed.

Figure 19A:
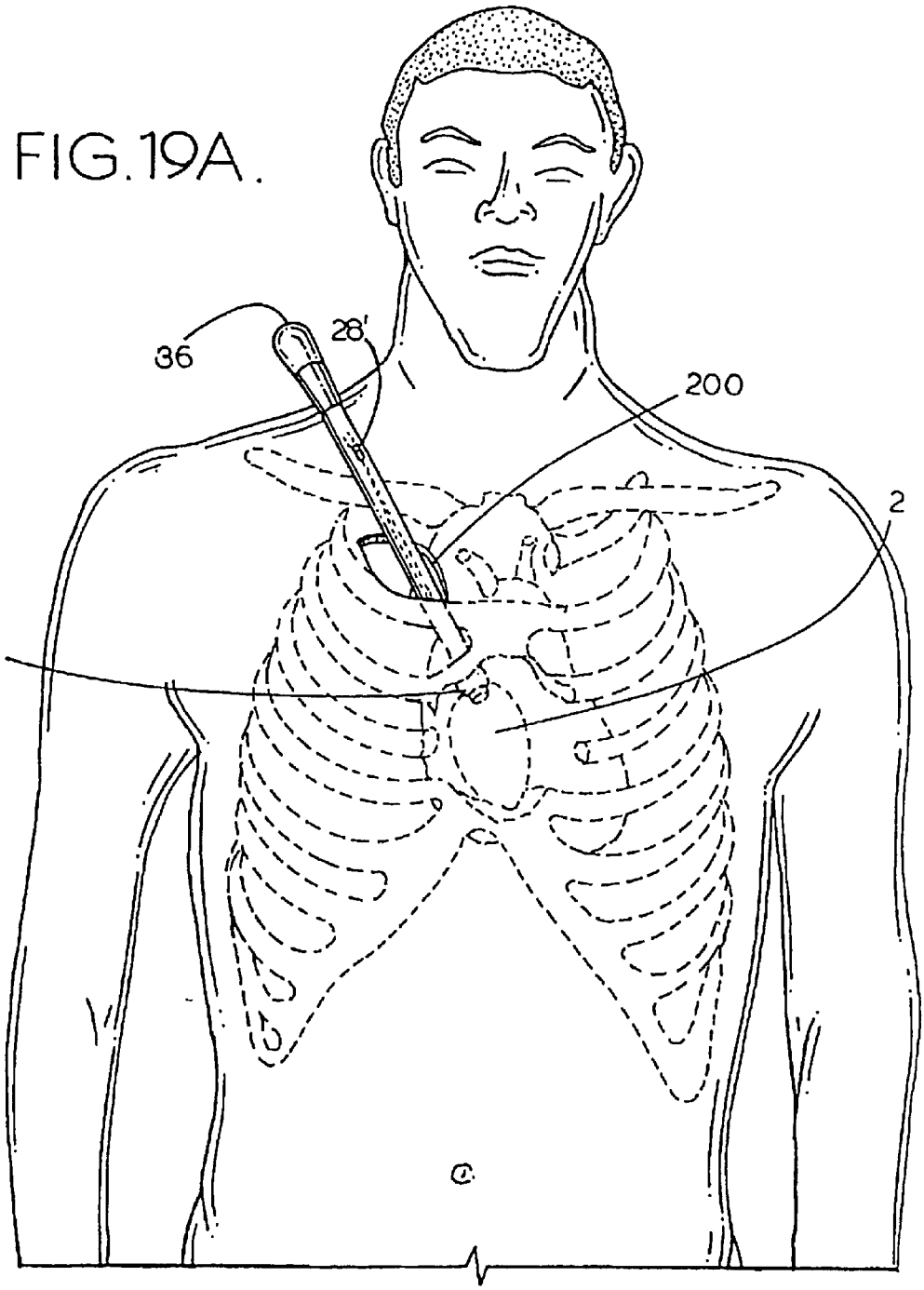
FIG. 19A illustrates the torso of a patient having the prosthetic valve of the present invention being placed using a fastener driving tool of the present invention in a minimally invasive surgical procedure according to the teaching of the present invention.
Figure 19B:
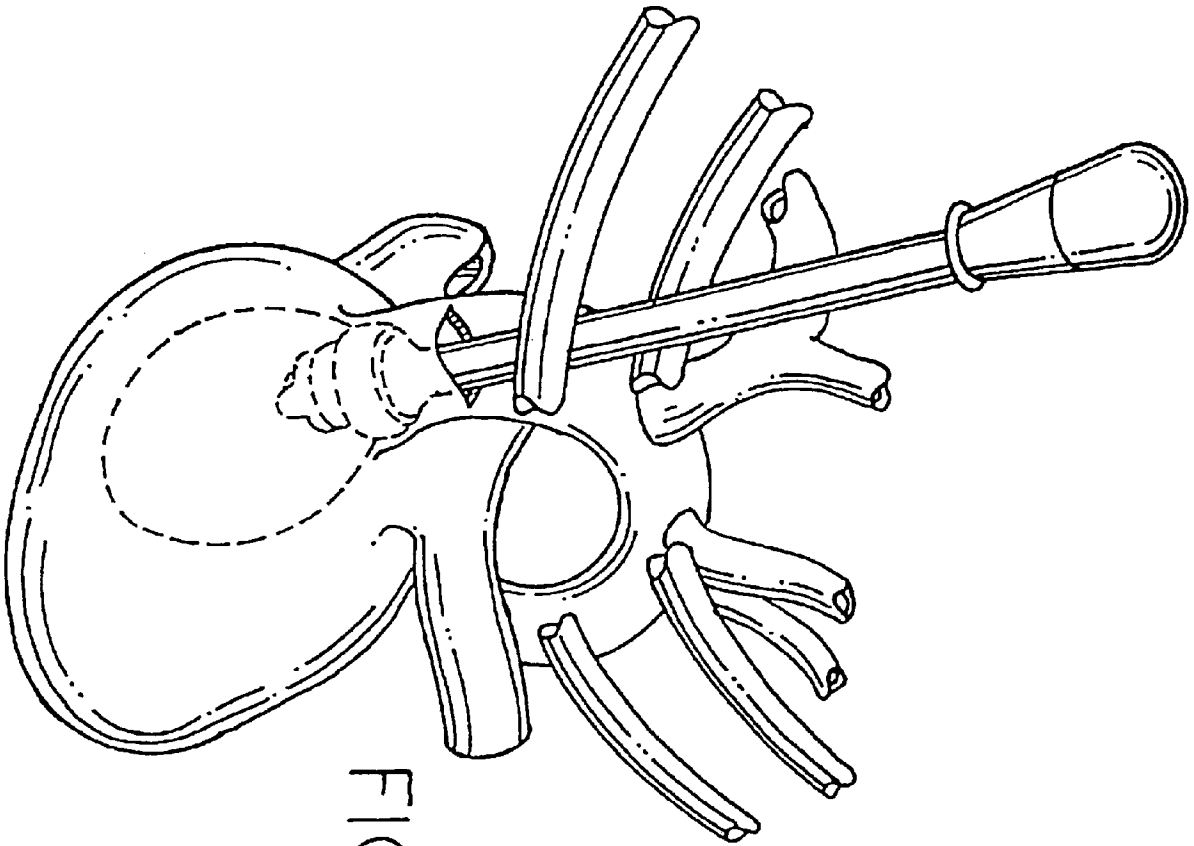
FIG. 19B illustrates the tool inserted into an aorta.

A minimally invasive surgical procedure is illustrated in FIGS. 19A and 19B. A torso with an overlapping rib cage is shown. Access to the aorta is gained through an incision 200 in the superstenal notch passing below the manubrium or via a mini-thoracotomy is performed in the area of the first and second ribs enabling visualization of the aorta. A small incision 202 across the aorta above the annulus is made. The fastener driving tool T with attached is inserted through the incision after the faulty valve has been excised. The knob 36 is rotated while holding the handle 35 to deploy the fasteners through the cuff 19 and into the aortic annulus. Once the fasteners have been driven into the aortic annulus, the stay sutures 32 are removed from cleat 34 allowing the head of the instrument to be removed from the patient's body. Activating means 27' and 28' are also removed from the cleats 27a" and 28a". The heart valve body is then placed into a holding fixture, such as the above-discussed fixture, and inserted into the aortic annulus in the same manner as the tool T. The valve body is then docked into the sewing cuff 19. The indicating means provides tactile feedback for the surgeon to determine when the heart valve body 20 is properly seated. Temporary stays 32 prevent the heart valve base from descending too far and aligning the drawstrings with the recesses in the valve body. Once the lower drawsting has been cinched up, the upper drawsting is pulled tight. The zig-zag drawstring 26 will then pull the cords into the top recess 28T.

Figure 21:
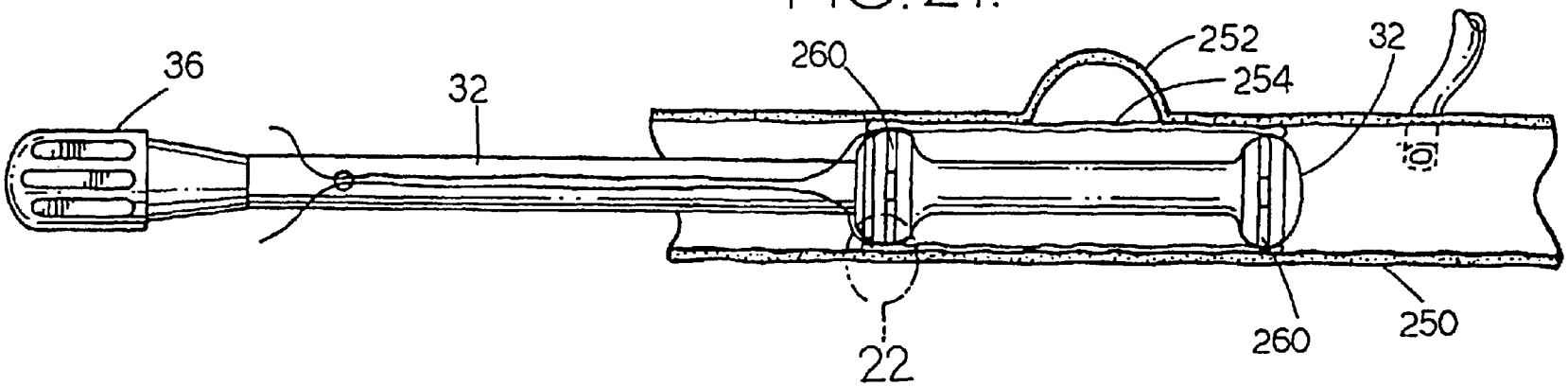
FIG. 21 shows an alternative form of the tool having two fastener-delivering heads and which can be used to repair an aneurysm.
Figure 22:
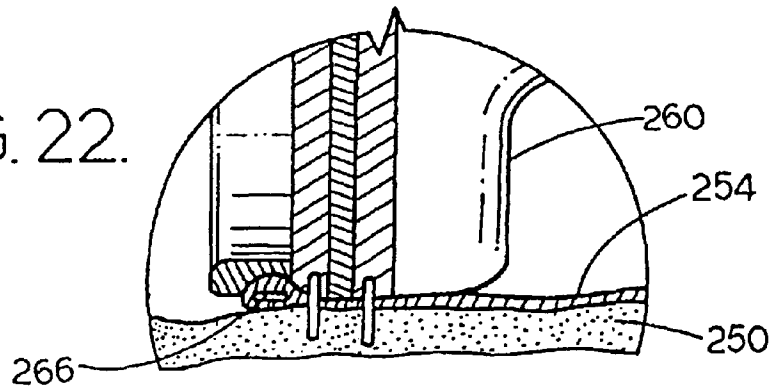
FIG. 22 is an exploded section of FIG. 21.
Figure 23:
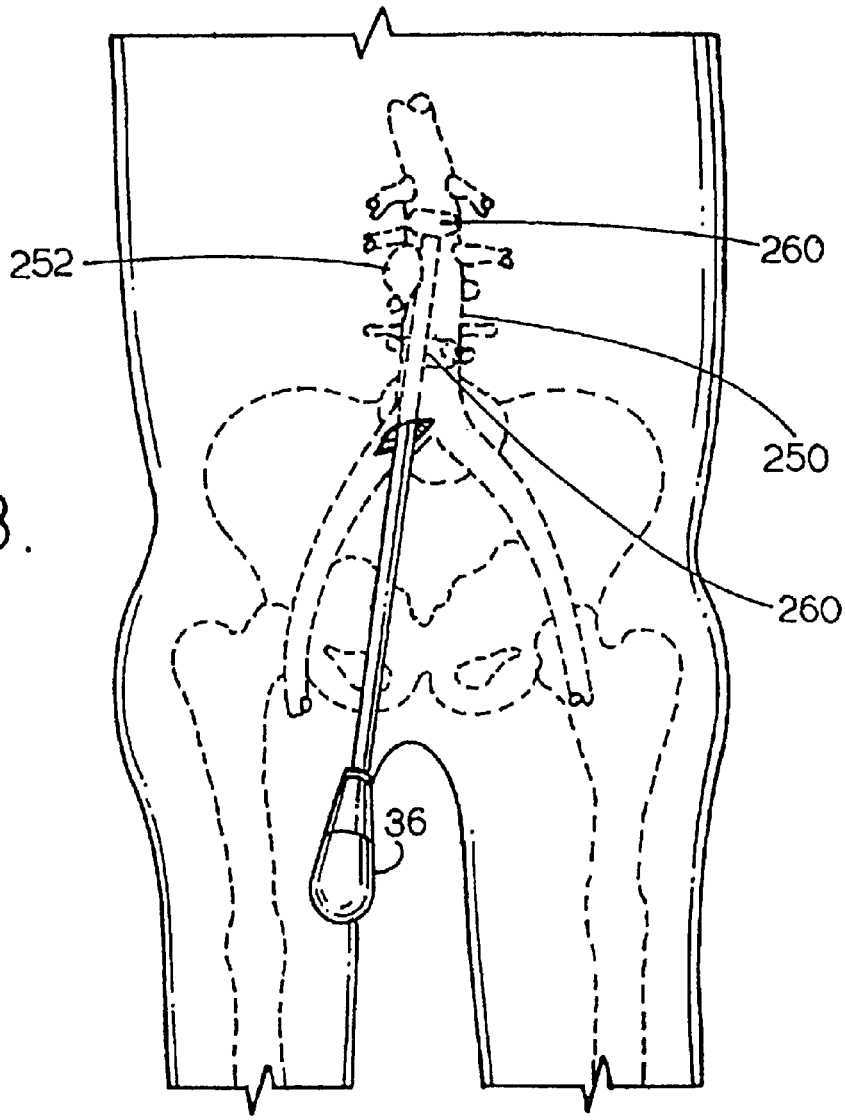
FIG. 23 shows use of the tool shown in FIG. 21 to repair an abdominal aortic aneurysm.

As shown in FIGS. 21–23, the system can be used to repair an abdominal aortic aneurysm (AAA) which may occur because of a thinning of the aortic wall 250. The wall balloons out under positive pressure and forms a pouch 252. These aneurysms present life-threatening consequences for the patient should they rupture. If detected prior to rupture, a graft 254 can be placed on the aorta, in an abdominal graft procedure to provide support to the weakened area of the wall. The graft is usually made from a tube of Dacron fabric and is most often sutured in place.

However, using the teaching of the present invention, the graft can be stapled in place. As shown in FIGS. 21 and 22, the dilating fastener deployment feature of the present invention permits fasteners to be formed from the inside toward the outside of the aortic wall. As shown in FIG. 21, the fastener deployment device has two driving heads 260 to deliver fasteners through the graft on either side of the aneurysm 252. At each end of the graft in FIG. 22 there is a metal ring 266, analogous to the garter spring discussed above. These rings help to keep the graft open once it is fastened to the aortic wall. FIG. 23 illustrates access to the aorta gained through entry in the femoral artery in the pelvic region. The fastener deployment device, with graft attached, would be inserted into the femoral artery and fed up to the area of the aneurysm. The distal head 260 is positioned beyond the aneurysm and the proximal head 260 is positioned to center the aneurysm underneath the graft. Fasteners are formed in a manner similar to that discussed above, completing the installation of the graft. Stay sutures may be used to hold the graft in place during fastening.

Figure 24:
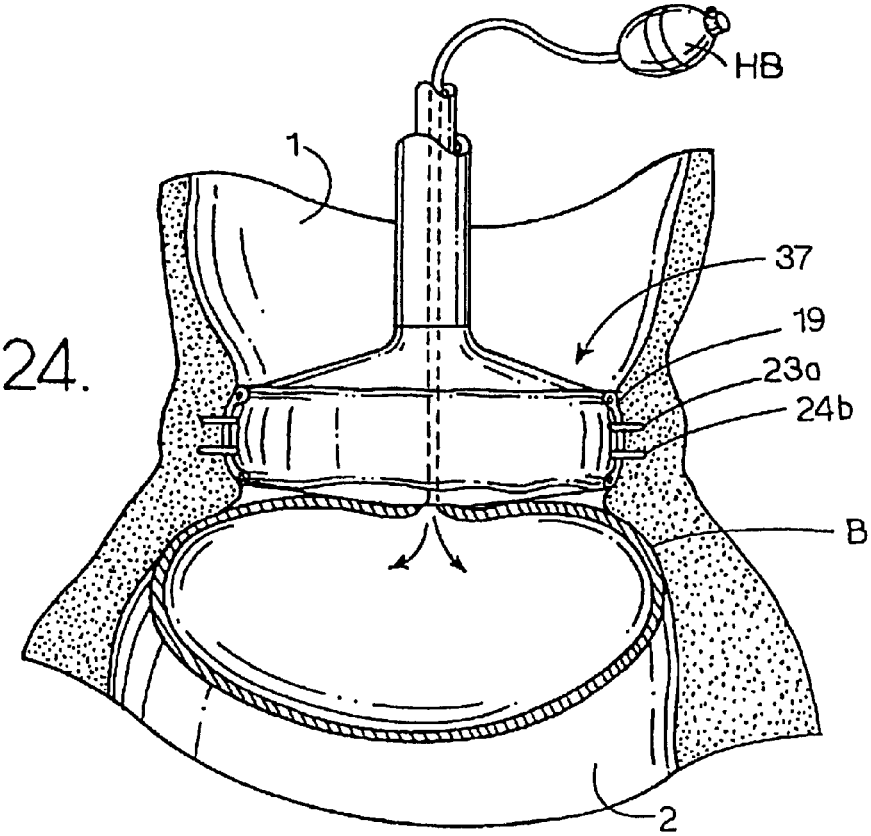
FIG. 24–27 show steps in placing a prosthesis.

During the installation of the fastener driving device, it will be important to obtain the correct anatomical positioning of the cuff to be fastened to the annular tissue. FIGS. 24–27 depict four different ways to accomplish this task. FIG. 24 shows the use of an inflatable balloon B in the left ventricle 2.

Figure 31:
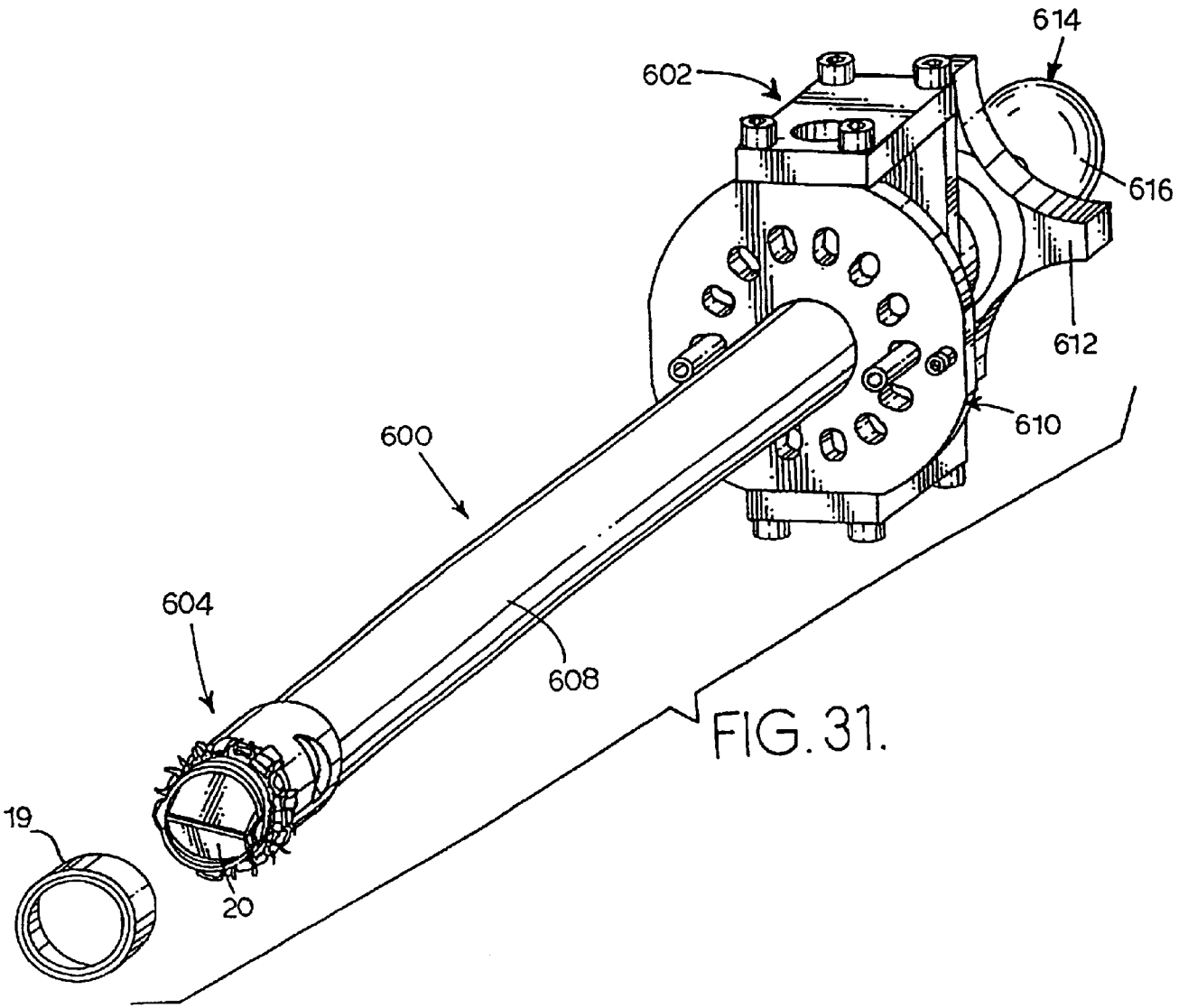
FIG. 31 is a perspective view of a staple delivery instrument.

As discussed above, there are times when a surgeon wishes to use an articulated or curved shaft to accommodate anatomical positioning of the instrument. As also discussed above, a curved shaft may be particularly advantageous in minimally invasive surgery where access to the proper fastening plane may be difficult or impossible with an instrument having a straight shaft. In such a case, instrument 600 shown in FIGS. 31, 36 and 37 is used to drive fasteners or staples radially outwardly. The advantage of the radial design is that it simplifies the delivery of longitudinal forces through the shaft of the instrument.

Referring to FIG. 31, it is seen that instrument 600 includes proximal end 602 that will be located outside the patient and which will be operated by the surgeon. Instrument 600 also includes a distal end 604 which will be located inside the patient and to which the cuff 19 will be attached and to which the heart valve 20 will be attached. A housing 608 can be articulated or flexible so the overall instrument can be bent as needed. Proximal end 602 contains an index mechanism 610 and a hand wheel 612.

As can be seen in FIGS. 31 and 41, a pre-fire rod 614 includes a handle 616 and a body 618 which is accommodated in a bore 622 defined through hand wheel 612 and through housing 608 to have its distal end 620 located near distal end 604 of the housing for a purpose that will be understood from the ensuing discussion. As will be understood, there are aligned bores in instrument 600 so pre-fire rod 614 will extend through instrument 600 from proximal end 602 thereof to distal end 604 thereof.

Index mechanism 610 includes a bracket 624 which is held stationary with respect to the patient during an operation. Bracket 624 is U-shaped and has two legs 626 which are connected together by a central leg 628. An index alignment plate 630 is attached to the distal ends of the legs 626 and includes a plurality of angularly spaced apart index alignment holes, such as hole 632. Housing 608 is attached to surface 634 of the index alignment plate 630. Holes 632 are spaced apart a predetermined angular spacing as determined by the needs of a surgeon as will be understood by one skilled in the art based on the teaching of this disclosure.

Two index pins, such as pin 638, are mounted on a lower surface 640 of a wedge cam driver plate 642 which has an upper surface 644. Plate 642 is rotatable with respect to plate 630 whereby index pins 638 can be moved from one index hole 632 to another index hole. Two wedge cams 646 and 648 are each attached at one end thereof to the driver plate 642 to rotate therewith and each has a wedge shaped distal end 650 and 652 respectively. Each distal end 650 and 652 has a terminal end, such as end 654 of end 648 and a surface, such as surface 656 of end 648, that slopes outwardly from end 654 along the longitudinal direction toward proximal end 602. As driver plate 642 is moved in longitudinal directions 660 and 662, ends 648 and 650 are moved in corresponding directions. The purpose of this movement will be understood from the ensuing discussion. Each of the wedge cams includes an inner edge 664 and 666 that is spaced apart from the corresponding inner edge of the other wedge cam so that a gap 668 is defined therebetween. Pre-fire rod 614 is accommodated in gap 668 so that distal end 620 of the pre-fire rod is located adjacent to ends 654 of the wedge cam bodies.

The pre-fire rod is forced in directions 660 and 662 by moving handle 616 in the desired direction. Wedge cams 646 and 648 are also moved in directions 660 and 662 by movement of driver plate 642. Driver plate 642 is moved by turning hand wheel 622 in directions 670 and 672. A threaded shaft 674 is attached to hand wheel 612 to be rotated thereby and includes a distal end connected to driver plate 642. Shaft 674 is threadably accommodated in leg 628 of the bracket 624 to move in directions 660 and 662 in response to the rotational movement of the hand wheel 612 in directions 670 and 672. Shaft 674 is coupled to driver plate 642 to move that plate in directions 660 and 662 but to rotate relative to the plate so the plate does not rotate with the hand wheel. A suitable de-coupling joint is used to effect the connection between shaft 674 and plate 642.

Operation of the fastening tool described thus far is understood from FIG. 41. Thus, the wedge cam sloping surfaces 652 are oriented by disengaging index pins 638 from alignment holes 632, rotating driver plate 642 until the index pins are aligned with the selected holes, and then operating hand wheel 612 to move in direction 660 until the index pins are suitably seated in the selected index holes. Pre-fire rod 614 is then forced through the longitudinal bore until distal end 620 thereof is suitably positioned. Further operation of either the pre-fire rod or the hand wheel will operate the fastener mechanism as will be described below.

As discussed above, the staple mechanism includes a plurality of staple assemblies 680 that are angularly spaced apart as shown in FIG. 36. The staple assemblies are also located in two rows that are spaced apart longitudinally of the instrument as indicated by rows R1 and R2. The assemblies are also offset so staples in row R1 are staggered with respect to staples in row R2.

Figure 32:
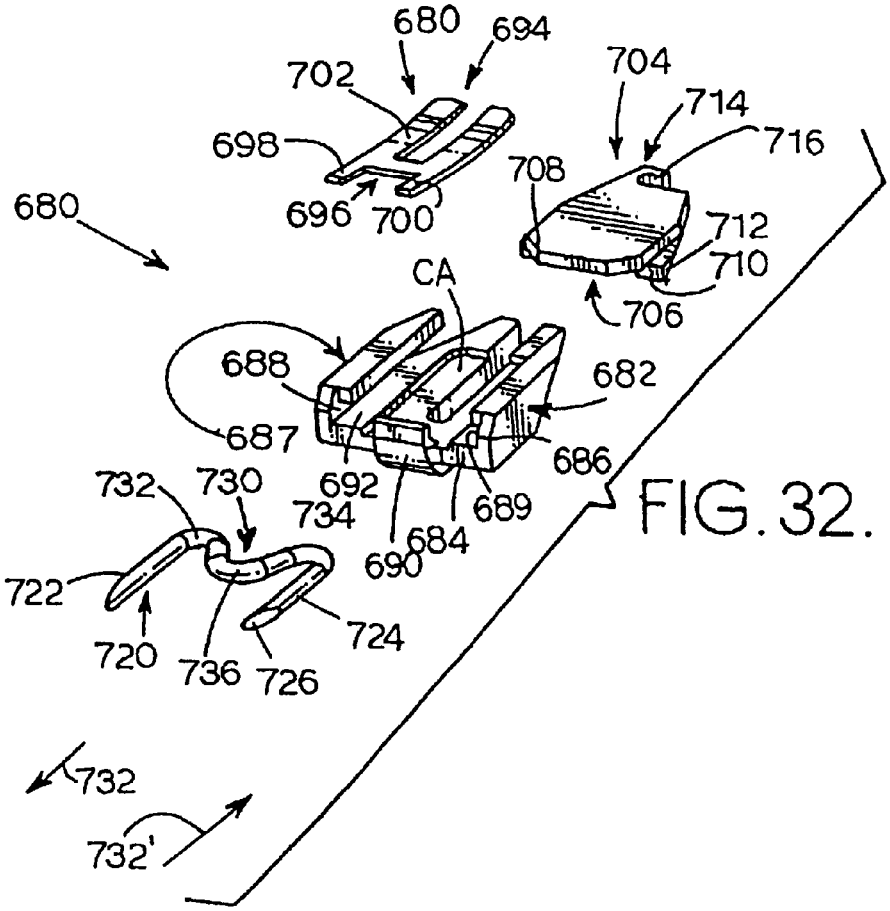
FIG. 32 is an exploded perspective view of a staple delivery assembly.

The assemblies are all identical therefore only one assembly will be described. As shown in FIG. 32, assembly 680 includes an anvil frame 682 having a base section 684 having sides 686 and 687 each having an inner surface 688 and 689 to define a cavity CA therebetween. A center anvil 690 is located centrally between the sides and extends upwardly above base surface 692. A lifter spring 694 is H-shaped and includes a U-shaped front end 696 with two legs 698 and 700 extending therefrom. Spring tabs 702 are located on the other end of each leg. The lifter spring is curved so front end 696 curves upwardly from base surface 692 when the lifter spring is seated thereon. Spring tabs 702 engage the anvil frame to hold the spring in place in the cavity CA. End 696 will be located adjacent to center anvil 690.

Figure 33:
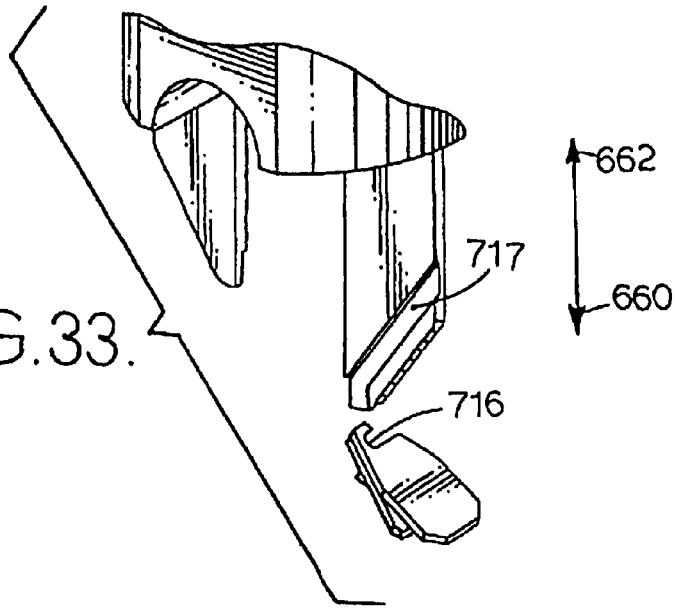
FIG. 33 is an exploded perspective view of a staple guide means for guiding movement of the staple delivery assembly shown in FIG. 32.

A driver 704 is wedge shaped and is received in cavity CA. Driver 704 includes a front edge 706 having two surfaces 708 and 710 thereon with a driver stop 712 on an undersurface thereof. The legs 708 and 710 will be located adjacent to center anvil 690 when the driver completes a fastener driving step as will be understood from the following discussion. An engaging element 714 extends rearwardly from the driver 704 and includes a hook 716 for engaging a corresponding groove 717 (see FIG. 33) defined in each of the wedge cams.

A W-shaped staple 720 is received in cavity CA and includes two legs 722 and 724, each having a sharp tip, such as tip 726 that is forced through the patient's tissue and through the cuff. The staple further includes a doubly curved center section 730 having a first curve 732 and 734 connecting each leg to the center section and a central curve 736. The central curve 730 is located to be engaged by center anvil 690 when the staple is forced in direction 732 by driver 704 engaging curves 732 and 734. Legs 722 and 724 slidably engage surfaces 688 and 689 to be held straight during the movement in direction 732 until the legs leave the anvil frame. Legs 722 and 724 are parallel and pierce the article being stapled before they are folded over through contact of the section 736 with center anvil 690.

As can be understood from the foregoing, as staple 720 is forced in direction 732, legs 722 and 724 move in direction 732 in sliding engagement with surfaces 688 and 689. After staple center section 736 engages center anvil 690, further movement in direction 732 causes the legs 722 and 724 to fold towards each other until they overlap each other. This is a two step movement of the staple: a first linear movement of the legs; and then a folding over of the legs. The first linear movement causes the legs to push through the tissue and the material of the cuff in a linear direction before the legs are folded over. Thus, the staple can take a significant bite our of the material an the tissue before folding. This is helpful if the tissue is hard or is covered with calcium.

The staple disclosed herein is narrow in its preform width and can resist gathering of the cuff and tissue during the forming process. Staple designs such as box staples gather and bunch material between the legs of the staples as they are formed. Bunching is inconsistent with the needs of this device. If a staple bunches, far too much material in the cuff is used (gathered) and by the time the staple pattern comes around to making a full circumferential line, the fabric is too tight and can pull away from the aorta wall.

Return movement of the assembly is indicated in FIG. 32 by arrow 732', and is caused by hook 716 being engaged in groove 717. The groove is sloped so that as the wedge cam is moved in direction 660, the driver is moved in direction 732, and as the wedge cam is moved in direction 662, the driver is moved in direction 732'.

An alternative form of the assembly is shown in FIG. 35 as assembly 680'. Assembly 680' is similar to assembly 680 except driver 704' includes a rear projection 734 and two forward projections 708' and 710' which engage curves 732 and 734 of the staple to drive the staple as described above. Assembly 680' includes a U-shaped lifter spring 702' which has two legs 698' and 700' with tabs 702' for engaging recesses 703 to hold the spring in the anvil frame. Assembly 680' is moved in direction 732 in the same manner as assembly 680, but includes a post 740 on top of a frame plate 742 that is fixed to the anvil frame. A garter spring 744 (see also FIG. 36) or the like is wrapped around the posts of the assemblies 680 to return them in direction 732'. Operation of assembly 680' is similar to the above-described operation of assembly 680.

Figure 34A:
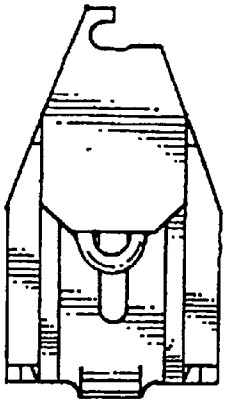
Figure 34B:
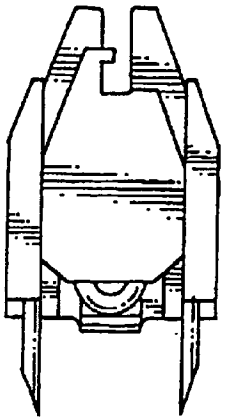
Figure 34C:
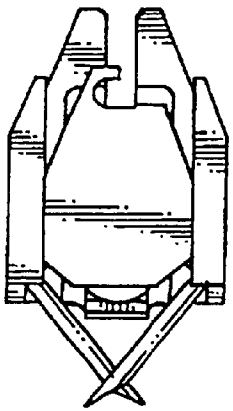
Figure 34D:
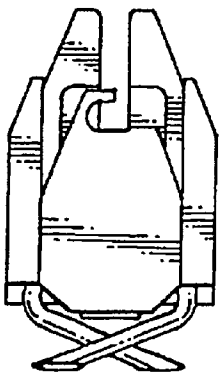
Figure 34E:
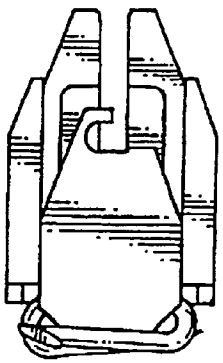
Figure 34A:
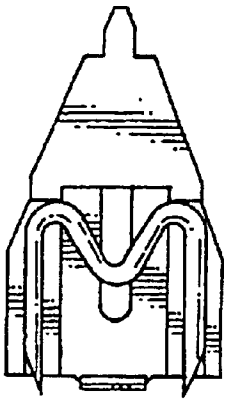
Figure 34D:
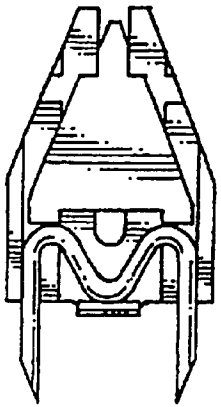
Figure 34D:
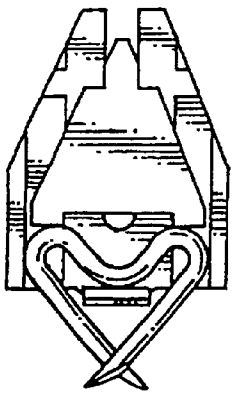
Figure 34D:
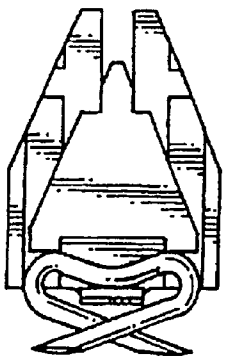
Figure 34E:
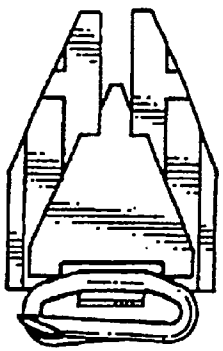

Operation of the staple is illustrated in FIGS. 34a–34e for assembly 680 and in FIGS. 34a'–34e' for assembly 680. Thus, FIG. 34a shows a staple in a nested position, FIG. 34b shows the first step in which the legs of the staple are pushed linearly out of the anvil frame to advance the staple, FIG. 34C shows the crown or central curve engaging the center anvil to initiate the folding of the legs, FIG. 34D shows the legs being folded over and FIG. 34E shows the staple in its final form.

Operation of the instrument can be understood from FIGS. 36, 37, 38, 39a–39d, and 40A–40C. As shown, a wedge cam body 750 is slidably received in housing 608 and has wedge cams 646 and 648 thereon. The wedge cams are inserted into a wedge cam alignment block 752 via slots, such as slot 754. The wedge cam alignment block 752 is fixed to a head 756 by fasteners, such as threaded bolt 758. Head 756 contains all of the above-described assemblies 680 or 680' in staggered rows R1 and R2.

Wedge cam driver plate 642 is moved in direction 662 to release index pins 638 from index alignment holes 632 which moves the wedge cams out of the slots 754. The driver plate 642 is then rotated in direction 670 or direction 672 to align index pins 638 with new index alignment holes and thus align the wedge cams with new slots.

Hand wheel 612 is then rotated to drive plate 642 in direction 660 to set the wedge cams in the slots near the rear ends of the staple drivers. Pre-fire rod 614 is then driven down in direction 660 to move anvil frames radially outward into a pre-fire position, such as shown for staple 720' in FIG. 36 which drives the staple through the cuff material and through the tissue. A frame stop 760 is located on the bottom of each anvil frame and engages a corresponding shoulder in the instrument to stop movement of the anvil frame in direction 732 when the prefire rod moves past the anvil frame. Hand wheel 612 is then operated to drive the wedge cams in direction 660 which drives the staples in direction 732. This drives the staple through the cuff and through the tissue and folds the staple legs over as above discussed. The lifter spring then moves the folded staple over the center anvil 690 to release the staple from the assembly. A plurality of staples are stored in the instrument so another staple is ready for deployment as soon as the operation is complete.

The hand wheel is then rotated in the opposite direction, the pre-fire rod moved in the opposite direction, and the staple assembly is moved back into its rest position.

Operation of the instrument is shown in FIGS. 39a–39d and 40A–40C. The results of the operation are indicated in FIG. 42 with three rows of staples being shown in a cuff 19. Once the staples are deployed, the heart valve can be moved onto the stapled cuff, and attached thereto as above discussed. This is illustrated in FIGS. 43–45. As shown in FIG. 38, the staples extend through the cuff and into the tissue before they are folded over. Thus, as shown for staple 720a the staple legs extend deep into the tissue to get full depth bite of tissue before folding, and the cuff is stretched over the tissue as shown for tissue AT.

As above discussed, there are times when a surgeon wishes to apply one staple at a time so better control over the number and placement of the staples can be exercised. This can be achieve using instrument 800 shown in FIGS. 46 and 47.

Instrument 800 fires one staple at a time and can be positioned as desired prior to firing the staple. As will be discussed below, using instrument 800, a surgeon can establish any desired stapling pattern, either one preset on the cuff or one that the surgeon makes up on the fly. It is noted that the operation of the staple and the staple forming assembly of instrument 800 is basically identical to the staple and staple forming assembly discussed above. Therefore, only the differences between instrument 800 and the above-described assembly will be discussed.

Instrument 800 includes a hand-grip section 802 on the proximal end thereof, and a staple forming and deploying assembly 804 on the distal end thereof with a shaft housing 806 connecting the two ends. Hand-grip section 802 includes a handle 808 on which a forming trigger 810 is pivotally mounted for movement in directions 811 and 811', with return spring 812 biasing the trigger in return direction 811'. A drive bar 814 is connected at a proximal end thereof to trigger 810 to be moved in directions 811 and 811' with the trigger. Drive bar 814 is located inside housing 806 and has a staple driver 704" on the distal end thereof. Staple driver 704" is part of a staple driving and forming assembly 680" which drives staple 720 toward center anvil 690" to move the legs of the staple outwardly and through the cuff and the tissue and then to fold the legs over as above discussed. A lifter spring 694" ejects the staple after it has been formed. A plurality of staples are stored in a housing 816 on the distal end of the shaft, and a spring biased magazine guide 818 urges the staples under a transfer spring 820 mounted on shroud 822 which biases the staples into position to be moved by the driver 704" upon actuation of forming trigger 810. Operation of the staple forming assembly will not be discussed as it was discussed above with reference to FIGS. 34a–34e'.

As shown in FIG. 47, distal end 804 is angled so a staple exits that end at an angle θ to the longitudinal centerline of the instrument. In the preferred embodiment, angle θ is an acute angle. A flexible section 824 between drive bar 814 and driver 704" permits the drive bar to move linearly while forcing the staple at an angle to that movement. The purpose of this angled discharge is to permit the surgeon to accurately locate the staple being driven in the exact position he desires. As will also be understood from the following discussion, this angled discharge permits the instrument 800 to be used in conjunction with a plurality of different systems.

As just mentioned, a surgeon may want to locate each staple individually. He may use a guide or he may simply locate on the fly. One form of stapling guide system, is shown in FIG. 48. Using this system, a cuff is first attached to the patient's tissue using the just discussed staple driving tool, instrument 800, in conjunction with a guide and support assembly 830. In the interest of clarity, a cuff that is installed on the patient separate from the heart valve will be referred to as an anchor ring. Once the anchor ring is installed on the patient, the heart valve is drawn to it in the manner discussed above, such as shown in FIGS. 43–45, for example. As shown in FIG. 48, an anchor ring 19' is releasably fixed to flexible fingers 832 of a cage, with the top of each finger being fixed to an index ring 834 and biasing outwardly from that ring. The anchor ring 19' is positioned on the lower ends of the fingers and is biased radially outwardly. The index ring 834 has lugs 836 that are fixed to a stationary stabilizer whereby the guide 830 is held stationary during the operation. The outward flex of fingers 832 force the ring 19' against the patient's tissue thereby ensuring a snug fit between the anchor ring and the patient's tissue, and can accommodate various sizes of aortas.

As can be seen in FIG. 48, anchor ring 19' includes a plurality of stapling icons, such as icon 838 to guide a surgeon in placing the staples. Using icons 838, a stapling pattern shown in FIG. 49 will be established in ring 19' with staggered rows R1, R2 and R3 of staples. To assist the surgeon in following the icons, index ring 834 includes a plurality of grooves, such as groove 840 which receive the instrument 800 and serve to position it with respect to an icon. If a surgeon wishes, he can staple in any pattern he wishes. This option is illustrated in FIG. 50 which shows a scalloped staple pattern that generally follows the natural cusp shaped curves of a valve annulus could be selected if desired. Other patterns could also be selected as will occur to those skilled in the art based on the teaching of this disclosure.

As above described, the legs of each staple are first extended to pierce the cuff and the tissue to approximate the cuff or anchor ring on the tissue, then the staple is formed. The instrument is removed from the vicinity of a formed staple and is moved to the next groove. Once the anchor ring is stapled to the patient, the cage 830 is removed and the heart valve is located to be attached to the anchor ring as above described.

A more automated system for placing an anchor ring on a patient is illustrated in FIGS. 51–53. This system uses the above described instrument 849 and includes one system for locating the anchor ring and a second system for automatically indexing the location of the staple placement. Both system are shown in FIGS. 51 and 52.

The anchor ring is placed in the patient by first system 850 which includes two arcuate expander shoes 852 each pivotally connected at pivot 853 to an expander arm 854 at an arcuate section 856 of that arm located near the distal end of the arm. A pivot 857 is located on the distal end of each expander arm, and the proximal end of each arm is located outside the patient during use. The surgeon grasps each of the expander arms near the proximal ends 858 thereof and manipulates these arms to expand the anchor ring against the patient's tissue. An O-ring 860 exerts a radially inward bias that opposes outward movement of the expander shoes. Cuff liners, such as cuff liner 860 are interposed between the expander shoes and the O-ring and contact the anchor ring. Cuff liners 862 serve as an outer circumferential edge of the system 849.

System 849 further includes a top guide element 864. Element 864 includes a central section 866 and two wing sections 868. Central section 866 accommodates the top end of guide tube 870 through which instrument 800 fits to be guided into stapling position within the patient. A key hole slot 871 can engage a key 872 (see FIG. 46) on housing 806 of instrument 800 to further control placement of the instrument. As can be seen in FIG. 52, the bottom end of guide tube 870 is positioned adjacent to the cuff liners and is angled with respect to the plane established by the expander arms. The angled nature of the staple discharge section discussed above thus places the staples in the proper position for discharge through the anchor ring and through the patient's tissue to attach the anchor ring to the tissue. Each element 864 further includes a plurality of ratchet teeth 870 that engage the expander arms to hold them in a selected location and orientation.

The tool shown in FIG. 46 has only one set of drivers and thus the mechanical complexity is low enough to make manufacturing efficient. Additionally, since manufacturing small parts is difficult, and small parts do not handle stresses well, the reduction in parts for the FIG. 46 tool is advantageous. Use of the system shown in FIG. 46 is evident from the disclosure herein, and thus will only be briefly discussed. Once the diseased valve is removed and the tissue is decalcified, the valve base alignment ring is placed down into the aorta and is held in place with the stabilizing arms. Next, the surgeon looks down through the aorta at the cuff and uses the serrations on the inside of the ring to guide the staple driving tool toward the cuff. He then extends the legs of the staple beyond the distal end of the driving instrument and places the staple according to the icons on the cuff. He then pushes the staple legs through the cuff to penetrate the aortic tissue thereby approximating the cuff to the tissue. Subsequently, he forms the staple with the staple forming device and then removes the device. The device is then moved to the next serration, thereby stabilizing the top edge of the staple driving shaft and then places the protruding staple legs into the next printed icon. The process is continued until either a helical or circular staple pattern is established. The process is completed when at least two overlapping rows of staples are formed in the cuff.

Once the anchor ring is securely stapled in place, the cuff is released from its attachment to the expander by cutting sutures and the tool is removed. Docking sutures which were pulled up out of the body cavity during the staple forming procedure are then sewn into the heart valve cuff and the valve is lowered into place either within the circumference of the anchor ring or superiorly depending on the configuration of the heart valve prosthesis. If the surgeon wants to adjust the superior/inferior placement he may do this by altering the placement of the docking sutures in the heart valve cuff.

The second element of the instrument 849 automatically indexes the location of the staple delivery. The second element includes a base 872 that is located within the cuff liner and includes a central internally threaded hole 874 and two pivot connections 876 to which pivots 857 of the expander arms are connected. The thread in hole 874 is helical for a purpose that will be discussed below. An idler plate 878 is mounted on base 872 by pivot pin 880 being inserted into hole 882 defined in base 872. An idler 884 is rotationally mounted on idler plate 878 and is engaged by index gear 886 that is also rotationally mounted on idler plate 878. An idler plate spring 888 is mounted at one end thereof on base 872 and at the other end thereof to idler plate 878 and is held in place on base 872 by spring 889 mounted on base 872. Index gear 886 is connected to a distal end of index drive shaft 890, with the proximal end of shaft 890 being attached to an index wheel 892. Index wheel 892 is rotationally mounted to element 864 at a central location 894 having index indicators 896 thereon. Index drive shaft 890 is rotated by rotation of index wheel 892, with index indicators providing a visual indication of the amount of rotation undergone by the index drive shaft. As shown, rotation of index gear 856 in direction 897 causes corresponding rotation of idler 884 in direction 897'. Idler 884 is engaged with flexible gear rack 900 which is held in place on the cuff liners to engage the idler 884 to be moved in direction 897" upon rotation of the idler in direction 897'. Flexible gear rack 900 is fixed to base 872. Since alignment tube 870 is fixed to base 872, tube 870 will rotate with the base.

As shown in FIG. 53, heart valve HV is attached to cuff 19 and to heart valve base holder 902. Base holder 902 includes arms 904 radiating outwardly from central section 906 on which an externally threaded projection 908 is mounted. Thread groove 910 is helical and matingly engages thread 912 defined on base 876 adjacent to hole 874. A retainer spring 914 ensures proper engagement between threads 910 and 912. Valve base holder 902 is released from the heart valve by operating release lever 916 connected to release shaft 918 to lift the shaft 918 upwardly. Lifting release shaft 918 causes fingers 904 to rotate inwardly to release the anchor ring from the holder 902. The anchor ring is firmly secured to the patient when the release lever is operated and the inwardly rotated arms are flexible enough to move past the fixed anchor ring.

It is noted that the anchor ring is fixed to the patient by the outward flexing of the arms 904, and an initial staple can be placed to further fix the anchor ring to the patient to begin the process. Thus, any item fixed to the anchor ring is fixed, and any other element will move with respect to the anchor ring after that ring is initially fixed to the patient. Thus, since the base 872 is not fixed to the anchor ring, it will rotate with respect to the anchor ring, while base holder 902 is fixed to the anchor ring. Thus, rotation of shaft 890 rotates the base 872 with respect to holder 902. Since holder 902 is threadably engaged with base 872, rotation of base 872 causes the base to move longitudinally on the holder 872. Thus, base 872 moves both rotationally and longitudinally on the cuff or anchor ring. The staple delivery location, being fixed to the base, thus moves both rotationally and longitudinally with respect to the cuff. Such simultaneous rotational and longitudinal movement causes the staple delivery location to describe a helical path on the fixed cuff. Such a helical path is shown in FIGS. 54A–54C, for various sizes of staples and various staple spacings (21 mm spacing in FIG. 54A, and 21.5 mm spacing in FIG. 54C). This helical path permits a single line of staples to be set without unwanted gaps and with any degree of overlap desired.

The system shown in FIG. 51 assures that each staple is placed with the proper spacing between staples and that the rows are properly spaced. In addition, this alignment procedure is very forgiving and is adjustable to aorta diameter. This is because staples can be spaced apart a linear distance instead of an arcuate distance. The staples are placed in a single continuous row which takes the form of a helix to complete overlapping multiple rows when the line is long enough to complete two or more revolutions of the helix. It additionally allows the second revolution of the line to be placed much closer to the first revolution because the line is not constrained by packaging multiple driver assemblies. The line distance is regulated only by how fine or coarse the helix angle is on the index mechanism.

Use of the FIG. 51 system is evident from the above disclosure and thus will only be summarized. The surgeon advances the staple in the tool to expose the straight legs of the staple, The straight legs of the staple are then pushed through the cuff to penetrate the aortic tissue.

Once the surgeon has felt the penetration of the staples into the tissue, he then forms the staple. Once the staple is formed and the lifter spring has lifted the staple off of the anvil, the staple driving tool is removed from the receptacle. While holding on the proximal end of the tool, the index wheel is rotated one-half of a full rotation as indicated by colored markers on the index wheel as seen through the index wheel indicators. The staple driving tool is then again inserted into the staple alignment receptacle and keyed to maintain staple alignment. Once again, the staple legs are advanced forward and penetrated through the cuff and the annular aortic tissue, then the staple is fully formed. This process is repeated until two full rotations of the indexing base are accomplished, thus providing two overlapping helical rows of staples.

One form of the device has the timing wheel held within the indexing mechanism. The first step is to place the valve base and the cuff into the aorta with the index valve holder. The second step is to dilate the cuff and make it snug against the aorta by using the dilation control on the index valve holder. The internal platens, which press the cuff against the annulus expand. By expanding these platens, the indexing mechanism takes on the diameter of the distal section. This calibrates the indexing mechanism for the specific annulus size. An incremental movement of the index planetary gear will make certain that the receptacle has indexed the proper amount to ensure that the next staple is fined precisely one increment from the previous staple, independent of annulus size. As the index mechanism is shifted to the next position, the planetary gear ensures that the mechanism will place the receptacle one increment away. After the staple driving device has fired the first staple, the driving device is removed from the instrument and the index holder is indexed to the next position. If desired, the device can form two rows of staples by extending the index feature to an upper position after firing a first row of staples.

With regard to the index gear 886, it is noted that each one-half rotation thereof provide one staple increment. The index spring on the base signals the user when the index gear has made one-half of a revolution through an audible tactile "click." Further note that the flexible gear rack is connected at one end to one of four cuff linear parts and is allowed to float freely from thereon thereby allowing the index gear rack to expand as the expander arms push on the cuff liners to accommodate larger or smaller sizes of aorta. In addition, the gear rack is taller than the index gear in order to allow the index gear to continue to engage the index rack as the alignment tube plate rises up the threads to produce the helical pattern. It is also noted that the expander arms are made of a slippery polymer to reduce friction with the cuff liners. Each shoe, through a small dovetail, engages at least two cuff liners.

A further use of the instrument 800 is illustrated in FIGS. 55 and 56 for closing the aortomy 920. This procedure is achieved using staples alone. The surgeon approximates the incised edges of the aorta with forceps 922, and tool 800 is placed next to the approximated edges and operated to deploy a staple. Due to the dual movement of the staple discussed above, the legs of the staple move through the tissue before they are folded over. As they fold over, the edges are brought together so formed staple 720f closes the incision as shown in FIG. 56.

As discussed above, the primary requirement for a fastener in the context of the present invention is to be individually placable and which locally approximates and cinches the tissue from the operative side of the tissue.

The related applications referenced above disclose means and methods for replacing a heart valve in which a flexible cuff is fixed to a patient's tissue and a prosthesis valve is then docked to the in-place cuff. Fasteners, such as staples, which have their shapes permanently changed by a tool are disclosed in these related applications. However, the cuff mounting procedure taught in these related applications, based on the teaching of these applications, can be carried out using a variety of fasteners including, but not limited to, the permanently altered fasteners mentioned above, fasteners which have their shapes changed by a tool during the process but which return to their initial shapes once they are fixed to the patient, and fasteners which do not have their shapes altered by a tool during the cuff-attaching process. The following disclosure discusses the latter two fastener types.

The fasteners of the present invention, like nearly all surgical materials, obey Hooke's law. That is, if they are subjected to a gradually increasing stress, the ratio of the unit stress to the unit strain or deformation, is constant until a certain limiting value of the unit stress, known as the proportional elastic limit, is reached, see, e.g., "The Making, Shaping and Treating of Steel" 10th Edition, edited by William T. Lankford, Jr., Norman L. Samways, Robert F. Craven and Harold E. McGannon and Published by US Steel and the Association of Iron and Steel Engineers in 1985, the disclosure of pages 1389–1446 (Chapter 50) being incorporated herein be reference, see also the definition of Hooke's law in the McGraw-Hill Dictionary of Scientific and Technical Terms, published by McGraw-Hill Book Company in 1974 and edited by Daniel N. Lapedes (the disclosure of which is incorporated herein by reference), which defines Hooke's Law as "the law that the stress of a solid is directly proportional to the strain applied to it, "elastic deformation" as "reversible alteration of the form or dimensions of a solid body under stress or strain," and conversely "elastic failure" as "failure of a body to recover its original size and shape after a stress is removed," "elasticity" as "the property whereby a solid material changes its shape and size under action of opposing forces, but recovers its original configuration when the forces are removed," and "elastic limit" as "the maximum stress a solid can sustain without undergoing permanent deformation."

Surgical fasteners can be treated within their elastic limit. In this regard, elastic limit is defined in standard references, such as "Mechanics of Materials" by Seibert Fairman and Chester S. Cutshall, published by John Wiley & Sons in 1953, the disclosure of Chapters 1 and 2, pages 1–32, being incorporated by reference, as the maximum stress that may be applied without producing a permanent set. Such fasteners will be referred to herein as elastic fasteners. With elastic fasteners, no permanent set occurs until after the proportional limit is reached, and the ratio of stress to corresponding strain for stress below the proportional limit is defined by ASTM as the modulus of elasticity.

Three types of fasteners that can be used to attach a prosthetic reinforcing cuff to an annulus of an existing valve have been disclosed. The first type of fastener disclosed requires a forming step that transfers a force to the fastener that causes the fastener to exceed its elastic limit thereby changing the actual shape and size of the fastener. The second type of fastener acts more like a spring in which it initially changes shape within its elastic limit and returns to the original shape of the fastener once application is completed. The third type of fastener does not operate in the elastic range at all, thereby not changing shape in any way thus is a "self-retaining" fastener. It maintains its dimensional status throughout the application of the fastener.

As mentioned above and in U.S. Pat. No. 5,716,370, the disclosure of which is incorporated herein by reference, the first type of fastener uses an installation tool which imparts a force on the fastener causing it to exceed its elastic limit during application thereby physically changing the actual shape and size, and thus is a "tool formed" fastener. The definition of "elastic limit" in the McGraw-Hill Dictionary of Scientific and Technical Terms, published by the McGraw-Hill Book Company in 1974 and edited by Daniel N. Lapedes (the disclosure of which is incorporated herein by reference) is "the maximum stress a solid can sustain without undergoing permanent deformation." Thus, from the foregoing, it can be understood that for materials such as the fasteners of the present disclosure, which obey Hooke's Law, which is "the stress of a solid is directly proportional to the strain applied to it," permanent physical changes resulting from stressing the fasteners will disappear when the stress is removed providing the stress does not exceed the proportional elastic limit. After this limit is exceeded resulting strain does not entirely disappear when the stress is removed. The part of the strain that remains is called the permanent set. A surgical staple an example of a fastener that surpasses its elastic limits and deforms during the attachment of a prosthesis to an annulus.

The second type of fastener disclosed as a non-anvil formed fastener and is a fastener that does not exceed its elastic limit and does not take a permanent set when used in attaching the prosthetic reinforcing cuff to the annulus of an existing valve in the patient, and thus is referred to as a highly elastic fastener. These fasteners experience what is known as "elastic deformation" which is defined as "reversible alteration of the form or dimensions of a solid body under stress or strain." That is, they have the ability to regain their original, or initial shape and dimension, whatever that is, after experiencing a change of shape and/or size, also known as strain, due to the application of external forces as long as the external forces do not exceed the "elasticity" which is defined as "the property whereby a solid material changes it shape and size under action of opposing forces, but recovers its original configuration when the forces are removed." When an elastic material is used in this application it can temporarily change shape during the process of attaching the prosthesis to an annulus and once attached the fastener will retain the shape it had prior to attachment.

The third type of fastener does not see enough force to experience any elastic deformation or even obtain elasticity whatsoever, and is referred to as a self-retaining fastener. This fastener maintains its original shape and dimensions throughout the fastener application. This is also considered to be a non-anvil formed fastener, based on a certain amount of force being applied to it during the application of the prosthetic cuff but not enough to cause any dimensional change whatsoever. An example of a non-anvil formed fastener that does not operate in the elastic range is a self-tapping helical fastener or a barbed fastener.

Still further, since the present disclosure refers to fasteners such as staples that have been stressed beyond their elastic limit whereby when the stressing force is removed the fasteners retain their stressed shape and do not return to their initial size and/or shape, as being "tool-formed," a fastener that has not been stressed beyond its elastic limit and thus will return to its initial size and/or shape when the stressing force is removed will be referred to as a "non-formed" or "elastic" fastener. In other words, a non-formed fastener is a fastener that has been stressed during a surgical procedure, such as covered in the present invention, yet is not permanently deformed by such stress and will return to its initial size, shape and dimensions when the stressing force is removed.

With regard to tool-formed fasteners, in order to set a tool-formed fastener to hold a cuff on a patient, a fastener such as a staple is stressed by a tool and anvil combination beyond the elastic limit of the fastener whereby once the forming force (the external stress) is removed the fastener will not regain its original shape and will be permanently deformed. Elastic limits for most materials, including those used in the fasteners of the present invention, are well documented in standard references, such as in Table X of the above-referenced "Mechanics of Materials," the disclosure of which is incorporated herein by reference, as well standard handbooks such as "Marks' Standard Handbook for Mechanical Engineers" Seventh Edition Edited by Theodore Baumeister and published by McGraw-Hill Book Company in 1967, Chapter 5, the disclosure of Chapter 5 being incorporated herein by reference, as well as the incorporated US Steel Book. By way of example, the US Steel book discloses the mechanical properties of stainless steel on pages 1345–1355, the disclosure of which is incorporated herein by reference, including the yield strength thereof (see Table 47), see also the incorporated Mechanical Engineers Handbook, Table 19 (the disclosure of which is incorporated herein by reference) while the mechanical properties of Titanium are disclosed in the incorporated Mechanical Engineers Handbook (see Table 21 on page 6–101), the disclosure of which is incorporated herein by reference. Still further the incorporated "Mechanics of Materials" reference includes typical stress-strain diagrams for steel in FIGS. 26 and 27 on page 25, the disclosure of which is incorporated herein by reference, that show the proportional limits and illustrate Hooke's law.

The above discussion concerned a tool-formed fastener. As discussed above, the present invention also encompasses elastic fasteners which can achieve the result of attaching a cuff to a patient without being permanently deformed during or by the attaching process or the tools or instruments used to carry out the process. That is, the results of the present invention can be achieved using fasteners which, although stressed by the tool used and during the process of attaching the cuff to the patient using the fastener are not stressed beyond the elastic limit thereof whereby once the cuff-attaching procedure is completed and the tool removed from the fastener, the fastener will regain its original shape and dimension and will not be permanently deformed, or non-formed.

FIGS. 57, 61, 63, 64 and 66 illustrate embodiments of the non-formed (not permanently deformed by the stresses associated with carrying out the valve replacement procedures of the present invention) fastener which achieves these objectives, while FIGS. 58–60, 63 and 67–68 illustrate elements which can be used, either alone or in combination with tools disclosed hereinabove, to place these fasteners in a patient to attach a cuff to the patient without causing either the tool or the process to apply stress to the fastener sufficient to permanently deform the fastener from its initial shape. That is neither the tool nor the process applies stress to the fastener beyond the elastic limit of the fastener whereby the fastener is non formed and will return to its initial size, shape and dimensions after the sewing cuff is attached to the patient using the fastener. This is opposed to the staple form of the fastener discussed above which is permanently deformed during the cuff-attaching process, that is, the staple configuration of the fastener is "formed."

As shown in FIG. 57, a pre-stressed fastener 1000 is shown in its initial shape and is monolithic and includes two legs 1002 and 1004 which overlap each other adjacent to tissue penetrating points 1006 and 1008 respectively. In a free condition, the legs overlap each other as shown in FIG. 57. Fastener 1000 is used by storing it in the free condition such as shown in FIG. 57, then spreading the legs apart as indicated in FIG. 58 by fastener 1000' before placing and inserting the fastener into and through the prosthesis and tissue to be connected. The legs are held apart until the fastener has been placed, and then the legs are released. The procedure does not exceed the elastic limit of the fastener and thus the natural resiliency of the fastener causes the legs to regain the FIG. 57 initial overlapping orientation thereby cinching the prosthesis and tissue together. Fastener 1000 is formed of highly elastic material, such as nitinol or stainless steel spring wire, or the like having a shape memory and is not deformed beyond its elastic limit by either the tool or the procedure used to attach a cuff to a patient.

A tool element $\mathbf{1000}_T$ is shown in FIGS. 58–60 and is used to place and set fasteners 1000. Tool element $\mathbf{1000}_T$ is used with a tool that imparts longitudinal movement thereto. Any tool discussed above can be adapted to impart such longitudinal motion in a minimally invasive surgery environment. Referring to FIG. 58, tool element $\mathbf{1000}_T$ includes a fastener track 1010 supported on a tip retractor 1012 and having a cover 1014 thereon. Fasteners 1000 are stored in track 1010 and move downwardly in the track 1010 under influence of either a spring-loaded pusher bar or advancing mechanism associated with the operating tool. After the fastener reaches the end of the track, it drops off of the track as can be seen in FIG. 59, and onto two extender pins 1016 and 1018, best shown in FIG. 60. A hold-down spring 1020 keeps the fastener properly oriented. Hold down-spring 1020 also moves a fastener off the track into position to be opened against pins 1016 and 1018. A retractor back up element 1022 is moved by the longitudinally moving tool and forces the fastener against the pins 1020 to open the legs into the position shown for fastener 1000'. Once the fastener is forced through the prosthesis and tissue, the tool element $\mathbf{1000}_T$ is twisted to withdraw it from the fastener. As soon as tool element $\mathbf{1000}_T$ is withdrawn, legs 1002 and 1004 move toward the overlapping position and cinch tissue and prosthesis together.

As above discussed, the present invention also encompasses self-retaining fasteners, and shown in FIG. 61 is one embodiment of such a self-retaining fastener, and is a helical fastener 2000 which also fulfills the above-discussed criteria for fastening a prosthesis to a patient and does not experience permanent deformation during or after the cuff-attaching procedure described herein. Fastener 2000 includes a polygonal head 2002 and a central body 2004 with a helical element 2006 thereon. Element 2006 is in the nature of a screw thread, and upon rotating fastener 2000 in the manner of a screw, fastener 2000 acts like a self-tapping screw to force itself into and through a prosthesis and tissue to which the prosthesis is being attached.

A tool element $\mathbf{2000}_T$ suitable for use with rotational fastener 2000 is shown in FIG. 62. Tool element $\mathbf{2000}_T$ can be used with any tool that imparts rotational motion thereto. Tool element $\mathbf{2000}_T$ includes a rotation driver element 2010 which is connected to an element of the operating tool and is located inside a driver tube 2012 and is connected thereto to impart rotation thereto as indicated by arrow 2014. Driver tube 2006 fits over polygonal head 2002 to transfer this rotational motion to fastener 2000 which is located inside an extender tube 2016.

An operating tool $\mathbf{2000}_{TR}$ is used to impart rotational motion to the driver element 2010 and is shown in FIG. 69 as including a housing 2030 having a proximal end 2032 and a distal end 2034. Tool $\mathbf{2000}_{TR}$ translates linear motion of handle 2036 into rotational movement of driver shaft 2038 which is operatively connected to driver tube 2012 which has a polygonal inside shape 2040 to match the polygonal shape of head 2002. Fasteners 2000 are located inside tube 2012 to have rotational motion imparted thereto.

Handle 2036 moves in direction 2042 relative to stationary handle portion 2044 about a pivot axis 2046 so end 2048 of handle 2036 moves in direction 2050. End 2048 includes an elongated slot 2052 in which a pin 2054 is located. Pin 2054 is mounted on a follower sleeve 2056. Sleeve 2056 is constrained so sleeve 2056 moves linearly in direction 2058 when handle 2036 is moved in direction 2042. A second pin 2060 is mounted on sleeve 2056 and moves therewith. Sleeve 2060 is located around a driver element 2062 having a helical groove 2064 defined therein to receive pin 2060. Driver element 2062 is rotatably mounted in housing 2030 by mounts 2066 and flange 2068 so it can rotate but not translate under the influence of pin 2060 in groove 2064. Rotation of driver element 2062 is indicated by arrow 2070.

Driver element 2062 is operatively connected to shaft 2038 by one-way pawl mechanisms 2072 and 2074 so rotation in the desired direction is transmitted. Pawl mechanism 2074 transmits rotational movement of element 2062 to element 2038, while mechanism 2072 prevents retrograde motion when handle 2036 is moved in the direction opposite to direction 2042. Tool $\mathbf{2000}_{TR}$ also includes a stationary sleeve 2076.

Using tool $\mathbf{2000}_{TR}$ in connection with tool element $\mathbf{2000}_T$, fasteners are deployed in the center of the rotating tube. The rotating tube has a distal end which has a jaw assembly to hold the fasten which will extend from the end of the instrument as it is driven into the prosthesis and tissue. In addition, there is an indexing mechanism which advances one fastener at a time into the driving jaw assembly. Rotational mechanisms in the housing then rotate both the storage tube and the jaw assembly upon actuation of the handle as above described. The helix essentially screws its way into the tissue. Once the tissue bunches up against the head of the fastener, it compresses the tissue to the prosthesis thereby creating a seal. Other fastener forms can also be used without departing from the scope of this disclosure which use a load bearing surface and tissue gathering means and which are not permanently deformed by or during the cuff-attaching process so they will regain their initial shape and/or size after completion process. By this, it is meant that there are essentially two components of such a fastener, a crown surface which stays on the outside of the object to be fastened and the fastening mechanism or extension legs which penetrate through the fastening media into the tissue to grip the tissue. Yet another form of this non-permanently deformed helical fastener is shown in FIG. 63 as fastener 2000' having a polygonal head $\mathbf{2000}_H$ and a helical body 2080 attached at one end thereof thereto and having a point 2082 at the other end thereof.

Yet another form of such non-permanently deformed fastener is shown in FIG. 64 as fastener 2000". Fastener 2000" includes a head $\mathbf{2000}_H'$ having a knurled outer edge 2090 and to which a helical element 2092 is attached. Element 2092 has a penetrating point 2094 on the distal end thereof and regains its initial shape after completion of the surgical process because neither the process nor the tools used in the process applied sufficient stress to the fastener to exceed the elastic limit of the fastener.

Yet another fastener which is not permanently deformed by or during the process involving the fastener is shown in FIG. 65 as barbed fastener 2000'" which includes a head 2100 to which a central base 2102 is attached. Base 2012 has a pointed end 2104 and anti-back up barbs 2106 mounted thereon. Barbs 2106 extend in a direction opposite to point 2104 so once the fastener is set, the barbs will prevent it from moving in an opposite direction. A centrally located hole 2110 receives a point 2104 of an adjacent fastener so the fasteners can be stored as indicated in FIG. 67 in a delivery tool element $\mathbf{2000}_T'''$. Tool element $\mathbf{2000}_T'''$ is shown in FIGS. 67 and 68 as including a housing 2112 having a proximal end 2114 and a distal end 2116. Slots 2118 and 2120 are defined in end 2114 to slidably receive an advance bar 2122 that is moved longitudinally by a tool operating element that imparts such longitudinal movement in a minimally invasive surgical setting. Bar 2122 abuttingly contacts an antibackup ratchet 2124 on which fasteners 2000'" are releasably mounted. Fastener advance ratchets 2126 are oriented in the manner of barbs 2106 to allow a fastener to move past the ratchet but to prevent reverse movement of such fastener. Bar 2122 is forced downwardly into housing 2112 in direction 2123 and forces the fasteners to exit end 2116 between arms 2128 and 2130. Fasteners slide over the arms and when set in the tissue or in the prosthesis, or both, the arms prevent the fastener from moving backwards in direction 2123'. The tool element is then withdrawn and the fastener remains in place. An antibackup post 2132 is also mounted on housing 2112.

A further form of non-permanently deformed fastener 2000'" is shown in FIG. 66 as fastener $\mathbf{2000}^{IV}$ which includes a circular base 2140 having a base 2102 on one side and a post 2142 on the other side. Base 2102 has a point 2104 on one end and antibackup barbs 2106 adjacent to the point as discussed above for fastener 2000'". Post 2142 is attached to base 2140 by a one-way crimp 2144 and has a removable portion 2146 connected to the base by a frangible joint 2148. Fastener $\mathbf{2000}^{IV}$ is used in the manner of fastener 2000'", is not stressed beyond its elastic limit during or by the process and thus the use and operation thereof will not be discussed. Removable portion 2146 is used to place and set the fastener, and is then removed once the fastener is set. A tool driver is connected to portion 2146 in the manner of element $\mathbf{2000}_T'''$.

It is understood that while certain forms of the present invention have been illustrated and described herein, it is not to be limited to the specific forms or arrangements of parts described and shown with the elements being shown, such as the tool T, being the best mode, but not the only mode.

We claim:

1. In combination:

A) a multipart prosthesis which includes
(1) a flexible sewing cuff,
(2) a prosthesis valve separate and spaceable from said flexible sewing cuff, and
(3) means for securely attaching said prosthesis valve to said flexible sewing cuff after said flexible sewing cuff has been attached to a patient; and B) a tool for attaching said flexible sewing cuff to the patient in a minimally invasive manner and which includes
(1) a housing,
(2) an operating handle mounted on one end of said housing,
(3) at least one fastener stored in said housing, said fastener having an elastic limit,
(4) means for releasably mounting said flexible sewing cuff to said tool, and
(5) a fastener handling means on said housing and operationally connected to said operating handle to be controlled by said operating handle for storing said fastener and securing said fastener through said flexible sewing cuff and into the patient's tissue from one side of said sewing cuff and the tissue to attach said flexible sewing cuff to the patient without deforming said fastener beyond its elastic limit.

2. The tool defined in claim 1 further including means for separating the tool from the prosthesis.

3. In combination:

A) a multipart prosthesis which includes
(1) a flexible sewing cuff,
(2) a prosthesis valve separate from said flexible sewing cuff, and
(3) means for attaching said prosthesis valve to said flexible sewing cuff after said flexible sewing cuff has been placed in a patient; and B) a tool for placing said flexible sewing cuff in the patient in a minimally invasive manner and which includes
(1) a housing,
(2) an operating handle mounted on said housing,
(3) at least one fastener stored in said housing, said fastener having an elastic limit,
(4) means for releasably mounting said flexible sewing cuff to said tool, and
(5) a fastener handling means on said housing and operationally connected to said operating handle to be controlled by said operating handle for storing said fastener and securing said fastener through said flexible sewing cuff and into the patient's tissue from one side of said sewing cuff and the tissue to attach said flexible sewing cuff to the patient without deforming said fastener beyond its elastic limit.

4. The combination defined in claim 3 wherein each fastener of the tool includes a tissue-penetrating portion and anchoring means on said tissue-penetrating portion for anchoring said tissue-penetrating portion after the tissue-penetrating portion has passed through the patient's tissue.

5. The combination defined in claim 4 wherein the tissue-penetrating portion includes two legs and the anchoring means includes a spring base which is biased to force the legs of the [tissue-penetrating. portion] *tissue-penetrating portion* into a position in which the legs overlap each other.

6. The combination defined in claim 3 wherein the fastener of the tool includes a helical portion.

7. The combination defined in claim 3 wherein each fastener of the tool includes a tissue-penetrating portion which includes anti-backup barbs.

8. The combination defined in claim 3 wherein said fastener handling means [includes] of the tool *includes* means for storing fasteners and means for opening fasteners.

9. The combination defined in claim 3 wherein said fastener handling means [includes] of the tool *includes* means for storing fasteners and means for imparting rotation to said fasteners.

10. The combination defined in claim 3 wherein said fastener handling means of the tool includes means for storing fasteners and means for advancing fasteners one at a time.

11. The combination defined in claim 1 further including means for operating said operating handle which includes a housing; a handle pivotally mounted on said handle; means for translating pivoting movement of said handle into rotational motion; and means for connecting the translating means to a fastener.

12. In combination:

A) a heart valve prosthesis which includes
  (1) a flexible sewing cuff,
  (2) a prosthesis valve body separate from said flexible sewing cuff, and
  (3) means for securely attaching said valve body to said flexible sewing cuff after said flexible sewing cuff has been placed in a patient; and B) a tool for placing said flexible sewing cuff in the patient in a minimally invasive manner and which includes
  (1) a housing,
  (2) an operating handle mounted on said housing,
  (3) at least one fastener stored in said housing, said fastener having an elastic limit,
  (4) means for releasably mounting said flexible sewing cuff to said tool, and
  (5) a fastener handling means on said housing and operationally connected to said operating handle to be controlled by said operating handle for storing said fastener and securing said fastener through said flexible sewing cuff and into the patient's tissue from one side of said sewing cuff and the tissue to attach said flexible sewing cuff to the patient without deforming said fastener beyond its elastic limit.

13. In combination:

A) a multipart heart valve prosthesis which includes
  (1) a flexible sewing cuff,
  (2) a prosthesis heart valve body separate from said flexible sewing cuff,
  (3) means for attaching said heart valve body to said flexible sewing cuff after said flexible sewing cuff has been placed in a patient; and B) a tool for placing said flexible sewing cuff in the patient in a minimally invasive manner and which includes
  (1) a housing,
  (2) an operating handle mounted on said housing,
  (3) at least one fastener stored in said housing, said fastener having an elastic limit,
  (4) means for releasably mounting said flexible sewing cuff to said tool, and
  (5) a fastener handling means on said housing and operationally connected to said operating handle to be controlled by said operating handle for storing said fastener and securing said fastener through said flexible sewing cuff and the tissue to attach said flexible sewing cuff to the patient without deforming said fastener beyond its elastic limit.

14. In combination:

A) a heart valve prosthesis which includes
  (1) a flexible sewing cuff,
  (2) a prosthesis valve separate from said flexible sewing cuff, and
  (3) means for securely attaching said valve to said flexible sewing cuff after said flexible sewing cuff has been placed in a patient; and B) a tool for placing said flexible sewing cuff in the patient in a minimally invasive manner and which includes
  (1) a housing,
  (2) an operating handle mounted on said housing,
  (3) at least one fastener stored in said housing, said fastener having an elastic limit, and
  (4) a fastener handling means on said housing and operationally connected to said operating handle to be controlled by said operating handle for storing said fastener and securing said fastener through said flexible sewing cuff and into the patient's tissue from one side of said sewing cuff and the tissue to attach said flexible sewing cuff to the patient without deforming said fastener beyond its elastic limit.

15. In combination:

A) a heart valve prosthesis which includes
  (1) a flexible sewing cuff,
  (2) a prosthesis valve separate and spaceable from said flexible sewing cuff, and
  (3) means for securely attaching said valve to said flexible sewing cuff after said flexible sewing cuff has been placed in a patient; and B) a tool for placing said flexible sewing cuff in the patient in a minimally invasive manner and which includes
  (1) a housing,
  (2) an operating handle mounted on said housing,
  (3) at least one fastener stored in said housing, said fastener having an elastic limit, and
  (4) a fastener handling means on said housing and operationally connected to said operating handle to be controlled by said operating handle for storing said fastener and securing said fastener through said flexible sewing cuff and into the patient's tissue to attach said flexible sewing cuff to the patient without deforming said fastener beyond its elastic limit.

16. In combination:

A) a multipart prosthesis which includes
  (1) a flexible sewing cuff,
  (2) a prosthesis valve separate and spaceable from said flexible sewing cuff, and (3) anchor elements for securely attaching said prosthesis valve to said flexible sewing cuff after said flexible sewing cuff has been attached to a patient; and B) a tool for attaching said flexible sewing cuff to the patient and which includes
(1) a housing,
(2) at least one fastener stored in said housing in a tissue-penetrating shape and having an elastic limit, and
(3) a fastener handling means on said tool for forcing said fastener into the patient from one side of said flexible sewing cuff and the patient's tissue to attach said flexible sewing cuff to the patient and deforming said fastener beyond its elastic limit into a cuff-retaining shape.

17. In combination:

A) a multipart prosthesis valve includes
(1) a flexible sewing cuff,
(2) a prosthesis valve separate and spaceable from said flexible sewing cuff, and
(3) anchor elements for securely attaching said prosthesis valve to said flexible sewing cuff after said flexible sewing cuff has been attached to a patient; and B) a tool for attaching said flexible sewing cuff to the patient and which includes
(1) a housing,
(2) at least one fastener stored in said housing, said fastener being self-tapping to penetrate the patient's tissue when rotated,
(3) a fastener handling means on said tool for imparting rotation to said fastener and forcing said fastener into the patient's tissue from one side of the patient's tissue to attach said flexible sewing cuff to the patient.

18. In combination:

A) a multipart prosthesis which includes
(1) a flexible sewing cuff,
(2) a prosthesis valve separate and spaceable from said flexible sewing cuff, and
(3) anchor elements for securely attaching said prosthesis valve to said flexible sewing cuff after said flexible sewing cuff has been attached to a patient; and B) a tool for attaching said flexible sewing cuff to the patient and which includes
(1) a housing,
(2) at least one fastener stored in said housing, and (3) a fastener handling means on said tool for forcing said fastener into the patient from one side of the patient's tissue and attaching said flexible sewing cuff to the patient.

19. In combination:

A) a multipart prosthesis which includes
(1) a flexible sewing cuff,
(2) a prosthesis valve separate and spaceable from said flexible sewing cuff, and
(3) anchor elements for securely attaching said prosthesis valve to said flexible sewing cuff after said flexible sewing cuff has been attached to a patient;

B) a fastener for attaching said sewing cuff to the patient from one side of said sewing cuff, said fastener having an elastic limit; and C) means for forcing said fastener through said sewing cuff and attaching said sewing cuff to the patient without exceeding the elastic limit of said fastener whereby said fastener is non-formed when said sewing cuff is attached to the patient by said fastener.

20. In combination:

A) a multipart heart valve prosthesis which includes
(1) a flexible sewing cuff,
(2) a prosthesis heart valve separate and spaceable from said flexible sewing cuff, and
(3) anchor elements for securely attaching said prosthesis heart valve to said flexible sewing cuff after said flexible sewing cuff has been attached to a patient;

B) a fastener for attaching said sewing cuff to the patient from one side of said sewing cuff, said fastener having an elastic limit and an initial shape; and C) [means] *a tool carrying the fastener, the tool configured* for forcing said fastener through said sewing cuff and attaching said sewing cuff to the patient without exceeding the elastic limit of said fastener.

21. In combination:

A) a multipart prosthesis which includes
(1) a flexible sewing cuff,
(2) a prosthesis valve separate and spaceable from said flexible sewing cuff, said prosthesis valve being attachable to said flexible sewing cuff after said flexible sewing cuff has been attached to a patient, and B) a tool operative to attach said flexible sewing cuff to the patient in a minimally invasive manner, the tool including
(1) a housing,
(2) an operating member mounted on one end of said housing,
(3) at least one fastener carried by said housing, said fastener having an elastic limit,
[(4) mounting structure on said tool operative to releasably carry said flexible sewing cuff,] and
[(5)] *(4)* a fastener carrier on said housing, said fastener carrier being operatively connected to said operating member such that actuation of said operating member secures said fastener through said flexible sewing cuff and into the patient's tissue from one side of said sewing cuff and the tissue to attach said flexible sewing cuff to the patient without deforming said fastener beyond its elastic limit.

22. In combination:

A) a multipart prosthesis which includes
(1) a flexible sewing cuff,
(2) a prosthesis valve separate from said flexible sewing cuff and attachable to said flexible sewing cuff after said flexible sewing cuff has been attached to a patient, and B) a tool operative to attach said flexible sewing cuff in the patient in a minimally invasive manner, the tool including
(1) a housing,
(2) an operating member mounted on said housing,
(3) at least one fastener stored in said housing, said fastener having an elastic limit,
[(4) mounting structure on said tool operative to releasably carry said flexible sewing cuff,] and
[(5)] *(4)* a fastener carrier on said housing, said fastener carrier being operatively connected to said operating member such that actuation of said operating member secures said fastener through said flexible sewing cuff and into the patient's tissue from one side of said sewing cuff and the tissue to attach said flexible sewing cuff to the patient without deforming said fastener beyond its elastic limit.

23. In combination:

A) a multipart prosthesis which includes
(1) a flexible sewing cuff,
(2) a prosthesis valve separate and spaceable from said flexible sewing cuff, and
(3) anchor elements configured to attach said prosthesis valve to said flexible sewing cuff after said flexible sewing cuff has been attached to a patient; and B) a tool operative to attach said flexible sewing cuff to the patient, said tool including
(1) a housing,
(2) at least one fastener carried by said housing, said fastener having a tissue-penetrating shape and an elastic limit, and
(3) a fastener handling device on said tool operating to force said fastener into the patient from one side of said flexible sewing cuff and the patient's tissue to attach said flexible sewing cuff to the patient and thereby deform said fastener beyond its elastic limit into a cuff-retaining shape.

24. In combination:

A) a multipart prosthesis which includes
(1) a flexible sewing cuff,
(2) a prosthesis valve separate and spaceable from said flexible sewing cuff, and
(3) anchor elements configured to attach said prosthesis valve to said flexible sewing cuff after said flexible sewing cuff has been attached to a patient; and B) a tool operative to attach said flexible sewing cuff to the patient, said tool including
(1) a housing,
(2) at least one fastener carried by said housing, said fastener being self-tapping to penetrate the patient's tissue when rotated,
(3) a fastener handling device on said tool operative to impart rotation to said fastener and thereby force said fastener into the patient's tissue from one side of the patient's tissue to attach said flexible sewing cuff to the patient.

25. In combination:

A) a multipart prosthesis which includes
(1) a flexible sewing cuff,
(2) a prosthesis valve separate and spaceable from said flexible sewing cuff, and
(3) anchor elements configured to attach said prosthesis valve to said flexible sewing cuff after said flexible sewing cuff has been attached to a patient; and B) a tool operative to attach said flexible sewing cuff to the patient, said tool including
(1) a housing,
(2) at least one fastener carried by said housing, and
(3) a fastener handling device on said tool operative to force said fastener into the patient from one side of the patient's tissue and thereby attach said flexible sewing cuff to the patient.

26. In combination:

A) a multipart prosthesis which includes
(1) a flexible sewing cuff,
(2) a prosthesis valve separate and spaceable from said flexible sewing cuff, and
(3) anchor elements configured to attach said prosthesis valve to said flexible sewing cuff after said flexible sewing cuff has been attached to a patient;

B) a fastener for attaching said sewing cuff to the patient from one side of said sewing cuff, said fastener having an elastic limit; and C) a tool *carrying said fastener and* operative to force said fastener through said sewing cuff and thereby attach said sewing cuff to the patient without exceeding the elastic limit of said fastener, whereby said fastener is nonformed when said sewing cuff is attached to the patient by said fastener.

27. In combination:

A) a multipart heart valve prosthesis which includes
(1) a flexible sewing cuff,
(2) a prosthesis heart valve separate and spaceable from said flexible sewing cuff, and
(3) anchor elements configured to attach said prosthesis valve to said flexible sewing cuff after said flexible sewing cuff has been attached to a patient;

B) a fastener configured to attach said sewing cuff to the patient from one side of said sewing cuff, said fastener having an elastic limit and an initial shape; and C) a tool *carrying said fastener and* operative to force said fastener through said sewing cuff thereby attach said sewing cuff to the patient without exceeding the elastic limit of said fastener and while retaining the initial shape of said fastener.

*28. The combination of claim 20, wherein the fastener comprises two legs that overlap each other in the initial shape.*

*29. The combination of claim 28, wherein the tool comprises a tool element configured for separating the legs of the fastener apart such that the legs regain the initial shape when the tool is withdrawn after the fastener is forced through the sewing cuff.*

*30. The combination of claim 29, wherein the tool element comprises a fastener track for storing a plurality of fasteners therein, the tool element further comprising an advancing mechanism for moving fasteners down the track until the fasteners drop off the track.*

*31. The combination of claim 29, wherein the tool element comprises an extender pin that holds the legs of each fastener apart before the fastener is released from the tool.*

*32. The combination of claim 20, wherein the flexible sewing cuff is fully flexible so the cuff can be deformed to conform to tissue of the patient.*

*33. The combination of claim 20, wherein the flexible sewing cuff comprises polyester fabric.*

*34. The combination of claim 20, wherein the anchor elements comprise drawstrings.*

*35. The combination of claim 21, wherein the fastener comprises two legs that overlap each other in an initial shape.*

*36. The combination of claim 35, wherein the tool comprises a tool element configured for separating the legs of the fastener apart such that the legs regain the initial shape when the tool is withdrawn after the fastener is forced through the sewing cuff.*

*37. The combination of claim 36, wherein the tool element comprises a fastener track for storing a plurality of fasteners therein, the tool element further comprising an advancing mechanism for moving fasteners down the track until the fasteners drop off the track.*

*38. The combination of claim 36, wherein the tool element comprises an extender pin that holds the legs of each fastener apart before the fastener is released from the tool.*

*39. The combination of claim 21, wherein the tool further comprises mounting structure operative to releasably carry the flexible sewing cuff.*

*40. The combination of claim 21, wherein the flexible sewing cuff is fully flexible so the cuff can be deformed to conform to tissue of the patient.*

*41. The combination of claim 21, wherein the flexible sewing cuff comprises polyester fabric.*

*42. The combination of claim 21, wherein the multipart prosthesis comprises anchor elements for attaching the prosthesis heart valve to the flexible sewing cuff.*

*43. The combination of claim 42, wherein the anchor elements comprise drawstrings.*

*44. A system for implanting a prosthesis heart valve within an annulus in a heart of a patient, comprising:*

*a flexible sewing cuff having a shape for implantation within the annulus in the heart;*

*a tool carrying one or more fasteners, each fastener having an elastic limit, an initial shape, and two legs that overlap in the initial shape, the tool configured for separating the legs of each fastener apart, and forcing the legs through the sewing cuff into tissue of the annulus to attach the sewing cuff to the patient without exceeding the elastic limit of each fastener; and*

*a prosthesis heart valve separate and spaceable from the sewing cuff, the prosthesis valve being attachable to the sewing cuff after the sewing cuff has been attached to the annulus.*

*45. The system of claim 44, wherein the tool comprises a tool element configured for separating the legs of the fastener apart such that the legs regain the initial shape when the tool is withdrawn after the fastener is forced through the sewing cuff.*

*46. The system of claim 45, wherein the tool element comprises a fastener track for storing a plurality of fasteners therein, the tool element further comprising an advancing mechanism for moving fasteners down the track until the fasteners drop off the track.*

*47. The system of claim 45, wherein the tool element comprises an extender pin that holds the legs of each fastener apart before the fastener is released from the tool.*

*48. The system of claim 44, wherein the tool further comprises mounting structure operative to releasably carry the flexible sewing cuff.*

*49. The system of claim 44, wherein the flexible sewing cuff is fully flexible so the cuff can be deformed to conform to tissue of the patient.*

*50. The system of claim 44, wherein the sewing cuff comprises polyester fabric.*

*51. The system of claim 44, wherein at least one of the sewing cuff and the prosthesis heart valve comprises anchor elements for securely attaching the prosthesis heart valve to the sewing cuff.*

*52. The system of claim 51, wherein the anchor elements comprise drawstrings.*

*53. A system for implanting a prosthesis heart valve within a annulus in a heart of a patient, comprising:*

*a flexible sewing cuff having a shape for implantation within the annulus in the heart;*

*a tool carrying one or more fasteners, each fastener having an elastic limit, an initial shape, and two legs that overlap in the initial shape, the tool configured for holding the legs of each fastener apart, and forcing the legs through the sewing cuff into tissue of the annulus to attach the sewing cuff to the patient without exceeding the elastic limit of each fastener; and*

*a prosthesis heart valve separate and spaceable from the sewing cuff, at least one of the sewing cuff and the prosthesis heart valve comprising anchor elements for securely attaching the prosthesis heart valve to the sewing cuff.*

*54. The system of claim 53, wherein the tool comprises a tool element configured for separating the legs of the fastener apart such that the legs regain the initial shape when the tool is withdrawn after the fastener is forced through the sewing cuff.*

*55. The system of claim 54, wherein the tool element comprises a fastener track for storing a plurality of fasteners therein in the initial shape, the tool element further comprising an advancing mechanism for moving fasteners down the track until the fasteners drop off the track.*

*56. The system of claim 53, wherein the tool element comprises an extender pin that holds the legs of each fastener apart before the fastener is released from the tool.*

*57. The system of claim 53, wherein the flexible sewing cuff is fully flexible so the cuff can be deformed to conform to tissue of the patient.*

*58. The system of claim 53, wherein the sewing cuff comprises polyester fabric.*

*59. The system of claim 53, wherein the anchor elements comprise drawstrings.*

*60. The system of claim 53, wherein the sewing cuff comprises an indicator for signaling when the prosthesis heart valve is properly seated in the sewing cuff.*

*61. The system of claim 60, wherein the indicator is configured for providing a tactile feedback when the prosthesis heart valve is properly seated in the sewing cuff.*

*62. A system for implanting a prosthesis heart valve within an annulus in a heart of a patient, comprising:*

*a sewing cuff having a shape for implantation with the annulus in the heart;*

*a tool carrying one or more fasteners, each fastener having an elastic limit, an initial shape, and two legs that overlap in the initial shape, the tool configured for holding the legs of each fastener apart, and forcing the legs through the sewing cuff into tissue of the annulus to attach the sewing cuff to the patient without exceeding the elastic limit of each fastener; and*

*a prosthesis heart valve separate and spaceable from the sewing cuff, at least one of the sewing cuff and the prosthesis heart valve comprising anchor elements for securely attaching the prosthesis heart valve to the sewing cuff.*

*63. The system of claim 62, wherein the tool comprises a tool element configured for separating the legs of the fastener apart such that the legs regain the initial shape when the tool is withdrawn after the fastener is forced through the sewing cuff.*

*64. The system of claim 63, wherein the tool element comprises a fastener track for storing a plurality of fasteners therein in the initial shape, the tool element further comprising an advancing mechanism for moving fasteners down the track until the fasteners drop off the track.*

*65. The system of claim 63, wherein the tool element comprises an extender pin that holds the legs of each fastener apart before the fastener is released from the tool.*

*66. The system of claim 62, wherein the sewing cuff is flexible.*

*67. The system of claim 66, wherein the sewing cuff is fully flexible so the cuff can be deformed to conform to tissue of the patient.*

*68. The system of claim 62, wherein the sewing cuff comprises polyester fabric.*

*69. The system of claim 62, wherein the anchor elements comprise drawstrings.*

*70. The system of claim 62, wherein the sewing cuff comprises an indicator for signaling when the prosthesis heart valve is properly seated in the sewing cuff.*

*71. The system of claim 70, wherein the indicator is configured for providing a tactile feedback when the prosthesis heart valve is properly seated in the sewing cuff.*

*72. The system of claim 63, wherein the tool element comprises a fastener track for storing a plurality of fasteners therein in the initial shape, the tool element further comprising an advancing mechanism for moving fasteners down the track.*

* * * * *